United States Patent [19]

Teutsch et al.

[11] Patent Number: 5,043,332

[45] Date of Patent: Aug. 27, 1991

[54] NOVEL 11β-SUBSTITUTED-19-NOR-STERIODS

[75] Inventors: Jean-Georges Teutsch, Pantin; Vesperto Torelli, Maison-Alfort; Roger Deraedt, Pavilons-Sous-Bois; Daniel Philibert, La Varenne-Saint-Hilaire; Germain Costerousse, Saint-Maurice, all of France

[73] Assignee: Roussel Uclaf, Paris, France

[21] Appl. No.: 421,526

[22] Filed: Oct. 13, 1989

Related U.S. Application Data

[60] Division of Ser. No. 810,316, Dec. 17, 1985, Pat. No. 4,978,657, which is a continuation-in-part of Ser. No. 693,682, Jan. 22, 1985, Pat. No. 4,634,695, which is a continuation-in-part of Ser. No. 614,440, May 25, 1984, Pat. No. 4,519,946, which is a division of Ser. No. 595,267, Mar. 30, 1984, abandoned, which is a division of Ser. No. 386,967, Jun. 10, 1982, Pat. No. 4,447,424, which is a continuation-in-part of Ser. No. 338,077, Jan. 8, 1982, Pat. No. 4,386,085, and a continuation-in-part of Ser. No. 760,703, Jul. 30, 1985, Pat. No. 4,634,696, which is a division of Ser. No. 501,373, Jun. 6, 1983, Pat. No. 4,547,493.

[30] Foreign Application Priority Data

Jan. 9, 1981 [FR] France .................. 81 00272
Jun. 11, 1982 [FR] France .................. 82 70205

[51] Int. Cl.$^5$ .................. A61K 31/56; A61K 31/58; C07S 53/00
[52] U.S. Cl. .................. 514/173; 514/178; 514/179; 552/505; 552/508; 552/515
[58] Field of Search .................. 514/178, 179, 173; 552/508, 505, 515

[56] References Cited

U.S. PATENT DOCUMENTS 4,701,499 10/1987 Torelli et al. .................. 514/175
4,891,365 1/1990 Wiechert et al. .................. 514/173
4,891,368 1/1990 Chwalisz et al. .................. 514/179

Primary Examiner—Stanley J. Friedman
Assistant Examiner—T. J. Criares
Attorney, Agent, or Firm—Bierman and Muserlian

[57] ABSTRACT

Novel 19-nor-steroids of the formula

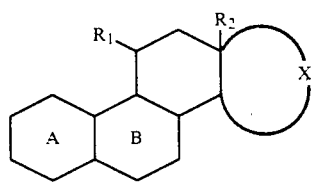

wherein $R_1$ is an organic group of 1 to 18 carbon atoms optionally containing at least one heteroatom with the atom immediately adjacent the 11-carbon atom being carbon, $R_2$ is a hydrocarbon of 1 to 8 carbon atoms, X is the remainder of a pentagonal or hexagonal ring optionally substituted and optionally containing one unsaturated—bond, the A and B rings are selected from the group consisting of

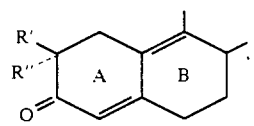
(a)

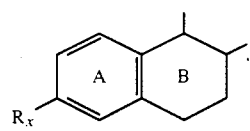

(b)

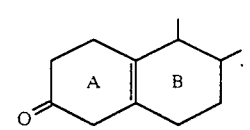

(c)

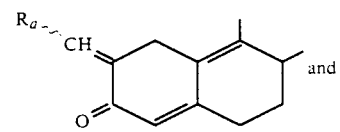

(d)

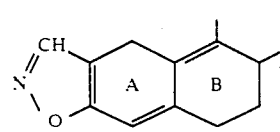

(e)

R' and R" are individually selected from the group consisting of hydrogen, —CN and alkyl of 1 to 4 carbon atoms, $R_x$ is selected from the group consisting of hydrogen and $OR_e$, $R_e$ is selected from the group consisting of hydrogen, optionally substituted alkyl of 1 to 6 carbon atoms and acyl, $R_a$ may be in the E or Z positions as indicated by the wavy line and is selected from the group consisting of

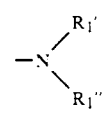

and acyloxy, $R'_a$ and $R''_a$ are alkyl of 1 to 4 carbon atoms or taken together with the nitrogen atom form a heterocycle of 5 to 6 chain members optionally containing another heteroatom—with the proviso that when A and B are

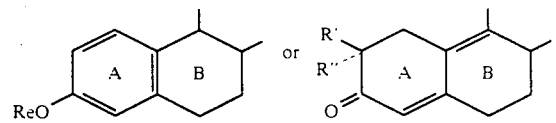

(Abstract continued on next page.)

wherein R' and R" are both hydrogen, $R_1$ contains at least one nitrogen, phosphorus or silicium atom and when A and B are
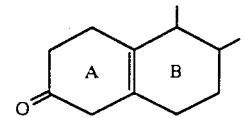
$R_1$ is not a linear alkyl
and their non-toxic, pharmaceutically acceptable acid addition salts having a remarkable antiglucocorticoid activity, their preparation and novel intermediates.
14 Claims, No Drawings

NOVEL 11β-SUBSTITUTED -19-NOR-STERIODS

PRIOR APPLICATION

This is a division of Ser. No. 810,316, filed Dec. 17, 1985, now U.S. Pat. No. 4,978,657, which is a combined continuation-in-part application of U.S. patent application Ser. No. 693,682 filed Jan. 22, 1985 now U.S. Pat. No. 4,634,695 which in turn is a continuation-in-part of copending application Ser. No. 614,440 filed May 25, 1984 now U.S. Pat. No. 4,519,946 which in turn is a division of application Ser. No. 595,267 filed Mar. 30, 1984 now abandoned which in turn is a division of U.S. patent application Ser. No. 386,967 filed June 10, 1982, now U.S. Pat. No. 4,447,424 which is a continuation-in-part of U.S. patent application Ser. No. 338,077 filed Jan. 8, 1982, now U.S. Pat. No. 4,386,085 and U.S. patent application Ser. No. 760,703 filed July 30, 1985, now U.S. Pat. No. 4,634,696 which in turn is a division of U.S. patent application Ser. No. 501,373 filed June 6, 1983, now U.S. Pat. No. 4,547,493.

STATE OF THE ART

U.S. Pat. No. 4,233,296 describes steroids being substituted in the 11-position with substituents other than the present formula which require an organic substituent containing a nitrogen, phosphorous or silicon atom. U.S. Pat. No. 3,190,796 describes steroids having a hydroxyl in the 11β-position. Schonemann et al European Journal of Medicin Chemistry, Chimica Therapeutica, Vol. 15, No. 4, (July, Aug. 1980), p. 333-335] describes steroids substituted in the 11β-position with $CH_2=$, $-CH_2OH$ and

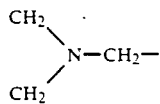

Commonly assigned U.S. Pat. No. 4,272,530 and copending U.S. patent application Ser. No. 469,042 filed Feb. 23, 1983 describe related steroids of different structures.

OBJECTS OF THE INVENTION

It is an object of the invention to provide the novel compounds of formula I and their non-toxic, pharmaceutically acceptable acid addition salts and a novel process for their preparation and novel intermediates.

It is another object of the invention to provide novel antiglucocorticoid compositions and a novel method of inducing antiglucocorticoidal activity in warm-blooded animals.

These and other objects and advantages of the invention will become obvious from the following detailed description.

THE INVENTION

The novel compounds of the invention are selected from the group consisting of 19-nor-steroids of the formula

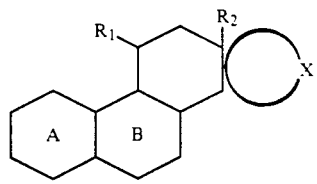

wherein $R_1$ is an organic group of 1 to 18 carbon atoms optionally containing at least one heteroatom with the atom immediately adjacent the 11-carbon atom being carbon, $R_2$ is a hydrocarbon of 1 to 8 carbon atoms, X is the remainder of a pentagonal or hexagonal ring optionally substituted and optionally containing one unsaturated—bond, the A and B rings are selected from the group consisting of

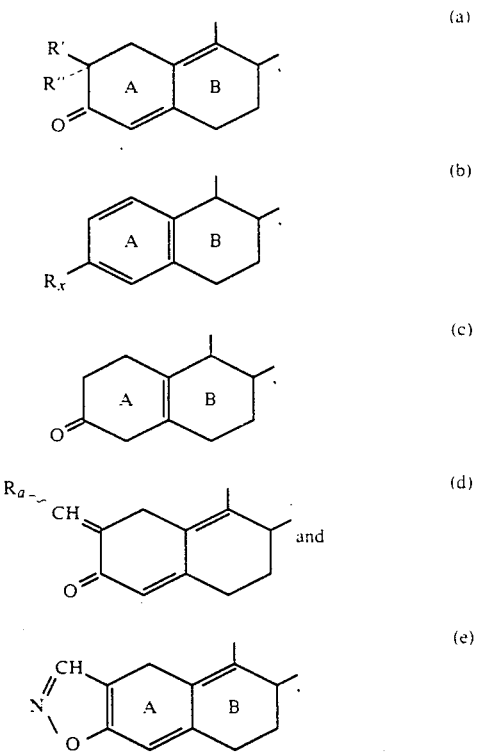

$R'$ and $R''$ are individually selected from the group consisting of hydrogen, —CN and alkyl of 1 to 4 carbon atoms $R_x$ is selected from the group consisting of hydrogen and $OR_e$, $R_e$ is selected from the group consisting of hydrogen, optionally substituted alkyl of 1 to 6 carbon atoms and acyl, $R_a$ may be in the E or Z positions as indicated by the wavy line and is selected from the group consisting of

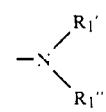

and acyloxy, $R_a'$ and $R_a''$ are alkyl of 1 to 4 carbon atoms or taken together with the nitrogen atom form a heterocycle of 5 to 6 chain members optionally containing another heteroatom with the proviso that when A and B are

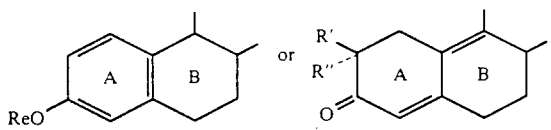

wherein R' and R" are both hydrogen, $R_1$ contains at least one nitrogen, phosphorus or silicium atom and when A and B are

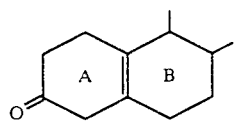

$R_1$ is not a linear alkyl and their non-toxic, pharmaceutically acceptable acid addition salts.

$R_1$ is preferably an optionally unsaturated alkyl of 1 to 12 carbon atoms such as methyl, ethyl, isopropyl, propyl, butyl, isobutyl, tert.-butyl, n-pentyl, n-hexyl, 2-methyl-pentyl, 2,3-dimethyl-pentyl, n-heptyl, 2-methyl-hexyl-, 2,2-dimethyl-pentyl, 3,3-dimethyl-pentyl, 3-ethyl-pentyl, n-octyl, 2,2-dimethyl-hexyl, 3,3-dimethyl-hexyl, 3-methyl-3-ethyl-pentyl, nonyl, 2,4-dimethyl-heptyl, n-decyl, vinyl, isopropenyl, allyl, 2-methyl-allyl and isobutenyl.

Examples of suitable optional substituents are thioalkyl such as thiomethyl or thioethyl and $R_1$ may be substituted with at least one halogen such as fluorine, chlorine, bromine, iodine; substituted amino such as dimethylamino, $R_1$ may also be aryl or aralkyl, especially phenyl or benzyl and the aromatic rings may be substituted in the p-, o- or m- positions with at least one member of the group consisting of alkyl of 1 to 4 carbon atoms, alkoxy of 1 to 4 carbon atoms such as methoxy, ethoxy, propoxy, isopropoxy, butoxy, isobutoxy and tert.-butoxy; alkenyloxy of 2 to 4 carbon atoms such as allyloxy or vinyloxy; halogen such as chlorine or fluorine; —OH; —CF₃; alkylthio of 1 to 4 carbon atoms such as methylthio or ethylthio which may be oxidized to sulfoxide or sulfone or a combination thereof such as 3-fluoro-4-dimethylamino-phenyl.

$R_1$ may also be an aryl heterocycle optionally substituted such as thienyl, furyl, isothienyl, isofuryl, thiazolyl, isothiazolyl, oxazolyl, isoxazolyl, thiadiazolyl, pyridinyl, piperidinyl and other heterocycles known to those skilled in the art.

$R_1$ may also be cycloalkyl such as cyclopropyl, cyclobutyl, cyclopentyl or cyclohexyl; cycloalkenyl such as cyclobutenyl or cyclopropenyl; aryl substituted with a member of the group consisting of amino optionally substituted with one or 2 alkyls of 1 to 8 carbon atoms, nitrogen heterocycle group optionally containing a second oxygen, sulfur or nitrogen heteroatom such as morpholino or piperidinyl, substituted aminoalkyl or alkoxy such as dimethylaminomethyl, dimethylaminoethyl or dimethylaminoethoxy or a silicum group such as trimethylsilylphenyl. The preferred aryl is phenyl and the substituent may also be a nitrogen atom which can be oxidized. The preferred heteroatom of $R_1$ is sulfur or nitrogen.

$R_2$ is preferably substituted alkyl of 1 to 4 carbon atoms such as methyl, ethyl, propyl, isopropyl or butyl and preferably methyl or ethyl and most preferably methyl. X is preferably an optionally substituted pentagonal ring and R' and R" are alkyl as discussed above.

When Re is a substituted alkyl, it is preferably substituted with a dialkylamino such as dimethylamino, diethylamino or methyl ethylamino. When Ra is

it is preferably an dialkylamino such as dimethylamino, diethylamino or methylethylamino, it also is pyrrolidino, piperidino or morpholino.

$R_a$ may also be alkanoyloxy such as acetyloxy, propionyloxy and their higher homologs or arylcarbonyloxy such as benzoyloxy.

Examples of suitable acids for the preparation of the non-toxic, pharmaceutically acceptable acid addition salts are as mineral acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, arylsulfonic acids such as benzene sulfonic acid and p-toluene sulfonic acid and arylcarboxylic acids.

Among the preferred compounds of formula I are those wherein X is a ring of the formula

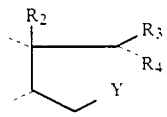

wherein $R_2$ has the above definition, the dotted line in the 16,17-position indicates an optional double bond. Y is

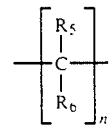

n is 1 or 2, $R_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, $R_6$ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms and $R_3$ and $R_4$ are individually selected from the group consisting of hydrogen, —OH, —OAlK₄,

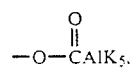

alkenyl and alkynyl of 2 to 8 carbon atoms,

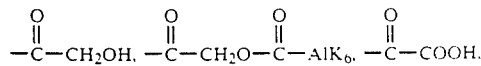

-continued

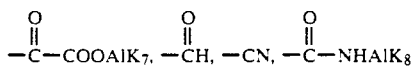

or R₃ and R₄ together with the carbon atoms are

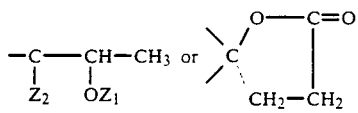

AlK₄, AlK₅ and AlK₈ are selected from the group consisting of alkyl of 1 to 8 carbon atoms and aralkyl of 7 to 15 carbon atoms, AlK₆ are selected from the group consisting of alkyl of 1 to 8 carbon atoms optionally substituted and aralkyl of 7 to 15 carbon atoms, alk₇ and Z₂ are alkyl of 1 to 8 carbon atoms and Z₁ is selected from the group consisting of hydrogen, alkyl of 1 to 8 carbon atoms and acyl of 1 to 8 carbon atoms.

Examples of preferred examples of R₅ or R₆ are methyl, ethyl, vinyl, isopropenyl, allyl, ethynyl, propynyl, phenyl and benzyl. Preferred examples of R₃ and R₄ are —OAlK₄ and

wherein AlK₄ and AlK₅ are methyl, ethyl, n-propyl, butyl, pentyl, hexyl or benzyl or are vinyl, isopropenyl, allyl, 2-methylallyl, —C≡CH, —C≡CAlK₉ wherein AlK₉ is methyl, ethyl, n-propyl, isopropyl, isopropenyl, butyl, benzyl or CF₃—AlK₆, AlK₇ and AlK₈ have the same preferred values as AlK₄ and AlK₅. The preferred compounds are those in which R₃ and R₄ are different except if one is hydrogen.

Among preferred values of

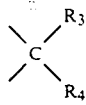

are the groups

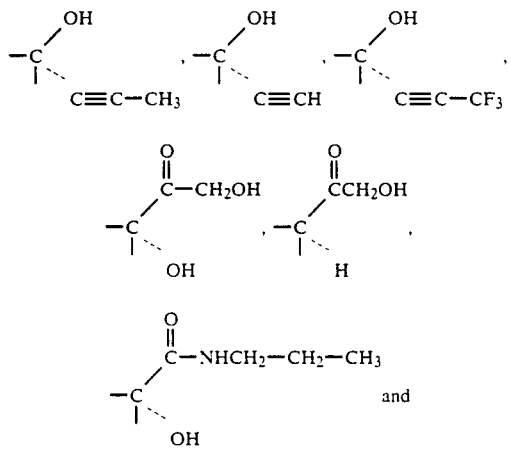

-continued

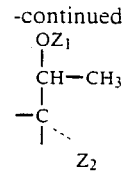

wherein Z₁ is hydrogen, alkyl of 1 to 8 carbon atoms or acyl of 2 to 8 carbon atoms such as acetyloxy or benzoyl and Z₂ is alkyl of 1 to 8 carbon atoms such as methyl. More preferable is the group

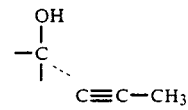

The D ring of the compounds of formula I is preferably not unsaturated, n is 1 and R₅ and R₆ are hydrogen. Another preferred group of compounds are those of formula I wherein R₃ is —OH or

and R₄ is alkenyl or alkynyl of 2 to 4 carbon atoms

Among the preferred compounds of formula I are those wherein R₁ is a hydrocarbon of 1 to 18 carbon atoms containing at least one nitrogen atom and especially primary, secondary or tertiary alkyl of 1 to 8 carbon atoms containing at least one heteroatom selected from the group consisting of oxygen, nitrogen and sulfur, at least one being nitrogen or substituted with a heterocycle containing at least one nitrogen atom. The hydrocarbon may be alkyl such as methyl, ethyl, n-propyl, isopropyl, butyl, isobutyl, tert.-butyl, pentyl, hexyl or cycloalkyl such as cyclopropyl, cyclobutyl, cyclopentyl or cyclohexyl. The heterocycle containing at least one nitrogen is preferably 2-pyridyl, 3-pyridyl, 4-pyridyl, thiazolyl or piperidinyl.

Another preferred groups of compounds of the invention are those wherein R₁ is a heterocycle containing at least one nitrogen atom optionally substituted with alkyl of 1 to 8 carbon atoms such as 2-pyridyl, 3-pyridyl, 4-pyridyl, thiazolyl or piperidinyl and the alkyl substituent is preferably methyl, ethyl or n-propyl.

R₁ may also preferably be aryl or aralkyl carrying an amino of the formula

wherein R₇ and R₈ are alkyl of 1 to 8 carbon atoms or primary, secondary or tertiary alkyl of 1 to 8 carbon atoms containing at least one heteroatom of the group consisting of —O—, —S— or —N— with at least one being nitrogen or substituted with a heterocycle containing at least one nitrogen atom. The alkyl, aryl, aralkyl and heterocycles are those discussed above.

Especially preferred are compounds of formula I wherein R₁ is selected from the group consisting of 2-pyridyl, 3-pyridyl, 4-pyridyl,

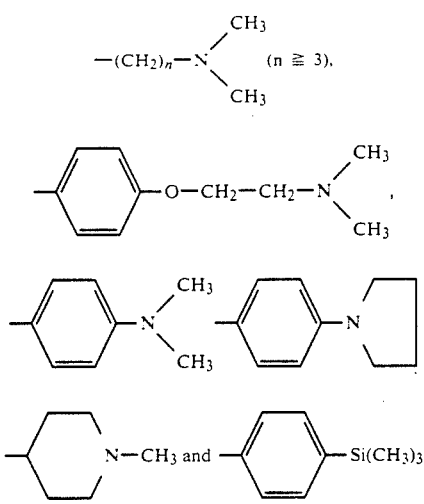

Another preferred group of compounds of formula I are those wherein $R_1$ is selected from the group consisting of thienyl, furyl, cycloalkyl of 3 to 6 carbon atoms and phenyl optionally substituted with at least one member of the group consisting of —OH, halogen, —CF$_3$, alkyl and alkoxy of 1 to 8 carbon atoms and alkylthio of 1 to 8 carbon atoms optionally oxidized to sulfoxide or sulfone and A and B rings are not

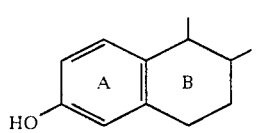

The preferred substituents are those listed above and among the more preferred values of $R_1$ are phenyl substituted with a member of the group consisting of chlorine, fluorine, methylthio, methylsulfonyl, methoxy, —OH and allyloxy.

Equally preferred compounds of formula I are those wherein the A and B rings are selected from the group consisting of

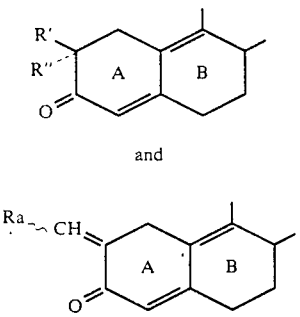

and wherein Ra is morpholino or acetyloxy and R' and R" are both methyl or both —CN or one is hydrogen and the other is methyl or —CN, or R' and R" are both hydrogen.

Specific preferred compounds of formula I are 2,2-dimethyl-11β-(4-dimethylaminophenyl)-17α-(prop-1-ynyl)-Δ$^{4,9}$-estradiene-17β-ol-3-one, 2,2-dicyano-11β-(4-dimethylaminophenyl)-17α-(prop-1-ynyl)-Δ$^{4,9}$-estradiene-17β-ol-3-one, 2α-methyl-11β-(4-dimethylaminophenyl)-17α-(prop-1-ynyl)-Δ$^{4,9}$-estradiene-17β-ol-3-one, 2β-methyl-11β-(4-dimethylaminophenyl)-17α-(prop-1-ynyl)-Δ$^{4,9}$-estradiene-17β-ol-3-one, 2-cyano-11β-(4-dimethylaminophenyl)-17α-(prop-1-ynyl)-Δ$^{4,9}$-estradiene-17β-ol-3-one, 11β-(4-dimethylamino)-17α-(prop-1-ynyl)-Δ$^{1,3,5(10)}$-estratriene-3,17β-diol, 11β-(4-dimethylaminophenyl)-17β-acetoxy-17α-(prop-1-ynyl)-Δ$^{1,3,5(10)}$-estratriene-3-ol, 3-methoxy-11β-(4-dimethylaminophenyl)-17α-(prop-1-ynyl)-Δ$^{1,3,5(10)}$-estratriene-17β-ol-, 3-methoxy-11β-(4-dimethylaminophenyl)-17β-acetoxy-17α-(prop-1-ynyl)-Δ$^{1,3,5(10)}$-estratriene, 11β-(3-methoxyphenyl)-17α-(prop-1-ynyl)-Δ$^{5(10)}$-estrene-17β-ol-3-one, (E)11β-(3-methoxyphenyl)-17α-(prop-1-enyl)-Δ$^{5(10)}$-estrene-17β-ol-3-one, 11β-(4-dimethylaminophenyl)-17α-(prop-1-ynyl)-Δ$^{5(10)}$-estrene-17β-ol-3-one, 2-(acetyloxymethylene)-11β-(4-dimethylaminophenyl)-17α-(prop-1-ynyl)-Δ$^{4,9}$-estradiene-17β-ol-3-one, 2-(4-morpholinomethylene)-11β-(4-dimethylaminophenyl)-17α-(prop-1-ynyl)-Δ$^{4,9}$-estradiene-17β-ol-3-one, 11β-(4-dimethylaminophenyl)-17α-(prop-1-ynyl)-isoxazolo[4,5-b]-Δ$^{4,9}$-estradiene-17β-ol, 11β-[4-(2-dimethylaminoethoxy)-phenyl]-Δ$^{1,3,5(10)}$-estratriene-3,17β-diol, 11β-[4-(2-dimethylaminoethoxy)-phenyl]-Δ$^{1,3,5(10)}$-estratriene-17β-ol, 3-(2-dimethylaminoethoxy)-11β-phenyl-Δ$^{1,3,5(10)}$-estratriene-17-ol, 11β-(4-pyridyl)-17α-(prop-1-ynyl)-Δ$^{4,9}$-estradiene-17β-ol-3-one, 11β-[4-(N,N-dimethylaminoethoxy)-phenyl]-17α-(prop-1-ynyl)-Δ$^{4,9}$-estradiene-17β-ol-3-one, 11β-[4-(N,N-dimethylamino)-phenyl]-17α-(prop-1-ynyl)-Δ$^{4,9}$-estradiene-17β-ol-3-one, 11β-[4-(N,N-dimethylamino)-phenyl]-23-methyl-19,21-dinor-17α-Δ$^{4,9,23}$cholatriene-20-yn-17β-ol-3-one, 11β-[4-(N,N-dimethylamino)-phenyl]-21-chloro-19-nor-17α-Δ$^{4,9}$-pregnadiene-20-yne-17β-ol-3-one, N-oxide of 11β-[4-(N,N-dimethylamino)-phenyl]-21-chloro-19-nor-17α-Δ$^{4,9}$-pregnadiene-20-yne-17β-ol-3-one, N-oxide of 9α,10α-epoxy-11β-[4-(N,N-dimethylamino)-phenyl]-21-chloro-19-nor-17α-Δ$^4$-pregnene-20-yne-17β-ol-3-one, 11β-[4-(N,N-dimethylamino)-phenyl]-21-phenyl-19-nor-17α-Δ$^{4,9}$-pregnadiene-20-yne-17β-ol-3-one, 11β-[4-(N,N-dimethylamino)-phenyl]-17α-(prop-2-ynyl)-Δ$^{4,9}$-estradiene-17β-ol-3-one, 11β-[4-(N,N-dimethylamino)-phenyl]-17α-ethynyl-Δ$^{4,9}$-estradiene-17β-ol-3-one, N-oxide of 11β-[4-(N,N-dimethylamino)-phenyl]-17α-(prop-1-ynyl)-Δ$^{4,9}$-estradiene-17β-ol-3-one, 11β-[4-(N,N-dimethylamino)-phenyl]-17α-(prop-2-enyl)-Δ$^{4,9}$-estradiene-17β-ol-3-one, 11β-[4-(N,N-dimethylaminoethylthio)-phenyl]-17α-(prop-1-ynyl)-Δ$^{4,9}$-estradiene-17β-ol-3-one, 11β-[4-(N,N-dimethylamino)-phenyl]-21-trimethylsilyl-19-nor-17α-Δ$^{4,9}$-pregnadiene-20-yne-17β-ol-3-one, γ-lactone of 11β-(4-dimethylaminophenyl)-19-nor-17α-Δ$^{1,3,5(10)}$-pregnatriene-3,17β-diol-21-carboxylic acid, γ-lactone of 3-methoxy-11β-(4-dimethylamino-phenyl)-19-nor-17α-Δ$^{1,3,5(10)}$-pregnatriene-17β-ol-21-carboxylic acid, γ-lactone of 11β-(4-dimethylamino-phenyl)-19-nor-17α-Δ$^{5(10)}$-pregnene-17β-ol-3-one-21-carboxylic acid, γ-lactone of 2α-methyl 11β-(4-dimethylamino-phenyl)-19-nor-17α-Δ$^{4,9}$-pregnadiene-17β-ol-3-one-21-carboxylic acid, γ-lactone of 2β-methyl 11β-(4-dimethylamino-phenyl)-19-nor-17α-Δ$^{4,9}$-pregnadiene-17β-ol-3-one-21-carboxylic acid, γ-lactone of 2,2-dimethyl 11β-(4-dimethylamino-phenyl)-19-nor-17α-Δ$^{4,9}$-pregnadiene-17β-ol-3-one-21-carboxylic acid, γ-lactone of 11β-[4-(N-methyl N-ethyl)amino-phenyl]-19-nor-17α-Δ$^{5(10)}$-pregnene-17β-ol-3-one-21-carboxylic acid, and their non-toxic, pharmaceutically acceptable acid addition salts.

The novel process of the invention for the preparation of the compounds of the formula

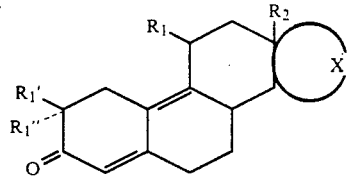

wherein $R_1$, $R_2$ and X have the above definition and $R_1'$ and $R_1''$ are each alkyl or one is hydrogen and the other is alkyl or each are —CN or one is alkyl and the other is —CN comprises reacting a compound of the formula

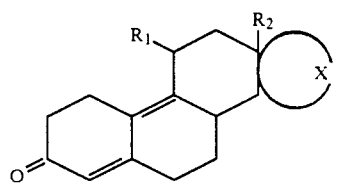

wherein $R_1$, $R_2$ and X have the above definitions after optionally reacting the same with a protective agent for functional groups with a strong base and/or an alkyl halide or tosyl cyanide or with an alkyl halide and then tosyl cyanide. followed by removal of any protective groups, if necessary.

The process for the preparation of compounds of the formula

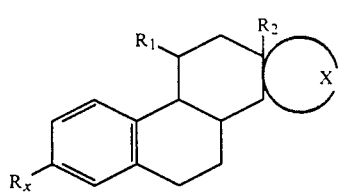

corresponding to the formula

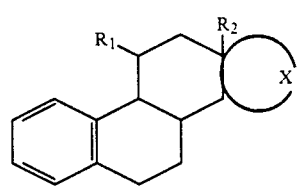

comprises reacting a compound of formula II with a reducing agent to obtain a compound of the formula

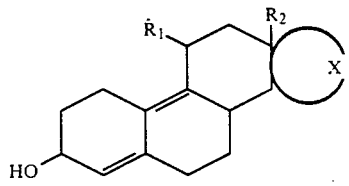

and reacting the latter with an aromatization acid agent to obtain the compound of formula $I_B$.

The process for the preparation of compounds of the formula

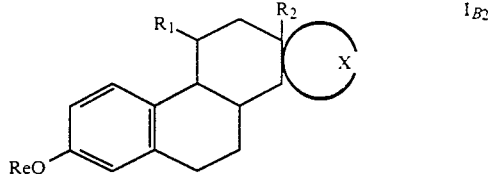

wherein Re, $R_1$, $R_2$ and X have the above definitions comprises reacting a compound of formula II with an aromatization agent which is then saponified and optionally reacted with an alkylation agent or an acylation agent.

The process for the preparation of a compound of the formula

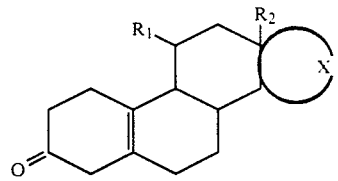

wherein $R_1$, $R_2$ and X have the above definitions comprises reacting a compound of formula II with a reducing agent.

The process for the preparation of a compound of the formula

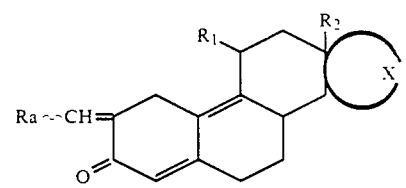

wherein Ra, $R_1$, $R_2$ and X have the above definitions comprises reacting a compound of formula II with a formylation agent to obtain a compound of the formula

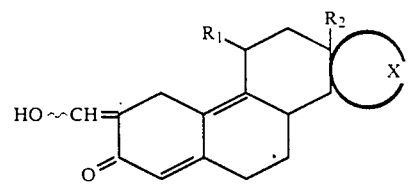

and reacting the latter with an acylation agent or an amine of the formula

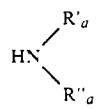

wherein $R_a'$ and $R_a''$ have the above definitions.

The process for the preparation of a compound of the formula

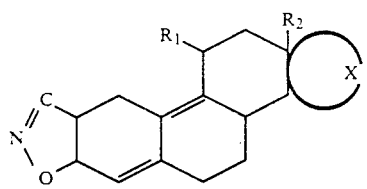

wherein $R_1$, $R_2$ and X have the above definitions comprises reacting a compound of formula III with hydroxylamine.

The process for the preparation of a compound of the formula

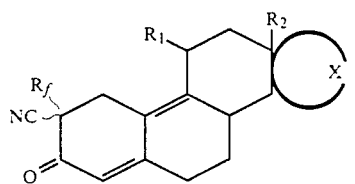

wherein $R_1$, $R_2$ and X have the above definitions and $R_f$ is hydrogen or alkyl comprises reacting a compound of formula $I_E$ with a base to obtain the compound of formula $I_{A'}$ wherein $R_f$ is hydrogen and if desired, reacting the latter with a strong base and an alkyl halide to obtain the compound of formula $I_{A'}$ wherein $R_f$ is alkyl.

When the compounds of formula II contain one or more groups capable of reacting with a reactant such as an alkyl halide, the groups preferably are protected with a group known in the literature. This is particularly important when the group

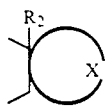

contains a 17β-ol and this group is preferably protected by tetrahydropyranyl by reacting the compound of formula II with dihydropyran.

The strong bases used are preferably alkali metal alcoholates such as potassium tert.-butylate but equally useful are alkali metal amides such as sodium amide or lithium amide prepared in situ. The alkyle halide is preferably an iodide such as methyl iodide and if gem dialkylation in the 2-positions is desired, at least two equivalents of the strong base are used and the reaction is effected in an excess of alkyl iodide. Monoalkylation is obtained when only one equivalent of the strong base is used. Generally, the α- and β-isomers may be separated by conventional techniques such as chromatography.

The addition of two cyano groups in the 2-position is effected with tosyl cyanide whose preparation is described in Chem. Com., 1968, p. 440 and is used as in Tetrahedron Letters No. 50 (1981), p. 5011. The addition of an alkyl halide and then tosyl cyanide yields the compounds wherein one of $R_1{'}$ and $R_1{''}$ is alkyl and the other is —CN and may be effected under the preceding conditions.

The eventual removal of the protective groups may be effected by the classical methods for instance, acid hydrolysis, preferably hydrochloric acid may be used to remove the tetrahydropyranyl group.

The reducing agent to prepare the compound of formula $II_1$ is preferably an alkali metal borohydride such as sodium borohydride and the reaction is preferably effected in an alkanol such as methanol or ethanol. The armoatization agent for the preparation of compounds of formula $I_{B1}$ is preferably an acyl halide such as acetyl bromide or acetic anhydride or a mixture thereof.

The preferred saponification agent is an alkali metal base such as sodium hydroxide or potassium hydroxide, sodium amide, potassium tert.-butylate or lithium acetylide in ethylenediamine. The reaction is preferably effected in a lower alkanol such as methanol or ethanol.

Depending on the conditions used and for example if the compound contains a group such as

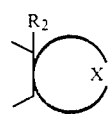

with a reactive group like 17β-ol, a partial acetylation of this group will occur resulting in a 17β-ol product containing a variable percentage of 17β-acetyloxy product and the two can be separated by the usual methods such as chromatography. When the starting compound of formula II contains a 17-one group in the pentagonal ring, it can be reduced with sodium borohydride for example.

The eventual alkylation can be effected by usual methods and the preferred alkylating agent is an alkyl halide such as alkyl iodide or an alkylsulfate, preferably methyl sulfate. The acylation may also be effected by known methods and is usually effected with an acyl halide. The reducing agent used to form the compounds of formula $I_C$ are preferably an alkali metal in liquid ammonia, preferably lithium but sodium is also useful.

Depending upon the amount of metal used, other portions of the molecule may be effected and for example, this is the case when the compound has the group

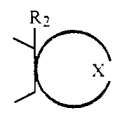

containing a 17α-acetylenic group such as propynyl. The use of two moles of alkali metal results in a practically selective reduction of a 3-keto-$\Delta^{4,9}$-steroid into a 3-keto-$\Delta^{5(10)}$-steroid. If a supplemental amount of reducing agent is used, there is simultaneously obtained a reduction of an acetylenic group into a trans olefin group, i.e. a 17-prop-1-ynyl into a 17α-prop-1-enyl. The separation of the two products may be effected by classical methods such as chromatography.

The formylation of the compounds of formula II is effected under known conditions such as by reaction with a formate such as alkyl formates, i.e. ethyl formate, in the presence of a strong base such as sodium hydride and the acylation of the compound of formula III is effected under known conditions as well. Preferably, the acylating agent is an acid anhydride or acid halide such as acetyl chloride and the reaction is effected in the presence of an acid receptor such as pyridine.

The reaction with an amine of the formula

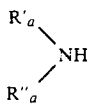

is effected under known conditions, preferably with heating. The reaction of the compound of formula III with hydroxylamine which is preferably in the form of an acid salt such as its hydrochloride is effected in a refluxing alkanol such as tert.-butanol. The hydrolysis of the compounds of formula $I_E$ is preferably effected with a base such as sodium hydroxide or potassium hydroxide, preferably in methanol. The alkylation of the compounds of formula $I_4'$ when $R_f$ is hydrogen is effected under the usual conditions indicated above.

In a preferred mode of the invention, the starting materials of formula II have the group

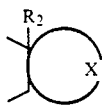

which is

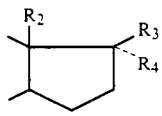

wherein $R_2$ is methyl, $R_3$ is —OH or

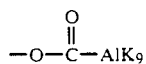

and $AlK_9$ is alkyl of 1 to 4 carbon atoms. $R_4$ is alkenyl or alkynyl of 2 to 4 carbon atoms and $R_1$ is

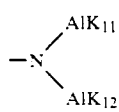

or alkoxyphenyl wherein the alkyl has 1 to 4 carbon atoms and $AlK_{11}$ and $AlK_{12}$ are alkyl of 1 to 4 carbon atoms.

The novel process of the invention for the preparation of compounds of formula II comprises reacting a compound of the formula

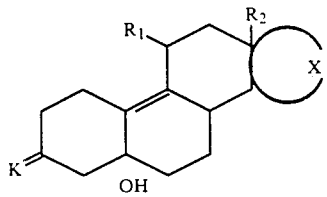

wherein K is a ketone blocked in the form of a ketal, thioketal, oxime or methyloxime and $R_1$, $R_2$ and X have the above definitions with a dehydration agent capable of freeing the ketone group to form a compound of the formula

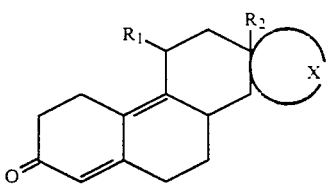

The process of the invention is particularly useful for forming products of formula I' wherein X form a pentagonal ring of the formula

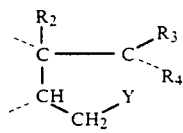

wherein $R_2$, $R_3$, $R_4$, Y and the dotted line in the 16,17-position have the above definition.

In a preferred mode of the process of the invention, the dehydration agent capable of freeing the ketone group is a sulfonic acid resin in the acid form such as a commercial sulfonic acid resin based on polystyrene or a styrene-divinylbenzene polymer but equally useful are inorganic acids such as sulfuric acid or hydrochloric acid in a lower alkanol or perchloric acid in acetic acid or a sulfonic acid such as p-toluene sulfonic acid.

It goes without saying that when one of $R_3$ or $R_4$ in the compounds of formula II obtained above is —OH, the compounds of formula II may be reacted with an etherification agent or an esterification agent which is one of those discussed above. When $R_3$ or $R_4$ is a 17-acyloxy, the compound may be optionally saponified with a saponification agent such as a base like sodium hydroxide, potassium hydroxide, potassium amide or potassium tert.-butylate and the reaction is preferably effected in a lower alkanol such as ethanol or methanol but equally useful is lithium acetylide in ethylenediamine.

Another object of the invention is a process for the preparation of the compounds of formula B wherein a compound of the formula

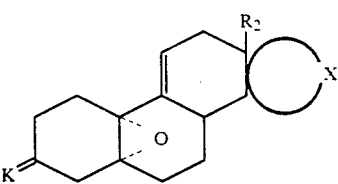

is reacted with a compound selected from the group consisting of $LiCu(R_1)_2$, $LiR_1$ and $R_1Mg\,Hal$ wherein $R_1$ has the above definition and Hal is halogen in the presence of a cuprous halide. In a preferred mode of the said process, the reaction is effected at room temperature and the reactant is $R_1Mg\,Hal$ in the presence of a cuprous salt.

Another object of the invention is a process for the preparation of a compound of the formula

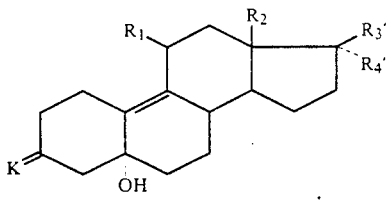

wherein $R_1$, $R_2$ and K have the above definitions, $R_3'$ is selected from the group consisting of —OH and $OR_c$, $R_c$ is the residue $AlK_4$ of an ether group or $COAlK_5$ of an ester group and $R_4'$ is hydrogen or alkenyl or alkynyl of 2 to 8 carbon atoms comprising reacting a compound of the formula

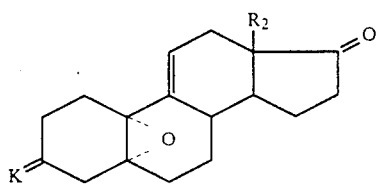

with a compound selected from the group consisting of $LiCu(R_1)_2$, $R_1Li$ and $R_1Mg\ Hal$ in the presence of a cuprous halide to obtain a compound of the formula

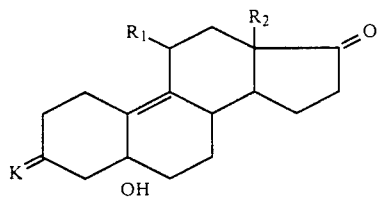

and either reducing the latter to obtain the corresponding 17-ol compound or with an appropriate magnesium to obtain the corresponding 17α-substituted-17β-ol steroid or with an organometallic derivative such as a lithium or potassium derivative to obtain the corresponding 17α-substituted-17β-ol steroid or with a cyanuration agent to obtain the corresponding 17α-ol-17β-cyano steroid, protecting the hydroxy group and reacting the latter with an organometallic compound as discussed above to obtain the corresponding 17α-substituted-17β-ol steroid and in the case of one of the compounds obtained is 17-hydroxylated, reacting it with an etherification agent or esterification agent and in the case when one of the compounds contains a 17 substituent with a triple bond reacting the latter with a reducing agent to obtain the corresponding ethylenic derivative.

In a preferred mode of the latter process, the reaction of the compound of formula A' with a compound of the group consisting of $R_1Li$, $LiCu(R_1)_2$ or $R_1Mg\ Hal$ is effected under the previously described conditions. The different reactants for reaction with the compounds of formula B" are known in steroid chemistry and are illustrated in the specific examples.

The novel intermediates of the invention are the compounds of formula B and B". Particularly preferred compounds of the invention are 3,3-[1,2-ethanediyl bisoxy]-11β-[4-trimethylsilyl-phenyl]-17α-(prop-1-ynyl)-$\Delta^9$-estrene-5α,17β-diol, 3,3-[1,2-ethanediyl-bisoxy]-11β-(4-pyridyl)-17α-(prop-1-ynyl)-$\Delta^9$-estrene-5α,17β-diol, 3,3-[1,2-ethanediyl-bisoxy]-11β-[3-(N,N-dimethylamino)-propyl]-17α-(prop-1-ynyl)-$\Delta^9$-estrene-5α,17β-diol, 3,3-[1,2-ethanediyl-bisoxy]-11β-[4-(N,N-dimethylamino)-phenyl]-17α-(prop-1-ynyl)-$\Delta^9$-estrene-5α,17β-diol, 3,3-[1,2-ethanediyl-bisoxy]-11β-[4-(N,N,-dimethylaminoethoxy)phenyl]-17α-(prop-1-ynyl)-$\Delta^9$-estrene-5α,17β-diol, 3,3-[1,2-ethanediyl-bisoxy]-11β-[4-(N,N-dimethylamino)-phenyl]-21-chloro-19-nor-17α-$\Delta^9$pregnene-20-yne-5α,17β-diol and 3,3-[1,2-ethanediyl-bisoxy]-11β-[4-(N,N-dimethylamino)-phenyl]-17α-(prop-2-ynyl)-$\Delta^9$-estrene-5α,17β-diol.

The novel antiglucocorticoid compositions of the invention are comprised of an antiglucocorticoidally effective amount of at least one compound of formula I and its non-toxic, pharmaceutically acceptable acid addition salts and an inert pharmaceutical carrier. The compositions may be in the form of tablets, dragees, gelules, granules, suppositories, ovules, injectable solutions or suspensions, pommades, creams and gels prepared in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful to principally counter effect secondary effects of glucocorticoids and are useful for the treatment of troubles due to a hypersecretion of glucocorticoids, especially against aging in general and especially against hypertension, atherosclerosis, osteoporosis, diabetics, obesity as well as immuno-suppressive effects and insomnia.

The study of the products on hormonal receptors shows that they possess progestomimetic or antiprogestomimetic activity or androgen or antiandrogen activity. The compounds of formula I which possess antiprogestomimetic activity are useful as original contraceptives or as interruption of pregnancy agents. They may also be useful for inducing regular cycles in females and more generally in warm-blooded females.

The products may be administered during periods or when progesterone discharges an essential physiological role which is notably during the luteal phase of the cycle at the moment of nidation or implantation of the embryo and during the pregnancy. One method of contraception of the invention consists of administering to the female at least one of the products of formula I or its salts 1 to 5 days before the end of the cycle. The products are preferably administered orally or in the vagina but may also be administered parenterally or endonasally.

The compounds of formula I possessing antiprogestomimetic activity are equally useful against hormonal irregularities and by other means they present an interest in the treatment of hormonodependent tumors. Their action against hypophysial secretions make the compounds useful in menopause.

The compounds are equally useful for the synchronization of estrus in larger animals such as bovines and sheep and are useful for controlling the fertility of household pets such as cats and dogs.

Certain compounds of formula I also present progestomimetic properties and are useful for the treatment of amenorrhea, of dysmenorrhea and luteal insufficiencies.

The compounds of formula I possessing antiandrogenic activity are useful in the treatment of hypertrophies and prostate cancer, of hyperandrogenia, of anemia, hirsutism and of acne as well as male contraception.

Certain of the compounds of formula I possess estrogenic properties and are useful for the treatment of troubles due to a hypofolliculinia such as amenorrhea, dysmenorrhea, repeated abortions, premenstrual troubles as well as for the treatment of menopause.

Certain of the compounds of formula I possess antiestrogenic properties and are useful for the treatment of mammalogy carcinoma and its meta stases.

Among the preferred compositions of the invention ae those wherein the active ingredient is selected from the group consisting of 2,2-dimethyl-11$\beta$-(4-dimethylaminophenyl)-17$\alpha$-(prop-1-ynyl)-$\Delta^{4,9}$-estradiene-17$\beta$-ol-3-one, 2,2-dicyano-11$\beta$-(4-dimethylaminophenyl)-17$\alpha$-(prop-1-ynyl)-$\Delta^{4,9}$-estradiene-17$\beta$-ol-3-one, 2$\alpha$-methyl-11$\beta$-(4-dimethylaminophenyl)-17$\alpha$-(prop-1-ynyl)-$\Delta^{4,9}$-estradiene-17$\beta$-ol-3-one, 2$\beta$-methyl-11$\beta$-(4-dimethylaminophenyl)-17$\alpha$-(prop-1-ynyl)-$\Delta^{4,9}$-estradiene-17$\beta$-ol-3-one, 2-cyano-11$\beta$-(4-dimethylaminophenyl)-17$\alpha$-(prop-1-ynyl)-$\Delta^{4,9}$-estradiene-17$\beta$-ol-3-one, 11$\beta$-(4-dimethylamino)-17$\alpha$-(prop-1-ynyl)-$\Delta^{1,3,5(10)}$-estratriene-3,17$\beta$-diol, 11$\beta$-(4-dimethylaminophenyl)-17$\beta$-acetoxy-17$\alpha$-(prop-1-ynyl)-$\Delta^{1,3,5(10)}$-estratriene-3-ol, 3-methoxy-11$\beta$-(4-dimethylaminophenyl)-17$\alpha$-(prop-1-ynyl)-$\Delta^{1,3,5(10)}$-estratriene-17$\beta$-ol, 3-methoxy-11$\beta$-(4-dimethylaminophenyl)-17$\beta$-acetoxy-17$\alpha$-(prop-1-ynyl)-$\Delta^{1,3,5(10)}$-estratriene, 11$\beta$-(3-methoxyphenyl)-17$\alpha$-(prop-1-ynyl)-$\Delta^{5(10)}$-estrene-17$\beta$-ol-3-one,(E) 11$\beta$-(3-methoxyphenyl)-17$\alpha$-(prop-1-enyl)-$\Delta^{5(10)}$-estrene-17$\beta$-ol-3-one, 11$\beta$-(4-dimethylaminophenyl)-17$\alpha$-(prop-1-ynyl)-$\Delta^{5(10)}$-estrene-17$\beta$-ol-3-one, 2-(acetyloxymethylene)-11$\beta$-(4-dimethylaminophenyl)-17$\alpha$-(prop-1-ynyl)-$\Delta^{4,9}$-estradiene-17$\beta$-ol-3-one, 2-(4-morpholinomethylene)-11$\beta$-(4-dimethylaminophenyl)-17$\alpha$-(prop-1-ynyl)-$\Delta^{4,9}$-estradiene-17$\beta$-ol-3-one, 11$\beta$-(4-dimethylaminophenyl)-17$\alpha$-(prop-1-ynyl)-isoxazolo[4,5-b]-$\Delta^{4,9}$-estradiene-17$\beta$-ol, 11$\beta$-[4-(2-dimethylaminoethoxy)-phenyl]-$\Delta^{1,3,5(10)}$-estratriene-3,17$\beta$-diol, 11$\beta$-[4-(2-dimethylaminoethoxy)-phenyl]-$\Delta^{1,3,5(10)}$-estratriene-17$\beta$-ol, 3-(2-dimethylaminoethoxy)-11$\beta$-phenyl-$\Delta^{1,3,5(10)}$-estratriene-17$\beta$-ol 11$\beta$-(4-pyridyl)-17$\alpha$-(prop-1-ynyl-$\Delta^{4,9}$-estradiene-17$\beta$-ol-3-one, 11$\beta$-[4-(N,N-dimethylaminoethoxy)-phenyl[-17$\alpha$-(prop-1-ynyl)-$\Delta^{4,9}$-estradiene-17$\beta$-ol-3-one, 11$\beta$-[4-(N,N-dimethylamino)-phenyl]-17$\alpha$-(prop-1-ynyl)-$\Delta^{4,9}$-estradiene-17$\beta$-ol-3-one, 11$\beta$-[4-(N,N-dimethylamino)-phenyl]-23-methyl-19,21-dinor-17$\alpha$-$\Delta^{4,9,23}$ cholatriene-20-yn-17$\beta$-ol-3-one, 11$\beta$-[4-(N,N-dimethylamino)-phenyl]-21-chloro-19-nor-17$\alpha$-$\Delta^{4,9}$-pregnadiene-20-yne-17$\beta$-ol-3-one, N-oxide of 11$\beta$-[4-(N,N-dimethylamino)-phenyl]-21-chloro-19-nor-17$\alpha$-$\Delta^{4,9}$-pregnadiene-20-yne-17$\beta$-ol-3-one, N-oxide of 9$\alpha$,10$\alpha$-epoxy-11$\beta$-[4-(N,N-dimethylamino)-phenyl]-21-chloro-19-nor-17$\alpha$-$\Delta^{4}$-pregnene-20-yne-17$\beta$-ol-3-one, 11$\beta$-[4-(N,N-dimethylamino)-phenyl]-21-phenyl-19-nor-17$\alpha$-$\Delta^{4,9}$-pregnadiene-20-yne-17$\beta$-ol-3-one, 11$\beta$-[4-(N,N-dimethylamino)-phenyl]-17$\alpha$-(prop-2-ynyl)-$\Delta^{4,9}$-estradiene-17$\beta$-ol-3one, 11$\beta$-[4-(N,N-dimethylamino)-phenyl]-17$\alpha$-ethynyl-$\Delta^{4,9}$-estradiene 17$\beta$-ol-3-one, N-oxide of 11$\beta$-[4-(N,N-dimethylamino)-phenyl]-17$\alpha$-(prop-1-ynyl)-$\Delta^{4,9}$-estradiene-17$\beta$-ol-3-one, 11$\beta$-[4-(N,N-dimethylamino)-phenyl]-17$\alpha$-(prop-2-enyl)-$\Delta^{4,9}$-estradiene-17$\beta$-ol-3-one, 11$\beta$-[4-(N,N-dimethylaminoethylthio)-phenyl]-17$\alpha$-(prop-1-ynyl)-$\Delta^{4,9}$-estradiene-17$\beta$-ol-3-one, 11$\beta$-[4-(N,N-dimethylamino)-phenyl]-21-trimethylsilyl-19-nor-17$\alpha$-$\Delta^{4,9}$-pregnadiene-20-yne-17$\beta$-ol-3-one, $\gamma$-lactone of 11$\beta$-(4-dimethylaminophenyl)-19-nor-17$\alpha$-$\Delta^{1,3,5(10)}$-pregnatriene-3,17$\beta$-diol-21-carboxylic acid, $\gamma$-lactone of 3-methoxy-11$\beta$-(4-dimethylamino-phenyl)-19-nor-17$\alpha$-$\Delta^{1,3,5(10)}$-pregnatriene-17$\beta$-ol-21-carboxylic acid, $\gamma$-lactone of 11$\beta$-(4-dimethylamino-phenyl)-19-nor-17$\alpha$-$\Delta^{5(10)}$-pregnene-17$\beta$-ol-3-one-21-carboxylic acid, $\gamma$-lactone of 2$\alpha$-methyl 11$\beta$-(4-dimethylamino-phenyl)-19-nor-17$\alpha$-$\Delta^{4,9}$-pregnadiene-17$\beta$-ol-3-one-21-carboxylic acid, $\gamma$-lactone of 2$\beta$-methyl 11$\beta$-(4-dimethylamino-phenyl)-19-nor-17$\alpha$-$\Delta^{4,9}$-pregnadiene-17$\beta$-ol-3-one-21-carboxylic acid, $\gamma$-lactone of 2,2-dimethyl 11$\beta$-(4-dimethylamino-phenyl)-19-nor-17$\alpha$-$\Delta^{4,9}$-pregnadiene-17$\beta$-ol-3one-21-carboxylic acid, $\gamma$-lactone of 11$\beta$-[4(N-methyl N-ethyl) amino-phenyl]-19-nor-17$\alpha$-$\Delta^{5(10)}$-pregnene-17$\beta$-ol-3-one-21-carboxylic acid, and their non-toxic, pharmaceutically acceptable acid addition salts.

The novel method of the invention for inducing antiglucocorticoid activity in warm-blooded animals, including humans, comprises administering to warm-blooded animals an antiglucocorticoidally effective amount of at least one compound of formula I and their non-toxic, pharmaceutically acceptable acid addition salts. The compounds may be administered orally. rectally, parenterally or topically and the usual daily dose is 0.15 to 0.150 mg/kg depending upon the compound, the condition treated and the method of treatment.

The antiprogestomimetic compositions of the invention contain a physiologically active quantity of at least one product of formula I and its pharmaceutically acceptable acid addition salts as antiprogestomimetics.

These compositions may be adminstered via the digestive tract, parenterally or locally, particularly in the vagina or via the endonasal route. They may be in the form of a simple tablet or lozenges, gelatin capsules, granulated, suppositories, ovules, injectable preparations, ointments, creams or gels which are prepared according to the usual methods.

Excipients which may be employed are talc, gum arabic, lactose starch, magnesium stearate, cocoa butter, animal and vegetable fats, paraffin derivatives, glycols, various wetting agents, dispersants, emulsifiers and preservatives.

The antiprogestomimetic compositions of the invention have remarkable properties as may be seen in the pharmacological tests which are described later.

The antiprogestomimetic compositions of the invention are used essentially to induce menses in female warm blooded animals.

The induction of menses during the luteal phase of the cycle and particularly at the end of the luteal phase permits the use of the compositions of the invention as contraceptives.

The antiprogrestomimetic compositions according to the invention may be equally used as agents to interrupt pregnancy since experiments with animals have demonstrated them to be abortive at any period of gestation.

The new method of the invention consists of inducing the menses in warm blooded female animals including women and is characterised in that one administers a quantity of antiprogestomimetic compound which is physiologically active such as a product of formula I.

But it is understood that the essential role of progesterone is assigned during the luteal phase of the cycle at the moment of implantation of the embryo and during pregnancy.

The use of an antiprogestomimetic as an inducer of menstruation has been proposed, for example, in the tenth World Health Organization report page 80 and later in Chemtech, September 1977 page 566.

The method of utilization of this product is equally suggested as "post-coital and once-a-month drugs" in the report in WHO and in the expression "when taken monthly... will induce menstruation" in the Chemtech article.

Meanwhile before the products of formula I, no product having the required pharmacological properties for such a utilization had been synthesized.

The method of contraception according to the invention consists of administring to the woman about 10 mg to 1 gram of the product for 1 to 5 days preferably at the end of the menstrual cycle. Preferably one takes about 25 to 200 mg of the product per day.

Preferably the product is adminstered orally. Administration of the product via the vagina is equally suitable.

The method of using the products of the invention to interrupt pregnancy consists in administering to warm blooded females at least a physiolgically active amount of the product of formula I.

One administers an amount on the order of about 50 mg to 1 gram per day of the product for 1 to 5 days toward the end of the menstrual cycle. Preferably 200 mg to about 500 mg is used in women.

The preferred manner of administration of this product is orally or via the vagina.

The products of formula I can be used in synchronizing the fertile periods of animals particularly cattle and sheep. They can alsobe used to control the fertility of pets like dogs or cats.

Finally, the products of formula I, which have anti-androgen activity can be used for human contraception.

The compounds of formula A and especially of formula A' used to prepare the compounds of formula B or B" are generally known compounds which can be prepared by reacting the corresponding $\Delta^{5(10),9(11)}$ steroids with an epoxidation agent selective for the 5(10) double bond, for example with hydrogen peroxide in the presence of hexachloroacetone or hexafluoroacetone as described in French patent No. 2,423,486. The new compound, 3,3-[1,2-ethanediyl-bisoxy]-17α-(prop-1-yny)-5α,10α-epoxy-$\Delta^{9(11)}$-estrene-17β-ol is prepared in the Example.

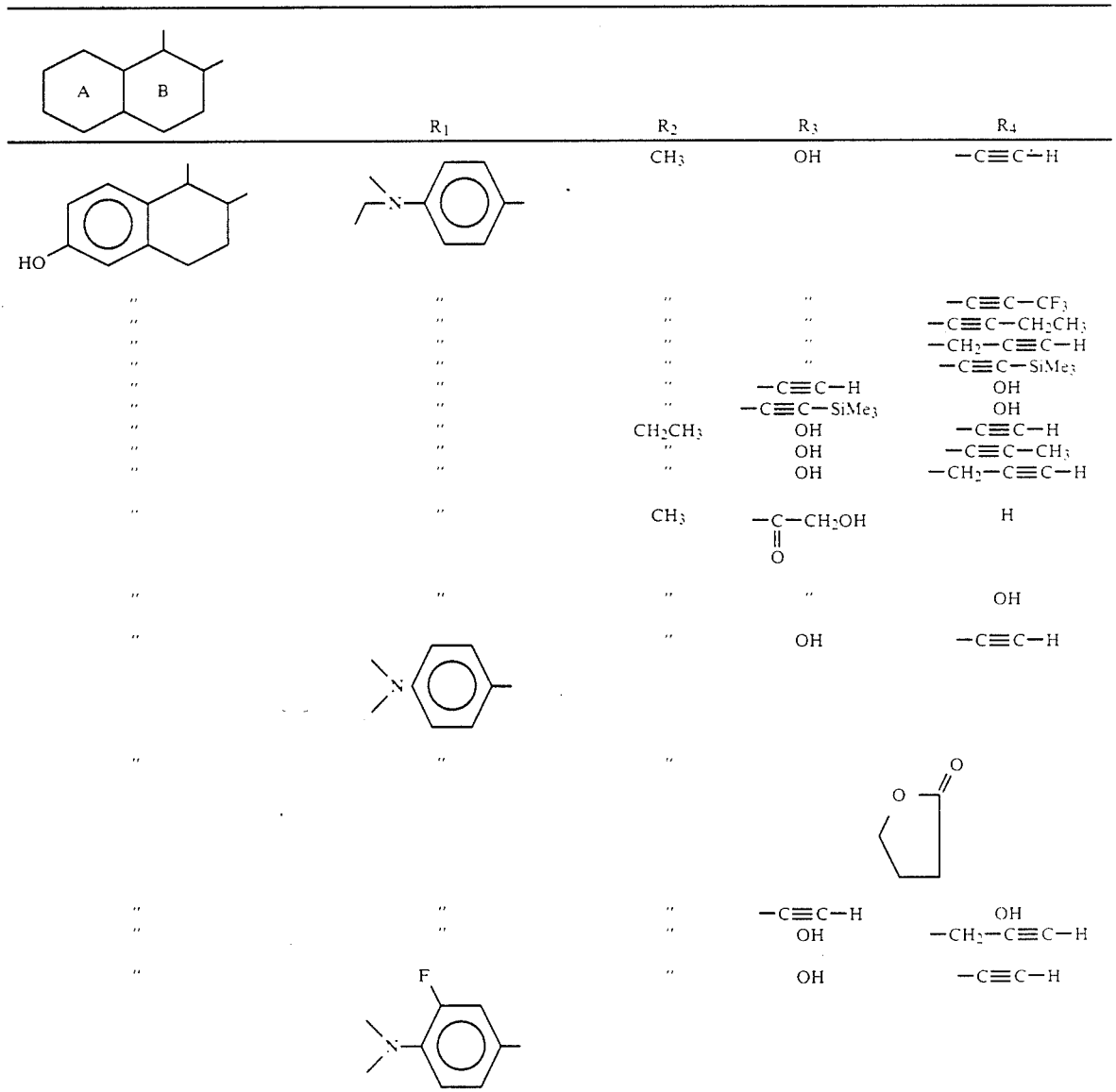

| | | | | |
|---|---|---|---|---|
| " | " | " | " | —C≡C—CH₃ |
| " | " | " | " | —CH₂—C≡C—H |
| " | " | " | —C≡C—H | OH |
| " | " | 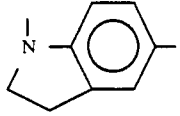 | OH | —C≡C—H |
| " | " | " | " | —C≡C—CF₃ |
| " | " | " | " | —CH₂—C≡C—H |
| " | " | " | " | —C≡C—CH₂CH₃ |
| " | " | " | " | —C≡C—Cl |
| " | " | " | " | —C≡C—SiMe₃ |
| " | " | " | —C≡C—H | OH |
| " | " | " | —C≡C—SiMe₃ | OH |
|  | 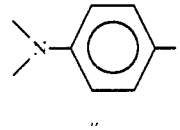 | CH₃ | OH | —C≡C—H |
| " | " | " | " | —C≡C—CF₃ |
| " | " | " | " | —C≡C—CH₂CH₃ |
| " | " | " | " | —CH₂—C≡C—H |
| " | " | " | " | —C≡C—SiMe₃ |
| " | " | " | —C≡C—H | OH |
| " | " | " | —C≡C—SiMe₃ | OH |
| " | " | CH₂CH₃ | OH | —C≡C—H |
| " | " | " | OH | —C≡C—CH₃ |
| " | " | " | OH | —CH₂—C≡C—H |
| " | " | CH₃ | —C(=O)—CH₂OH | H |
| " | " | " | " | OH |
| " | 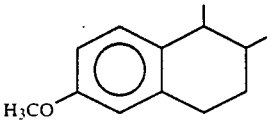 | " | OH | —C≡C—H |
| " | " | " | " | 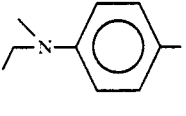 |
| " | " | " | —C≡C—H | OH |
| " | " | " | OH | —CH₂—C≡C—H |
| " | 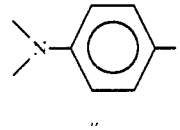 | " | OH | —C≡C—H |
| " | " | " | " | —C≡C—CH₃ |
| " | " | " | " | —CH₂—C≡C—H |
| " | " | " | —C≡C—H | OH |
| " | 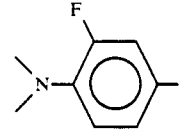 | " | OH | —C≡C—H |
| " | " | " | " | —C≡C—CF₃ |
| " | " | " | " | —CH₂—C≡C—H |
| " | " | " | " | —C≡C—CH₂CH₃ |
| " | " | " | " | —C≡C—Cl |
| " | " | " | " | —C≡C—SiMe₃ |

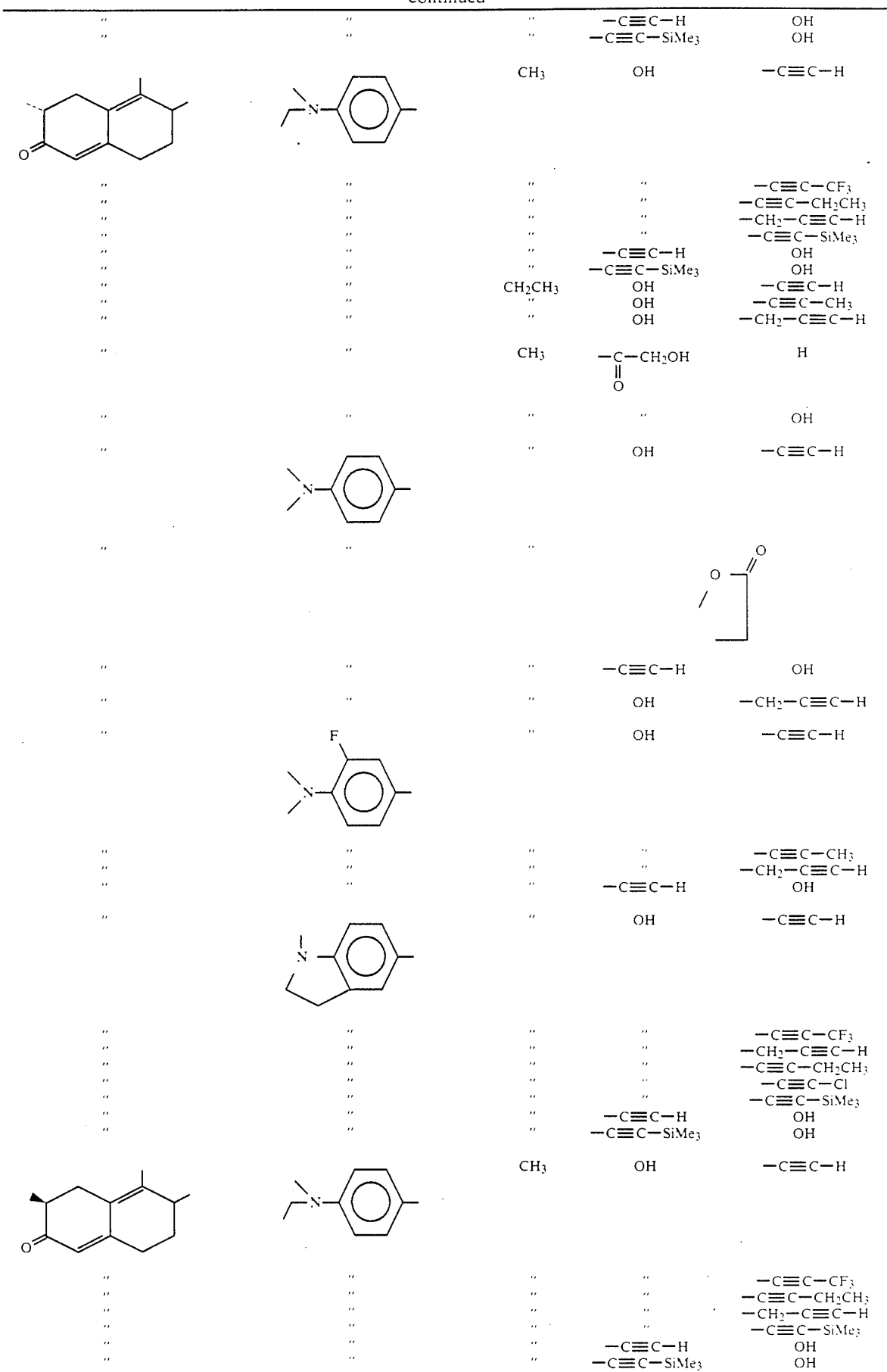

-continued

| Col 1 | Col 2 | Col 3 | Col 4 | Col 5 |
|---|---|---|---|---|
| " | " | CH₂CH₃ | OH | —C≡C—H |
| " | " | " | OH | —C≡C—CH₃ |
| " | " | " | OH | —CH₂—C≡C—H |
| " | " | CH₃ | —C(=O)—CH₂OH | H |
| " | " | " | " | OH |
| " | 4-(N,N-dimethylamino)phenyl | " | OH | —C≡C—H |
| " | " | " | (acetate/ester group) | |
| " | " | " | —C≡C—H | OH |
| " | " | " | OH | —CH₂—C≡C—H |
| " | 2-fluoro-4-(N,N-dimethylamino)phenyl | " | OH | —C≡C—H |
| " | " | " | " | —C≡C—CH₃ |
| " | " | " | " | —CH₂—C≡C—H |
| " | " | " | —C≡C—H | OH |
| " | indolinyl | " | OH | —C≡C—H |
| " | " | " | " | —C≡C—CF₃ |
| " | " | " | " | —CH₂—C≡C—H |
| " | " | " | " | —C≡C—CH₂CH₃ |
| " | " | " | " | —C≡C—Cl |
| " | " | " | " | —C≡C—SiMe₃ |
| " | " | " | —C≡C—H | OH |
| " | " | " | —C≡C—SiMe₃ | OH |
| 6-hydroxy-1,2-dimethyl-tetrahydronaphthyl | indolinyl | CH₂CH₃ | OH | —C≡C—H |
| " | " | " | " | —C≡C—CH₃ |
| " | " | " | " | —CH₂—C≡C—H |
| " | " | CH₃ | —C(=O)—CH₂OH | —H |
| " | " | " | " | —OH |
| " | " | " | —C(=O)—CH₃ | —H |
| " | " | " | —OH | —C≡C—H |
| 6-oxo-1,2-dimethyl-octahydronaphthyl | 4-(N,N-dimethylamino)phenyl | | | |

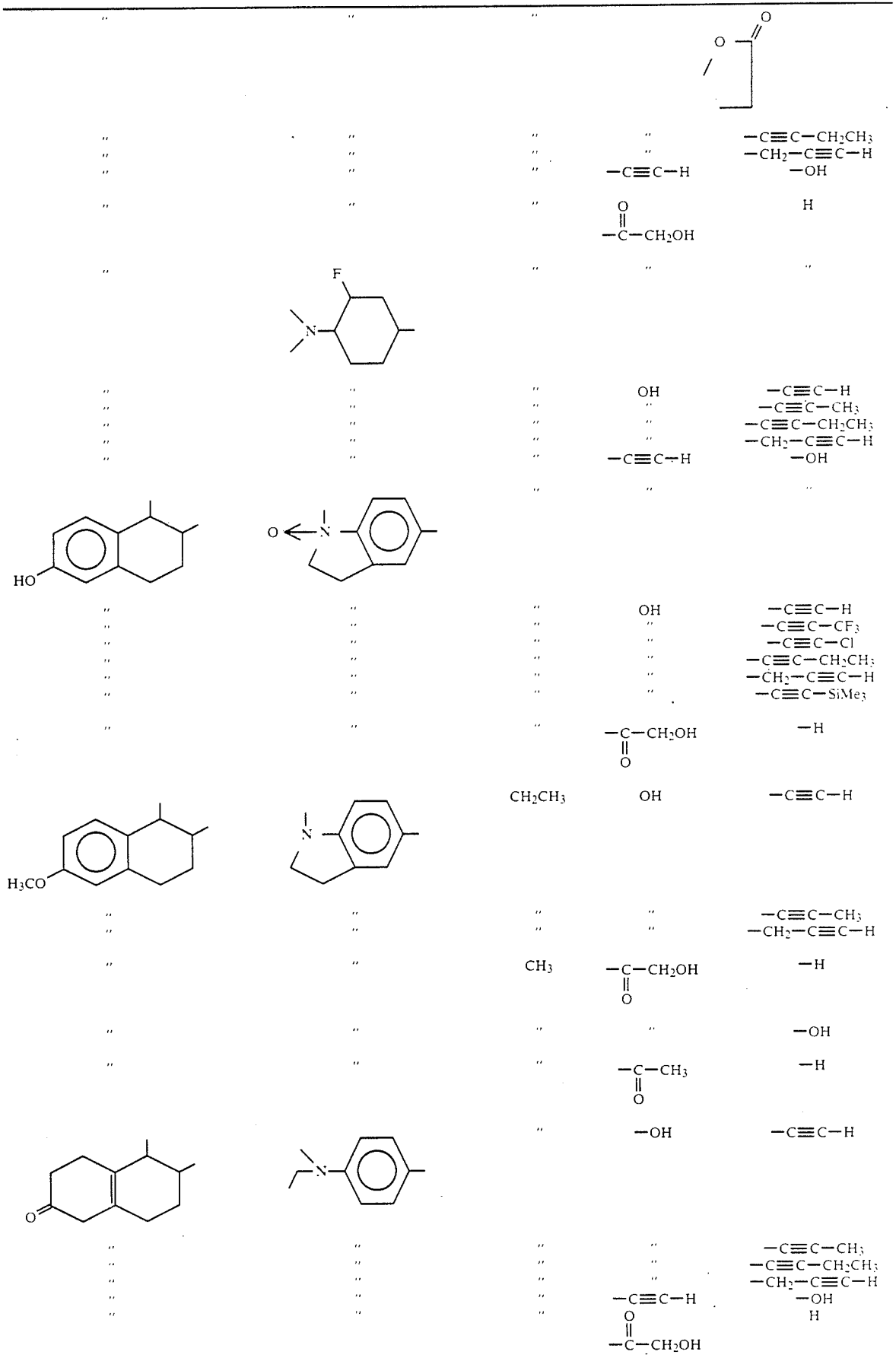

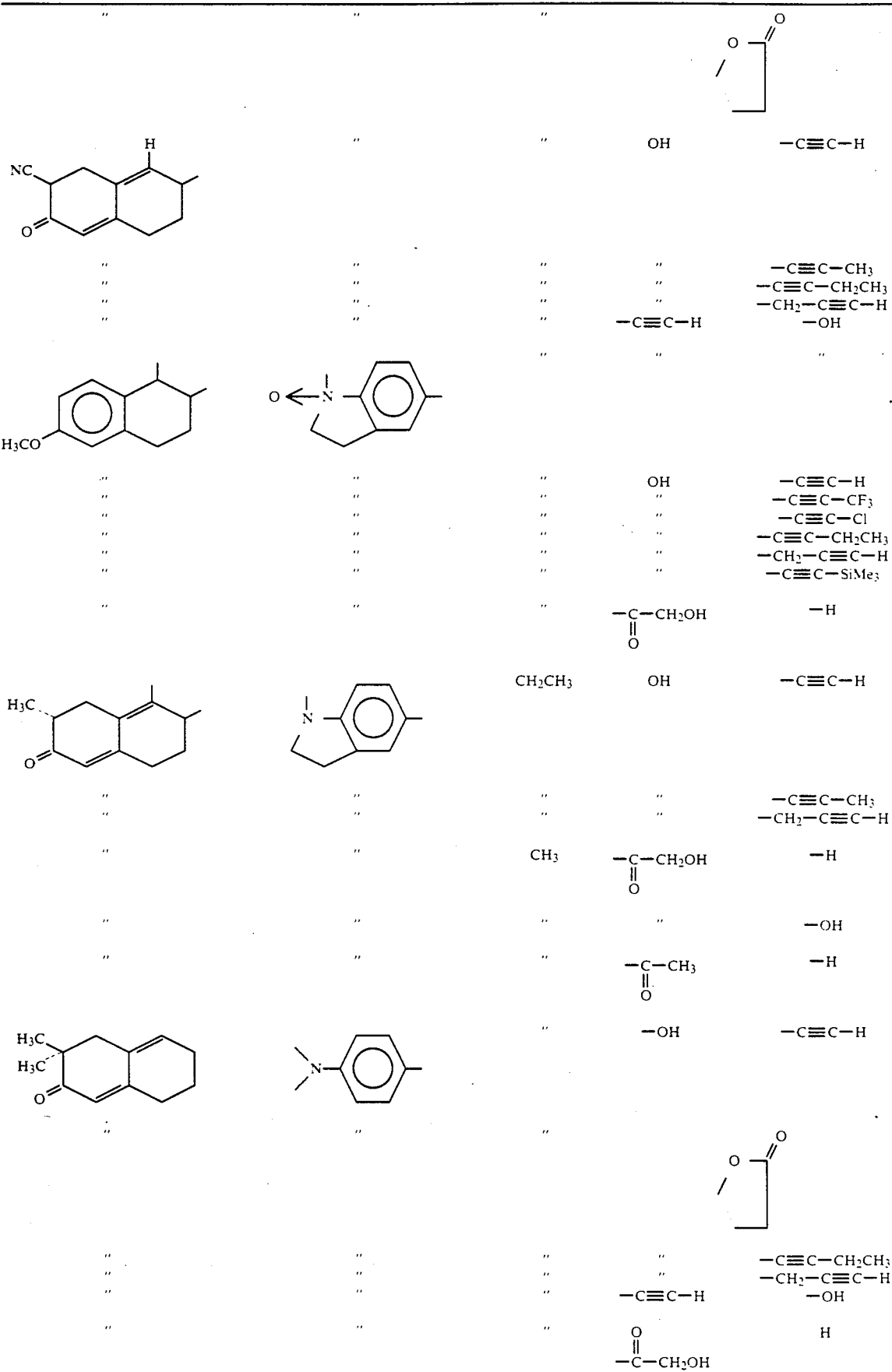

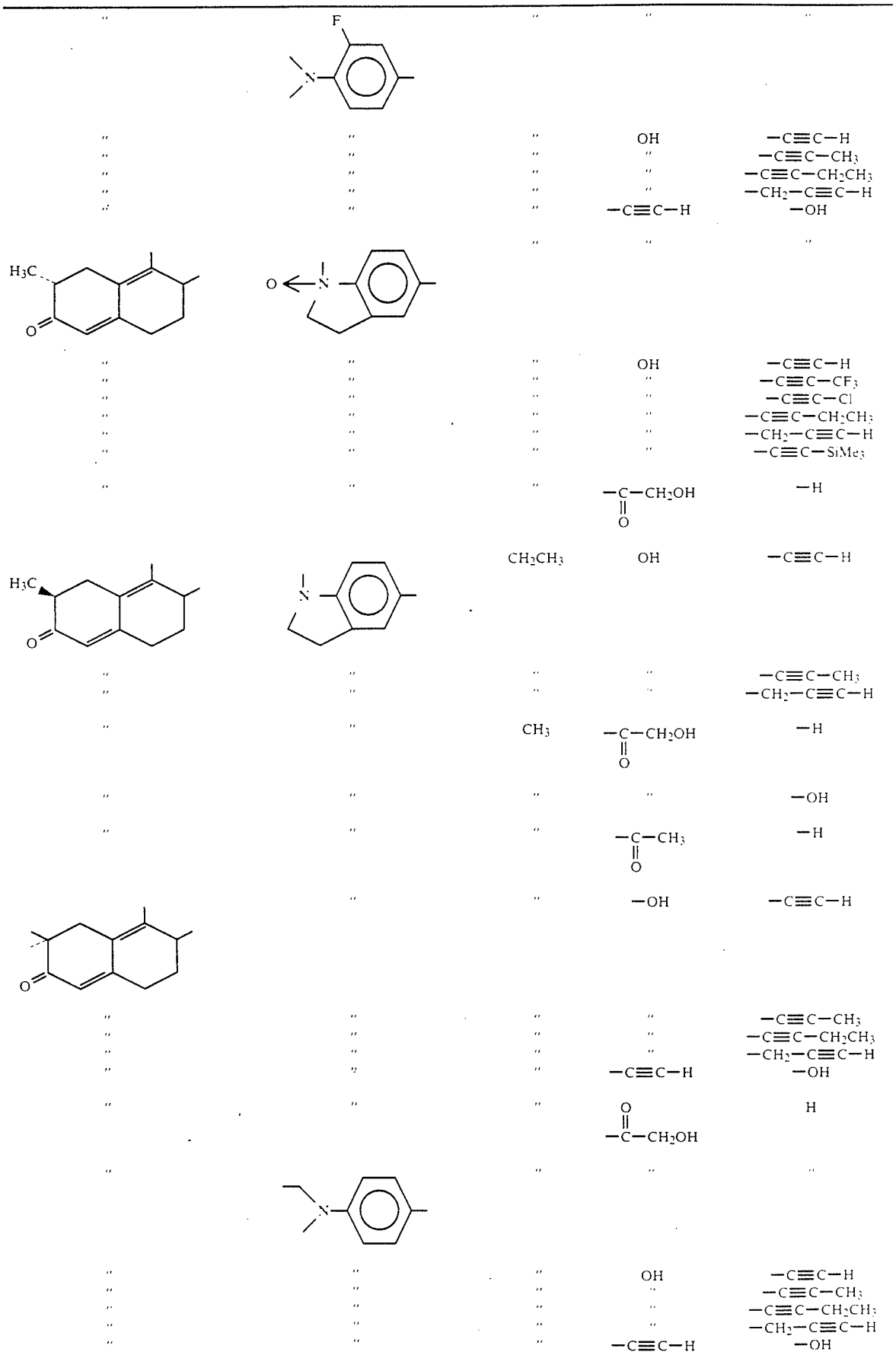

-continued

| | | | | |
|---|---|---|---|---|
| ![structure: methyl-dimethyl-octahydronaphthalenone] | ![indoline N-oxide with methyl] | " | " | " |
| " | " | " | OH | —C≡C—H |
| " | " | " | " | —C≡C—CF₃ |
| " | " | " | " | —C≡C—Cl |
| " | " | " | " | —C≡C—CH₂CH₃ |
| " | " | " | " | —CH₂—C≡C—H |
| " | " | " | " | —C≡C—SiMe₃ |
| " | " | " | —C(=O)—CH₂OH | —H |
| ![6-hydroxy-1,2-dimethyltetralin] | ![H₃CS-phenyl] | CH₃ | OH | —C≡C—H |
| " | " | " | " | —C≡C—CH₃ |
| " | " | " | " | —CH₂—C≡C—H |
| " | " | " | —C≡C—H | —OH |
| " | ![EtS-phenyl] | " | " | " |
| " | " | " | OH | —C≡C—H |
| " | " | " | " | —C≡C—CH₃ |
| " | " | " | " | —CH₂—C≡C—H |
| " | " | " | " | —C≡C—CH₂CH₃ |
| " | ![N-phenyl] | " | " | |
| " | " | " | " | —C≡C—CF₃ |
| " | " | " | —C≡C—SiMe₃ | —OH |
| " | " | " | —C(=O)—CH₂OH | —H |
| " | " | " | " | —OH |
| " | " | " | —C(=O)—CH₃ | —H |
| " | " | CH₂CH₃ | OH | —C≡C—H |
| " | " | " | " | —C≡C—CH₃ |
| " | " | " | " | —C≡C—Cl |
| " | " | " | " | —C≡C—CH₂—CH₃ |
| " | " | " | " | —C≡C—SiMe₃ |
| " | " | " | " | —CH₂—C≡C—H |
| " | " | " | —C(=O)—CH₂OH | —H |
| " | ![H₃CS-phenyl] | CH₃ | —C≡C—H | —OH |
| " | " | " | —C(=O)—CH₂OH | —H |
| " | " | " | OH | —CH₂—C≡C—H |

-continued

| | | | | |
|---|---|---|---|---|
| " | 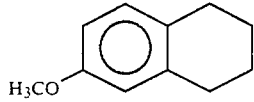 | " | " | " |
| 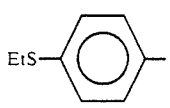 | 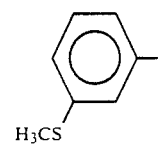 | $CH_3$ | OH | $-C\equiv C-H$ |
| " | " | " | " | $-C\equiv C-CH_3$ |
| " | " | " | | $-CH_2-C\equiv C-H$ |
| " | " | " | $-C\equiv C-H$ | $-OH$ |
| " | " | " | " | " |
| " | 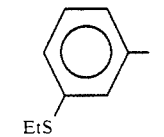 | " | | |
| " | " | " | OH | $-C\equiv C-H$ |
| " | " | " | " | $-C\equiv C-CH_3$ |
| " | " | " | " | $-CH_2-C\equiv C-H$ |
| " | " | " | " | $-C\equiv C-CH_2CH_3$ |
| " | 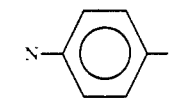 | " | | |
| " | " | " | $-C\equiv C-SiMe_3$ | $-C\equiv C-CF_3$ |
| " | " | " | | $-OH$ |
| " | " | " | $-\underset{\underset{O}{\|}}{C}-CH_2OH$ | $-H$ |
| " | " | " | " | $-OH$ |
| " | " | " | $-\underset{\underset{O}{\|}}{C}-CH_3$ | $-H$ |
| " | " | $CH_2CH_3$ | OH | $-C\equiv C-H$ |
| " | " | " | " | $-C\equiv C-CH_3$ |
| " | " | " | " | $-C\equiv C-Cl$ |
| " | " | " | " | $-C\equiv C-CH_2-CH_3$ |
| " | " | " | " | $-C\equiv C-SiMe_3$ |
| " | " | " | " | $-CH_2-C\equiv C-H$ |
| " | " | " | $-\underset{\underset{O}{\|}}{\overset{O}{C}}-CH_2OH$ | $-H$ |
| " | 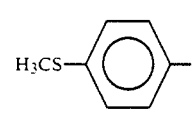 | $CH_3$ | $-C\equiv C-H$ | $-OH$ |
| " | " | " | $-\underset{\underset{O}{\|}}{C}-CH_2OH$ | $-H$ |
| " | " | " | OH | $-CH_2-C\equiv C-H$ |
| " | " | " | " | " |
| " | 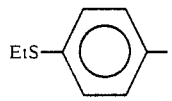 | | | |

| Structure A | Structure B | R1 | R2 | R3 |
|---|---|---|---|---|
| ![octahydronaphthalenone with H3C and methyl groups] | ![phenyl with H3CS meta] | CH₃ | OH | –C≡C–H |
| " | " | " | " | –C≡C–CH₃ |
| " | " | " | " | –CH₂–C≡C–H |
| " | " | " | –C≡C–H | –OH |
| " | ![phenyl with EtS meta] | " | " | " |
| " | " | " | OH | –C≡C–H |
| " | " | " | " | –C≡C–CH₃ |
| " | " | " | " | –CH₂–C≡C–H |
| " | ![phenyl with N(CH₃)₂ para] | " | " | –C≡C–CH₂CH₃ |
| " | " | " | " | –C≡C–CF₃ |
| " | " | " | –C≡C–SiMe₃ | –OH |
| " | " | " | –C(=O)–CH₂OH | –H |
| " | " | " | " | –OH |
| " | " | " | –C(=O)–CH₃ | –H |
| " | " | –CH₂CH₃ | OH | –C≡C–H |
| " | " | " | " | –C≡C–CH₃ |
| " | " | " | " | –C≡C–Cl |
| " | " | " | " | –C≡C–CH₂–CH₃ |
| " | " | " | " | –C≡C–SiMe₃ |
| " | " | " | " | –CH₂–C≡C–H |
| " | " | " | –C(=O)–CH₂OH | –H |
| " | ![phenyl with H3CS para] | CH₃ | –C≡C–H | –OH |
| " | " | " | –C(=O)–CH₂OH | –H |
| " | " | " | OH | –CH₂–C≡C–H |
| " | " | " | " | " |
| " | ![phenyl with EtS para] | | | |
| ![octahydronaphthalenone isomer with H3C and methyl] | ![phenyl with H3CS meta] | CH₃ | OH | –C≡C–H |
| " | " | " | " | –C≡C–CH₃ |
| " | " | " | " | –CH₂–C≡C–H |

-continued

| Col1 | Col2 | Col3 | Col4 | Col5 |
|---|---|---|---|---|
| " | " | " | —C≡C—H | —OH |
| " | (3-EtS-phenyl) | " | " | " |
| " | " | " | OH | —C≡C—H |
| " | " | " | " | —C≡C—CH₃ |
| " | " | " | " | —CH₂—C≡C—H |
| " | (4-NMe₂-phenyl) | " | " | —C≡C—CH₂CH₃ |
| " | " | " | " | —C≡C—CF₃ |
| " | " | " | —C≡C—SiMe₃ | —OH |
| " | " | " | —C(=O)—CH₂OH | —H |
| " | " | " | " | —OH |
| " | " | " | —C(=O)—CH₃ | —H |
| " | " | —CH₂CH₃ | OH | —C≡C—H |
| " | " | " | " | —C≡C—CH₃ |
| " | " | " | " | —C≡C—Cl |
| " | " | " | " | —C≡C—CH₂—CH₃ |
| " | " | " | " | —C≡C—SiMe₃ |
| " | " | " | " | —CH₂—C≡C—H |
| " | " | " | —C(=O)—CH₂OH | —H |
| " | (4-H₃CS-phenyl) | CH₃ | —C≡C—H | —OH |
| " | " | " | —C(=O)—CH₂OH | —H |
| " | " | " | OH | —CH₂—C≡C—H |
| " | " | " | " | " |
| " | (4-EtS-phenyl) | " | " | " |
| (octahydronaphthalen-2-one, dimethyl) | (4-NMe₂-phenyl) | CH₃ | —C≡C—H | —OH |
| " | " | " | —C(=O)—CH₂OH | —H |
| (6-HO-tetrahydronaphthalene, dimethyl) | (4-NMe₂(→O)-phenyl) | " | " | " |
| " | " | " | —C≡C—H | —OH |
| " | " | " | OH | —CH₂—C≡C—H |

-continued

| | | | | |
|---|---|---|---|---|
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| 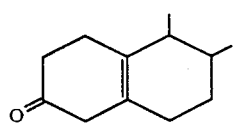 | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| 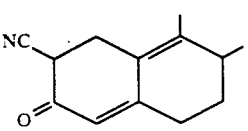 | " | " | " | " |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |
| 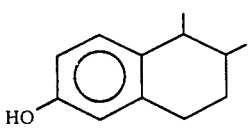 | 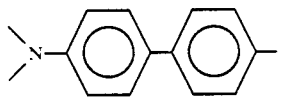 | " | OH | —C≡C—H |
| " | " | " | " | —C≡C—CF₃ |
| " | " | " | " | —C≡C—CH₃ |
| " | " | " | " | —C≡C—Cl |
| 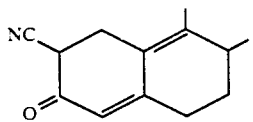 | 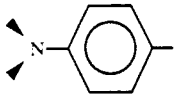 | CH₃ | —C≡C—H | —OH |
| " | " | " | —C(=O)—CH₂OH | —H |
| 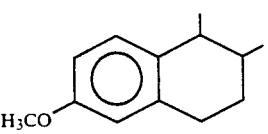 | 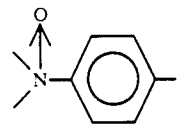 | " | " | " |
| " | " | " | —C≡C—H | —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| 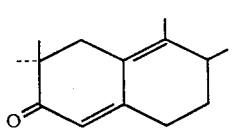 | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |

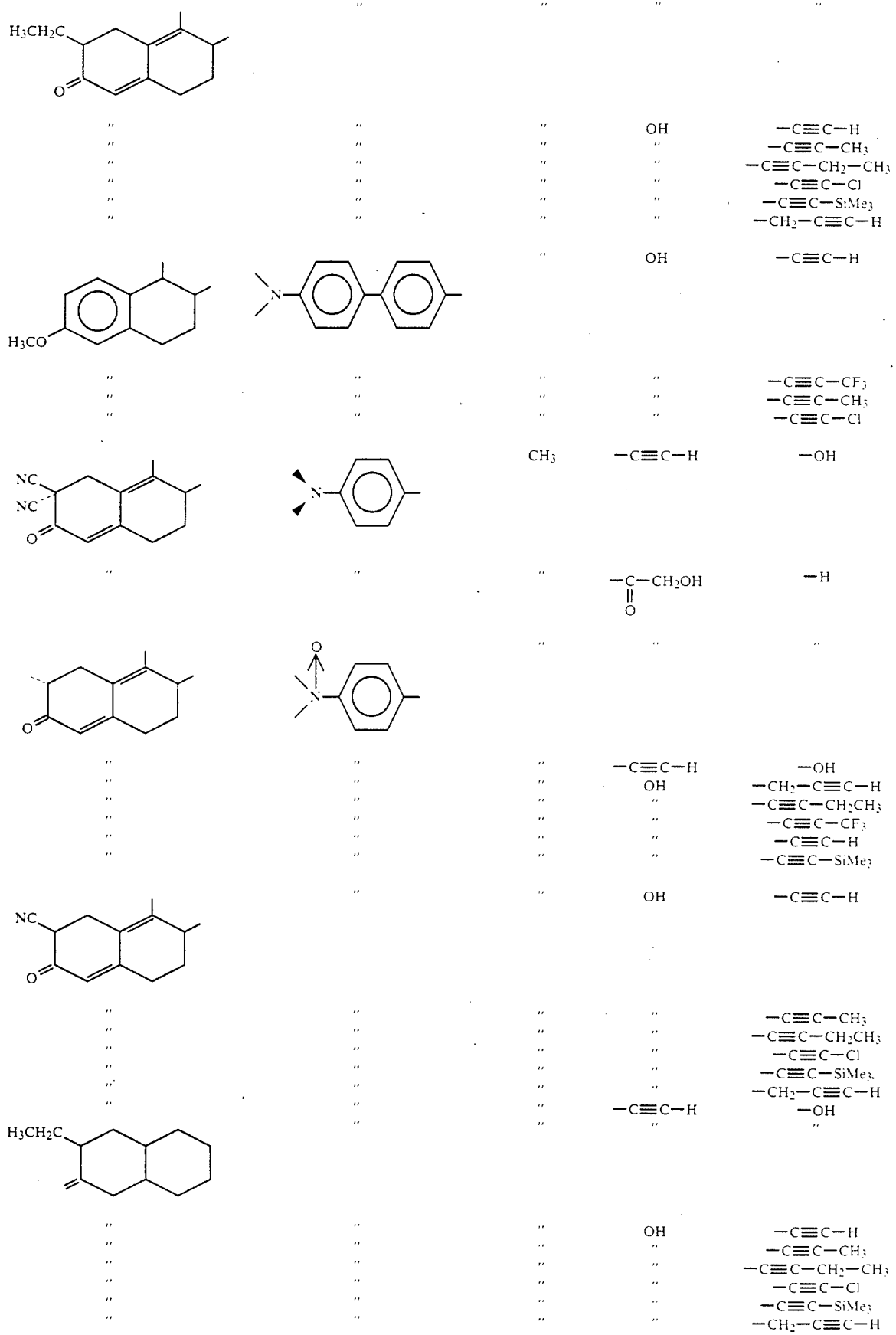

-continued

| Structure 1 | Structure 2 | | | |
|---|---|---|---|---|
| | | | OH | —C≡C—H |
| 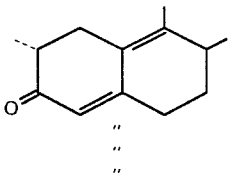 | 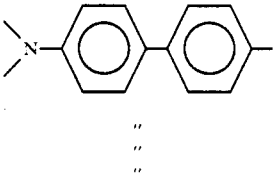 | | | |
| " | " | " | " | —C≡C—CF₃ |
| " | " | " | " | —C≡C—CH₃ |
| " | " | " | " | —C≡C—Cl |
| 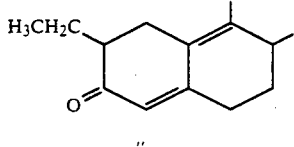 | 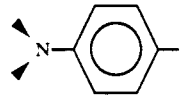 | CH₃ | —C≡C—H | —OH |
| " | " | " | —C—CH₂OH<br>‖<br>O | —H |
| 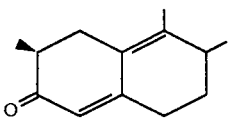 | 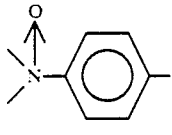 | " | " | " |
| " | " | " | —C≡C—H | —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| " | " | " | OH | —C≡C—H |
| 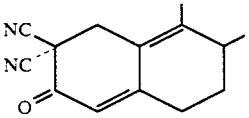 | " | | | |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| 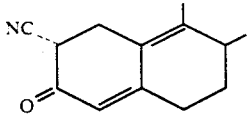 | " | | | |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |
| " | " | " | OH | —C≡C—H |
| 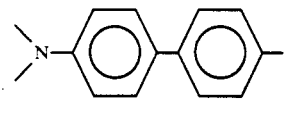 | 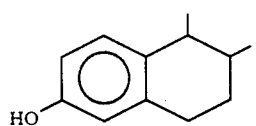 | | | |
| " | " | " | " | —C≡C—CF₃ |
| " | " | " | " | —C≡C—CH₃ |
| " | " | " | " | —C≡C—Cl |
| 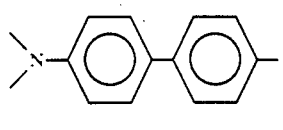 | | CH₃ | OH | —CH₂—C≡C—H |

-continued

| | | | | |
|---|---|---|---|---|
| ″ | ″ | ″ | −C≡C−H | −H |
| ″ | ″ | ″ | ″ | −OH |
| ″ | ″ | ″ | −C(=O)−CH$_2$OH | −H |
| ″ | 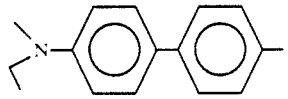 | ″ | ″ | ″ |
| ″ | ″ | ″ | OH | −C≡C−H |
| ″ | ″ | ″ | ″ | −C≡C−CH$_3$ |
| ″ | ″ | ″ | ″ | −C≡C−Cl |
| ″ | ″ | ″ | ″ | −CH$_2$−C≡C−H |
| ″ | ″ | ″ | −C≡C−H | −OH |
| ″ | 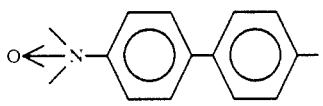 | ″ | ″ | ″ |
| ″ | ″ | ″ | OH | −C≡C−H |
| ″ | ″ | ″ | ″ | −C≡C−CF$_3$ |
| ″ | ″ | ″ | ″ | −C≡C−CH$_3$ |
| ″ | ″ | ″ | ″ | −CH$_2$−C≡C−H |
| ″ | ″ | ″ | ″ | −H |
| ″ | 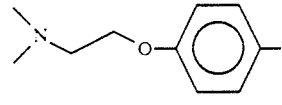 | ″ | ″ | −C≡C−H |
| ″ | ″ | ″ | −C≡C−H | −CH$_2$−C≡C−H |
| ″ | ″ | ″ | ″ | −OH |
| ″ | ″ | ″ | −C(=O)−CH$_2$OH | −H |
| ″ | 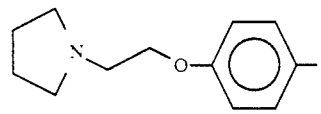 | ″ | ″ | ″ |
| ″ | ″ | ″ | −C≡C−H | −OH |
| ″ | ″ | ″ | −OH | −C≡C−H |
| ″ | ″ | ″ | ″ | −C≡C−CH$_3$ |
| ″ | ″ | ″ | ″ | −CH$_2$−C≡C−H |
| ″ | 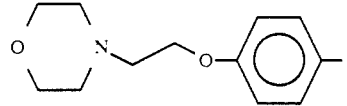 | ″ | −OH | −C≡C−H |
| ″ | ″ | ″ | ″ | −C≡C−CH$_3$ |
| 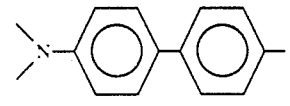 | ″ | CH$_3$ | OH | −CH$_2$−C≡C−H |
| ″ | ″ | ″ | ″ | −H |
| ″ | ″ | ″ | −C≡C−H | −OH |
| ″ | ″ | ″ | −C(=O)−CH$_2$OH | −H |

-continued

| | | | | |
|---|---|---|---|---|
| " | [Et(Me)N-biphenyl-] | " | " | " |
| " | " | " | OH | −C≡C−H |
| " | " | " | " | −C≡C−CH₃ |
| " | " | " | " | −C≡C−Cl |
| " | " | " | " | −CH₂−C≡C−H |
| " | " | " | −C≡C−H | −OH |
| " | [Me₂N(O)-biphenyl-] | " | " | " |
| " | " | " | OH | −C≡C−H |
| " | " | " | " | −C≡C−CF₃ |
| " | " | " | " | −C≡C−CH₃ |
| " | " | " | " | −CH₂−C≡C−H |
| " | " | " | " | −H |
| " | " | " | " | −C≡C−H |
| " | [Me₂N-CH₂CH₂-O-phenyl-] | " | " | |
| " | " | " | −C≡C−H | −CH₂−C≡C−H |
| " | " | " | " | −OH |
| " | " | " | −C(=O)−CH₂OH | −H |
| " | [pyrrolidino-CH₂CH₂-O-phenyl-] | " | | |
| " | " | " | −C≡C−H | −OH |
| " | " | " | −OH | −C≡C−H |
| " | " | " | " | −C≡C−CH₃ |
| " | " | " | " | −CH₂−C≡C−H |
| " | " | " | −OH | −C≡C−H |
| " | [morpholino-CH₂CH₂-O-phenyl-] | " | | |
| " | " | " | " | −C≡C−CH₃ |
| [octahydronaphthalenone] | [Me₂N-biphenyl-] | CH₃ | OH | −CH₂−C≡C−H |
| " | " | " | −C≡C−H | −H |
| " | " | " | | −OH |
| " | " | " | −C(=O)−CH₂OH | −H |
| " | [Et(Me)N-biphenyl-] | " | | |
| " | " | " | OH | −C≡C−H |
| " | " | " | " | −C≡C−CH₃ |
| " | " | " | " | −C≡C−Cl |

-continued

| | | | | |
|---|---|---|---|---|
| " | " | " | −C≡C−H | −CH₂−C≡C−H, −OH |
| " | [structure: (CH₃)₂N(O)-C₆H₄-C₆H₄-] | " | " | " |
| " | " | " | OH | −C≡C−H |
| " | " | " | " | −C≡C−CF₃ |
| " | " | " | " | −C≡C−CH₃ |
| " | " | " | " | −CH₂−C≡C−H |
| " | " | " | " | −H |
| " | [structure: (CH₃)₂N-CH₂CH₂-O-C₆H₄-] | " | " | −C≡C−H |
| " | " | " | " | −CH₂−C≡C−H |
| " | " | " | −C≡C−H | −OH |
| " | " | " | −C(=O)−CH₂OH | −H |
| " | [structure: pyrrolidine-CH₂CH₂-O-C₆H₄-] | " | " | " |
| " | " | " | −C≡C−H | −OH |
| " | " | " | −OH | −C≡C−H |
| " | " | " | " | −C≡C−CH₃ |
| " | " | " | " | −CH₂−C≡C−H |
| " | [structure: morpholine-CH₂CH₂-O-C₆H₄-] | " | −OH | −C≡C−H |
| " | " | " | " | −C≡C−CH₃ |
| [structure: decalone with methyl groups] | [structure: (CH₃)₂N-C₆H₄-C₆H₄-] | CH₃ | OH | −CH₂−C≡C−H |
| " | " | " | −C≡C−H | −H, −OH |
| " | " | " | −C(=O)−CH₂OH | −H |
| " | [structure: CH₃(C₂H₅)N-C₆H₄-C₆H₄-] | " | " | " |
| " | " | " | OH | −C≡C−H |
| " | " | " | " | −C≡C−CH₃ |
| " | " | " | " | −C≡C−Cl |
| " | " | " | " | −CH₂−C≡C−H |
| " | " | " | −C≡C−H | −OH |
| " | [structure: (CH₃)₂N(O)-C₆H₄-C₆H₄-] | " | " | " |

-continued

| | | | | |
|---|---|---|---|---|
| ″ | ″ | ″ | OH | —C≡C—H |
| ″ | ″ | ″ | ″ | —C≡C—CF₃ |
| ″ | ″ | ″ | ″ | —C≡C—CH₃ |
| ″ | ″ | ″ | ″ | —CH₂—C≡C—H |
| ″ | ″ | ″ | ″ | —H |
| ″ | (CH₃)₂N-CH₂CH₂-O-C₆H₄- | ″ | ″ | —C≡C—H |
| ″ | ″ | ″ | ″ | —CH₂—C≡C—H |
| ″ | ″ | ″ | —C≡C—H | —OH |
| ″ | ″ | ″ | -C(O)-CH₂OH | —H |
| ″ | pyrrolidinyl-CH₂CH₂-O-C₆H₄- | ″ | ″ | ″ |
| ″ | ″ | ″ | —C≡C—H | —OH |
| ″ | ″ | ″ | —OH | —C≡C—H |
| ″ | ″ | ″ | ″ | —C≡C—CH₃ |
| ″ | ″ | ″ | ″ | —CH₂—C≡C—H |
| ″ | morpholinyl-CH₂CH₂-O-C₆H₄- | ″ | —OH | —C≡C—H |
| ″ | ″ | ″ | ″ | —C≡C—CH₃ |
| HO-tetrahydronaphthyl(dimethyl) | morpholinyl-CH₂CH₂-O-C₆H₄- | CH₃ | —OH | —CH₂—C≡C—H |
| ″ | ″ | ″ | —C≡C—H | —OH |
| ″ | ″ | ″ | -C(O)-CH₂OH | —H |
| ″ | (CH₃)₂N-CH₂CH₂-S-C₆H₄- | ″ | ″ | ″ |
| ″ | ″ | ″ | —C≡C—H | OH |
| ″ | ″ | ″ | OH | —C≡C—CF₃ |
| ″ | ″ | ″ | OH | —C≡C—H |
| ″ | ″ | ″ | ″ | —CH₂—CH=CH₂ |
| ″ | ″ | ″ | ″ | CH₂—C≡C—H |
| ″ | ″ | ″ | ″ | —CH₃ |
| ″ | ″ | ″ | -C(O)-CH₃ | —CH₃ |
| ″ | ″ | ″ | OH | —CH₂—CN |

-continued

| Structure | | | | |
|---|---|---|---|---|
| 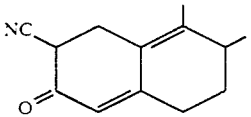 | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |
| " | " | " | | —H |
| " | " | " | 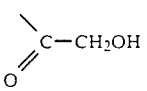 | |
| 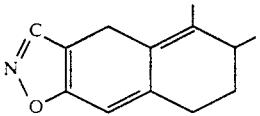 | 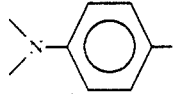 | " | | |
| " | " | " | —C≡C—H | —OH |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —CH₂—C≡C—H |
| " | " | CH₂CH₃ | " | —C≡C—H |
| " | " | " | " | —C≡C—CH₃ |

| 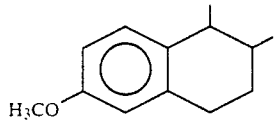 | 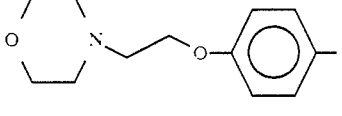 | CH₃ | —OH | —CH₂—C≡C—H |
| " | " | " | —C≡C—H | —OH |
| " | " | " | 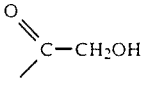 | —H |
| " | 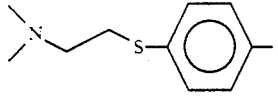 | " | | |
| " | " | " | —C≡C—H | OH |
| " | " | " | OH | —C≡C—CF₃ |
| " | " | " | OH | —C≡C—H |
| " | " | " | " | —CH₂—CH=CH₂ |
| " | " | " | " | CH₂—C≡C—H |
| " | " | " | " | —CH₂ |
| " | " | " | 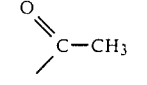 | —CH₃ |
| " | " | " | OH | —CH₂—CN |
| " | " | " | OH | —C≡C—H |
| 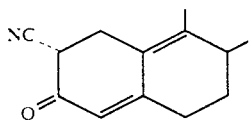 | " | " | | |
| " | " | " | " | —C≡C—CH₃ |
| " | " | " | " | —C≡C—CH₂CH₃ |

-continued

| | | | | |
|---|---|---|---|---|
| " | " | " | " | —C≡C—Cl |
| " | " | " | " | —CH₂—C≡C—H |
| " | " | " | —C≡C—H | —OH |
| " | " | " | | —H |
| " | " | " | 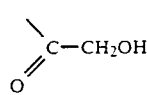 | |
| 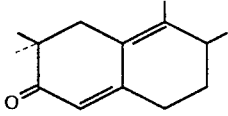 | " | " | —C≡C—H | —OH |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —CH₂—C≡C—H |
| " | " | CH₂CH₃ | " | —C≡C—H |
| " | " | " | " | —C≡C—CH₃ |
| " | " | CH₃ | —OH | —CH₂—C≡C—H |
| 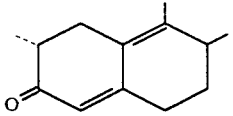 | 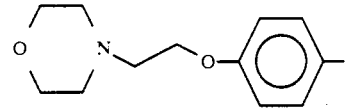 | | | |
| " | " | " | —C≡C—H | —OH |
| " | " | " | 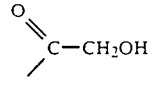 | —H |
| " | 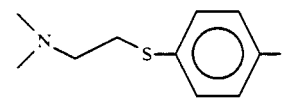 | " | | " |
| " | " | " | —C≡C—H | —OH |
| " | " | " | OH | —C≡C—CF₃ |
| " | " | " | OH | —C≡C—H |
| " | " | " | " | —CH₂—CH=CH₂ |
| " | " | " | " | CH₂—C≡C—H |
| " | " | " | " | —CH₂ |
| " | " | " | 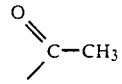 | —CH₃ |
| " | " | " | OH | —CH₂—CN |
| " | " | " | OH | —C≡C—H |
| 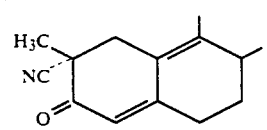 | | | | |
| " | " | " | " | —C≡C—CH₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |
| " | " | " | | —H |
| " | " | " | 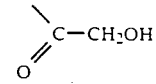 | |

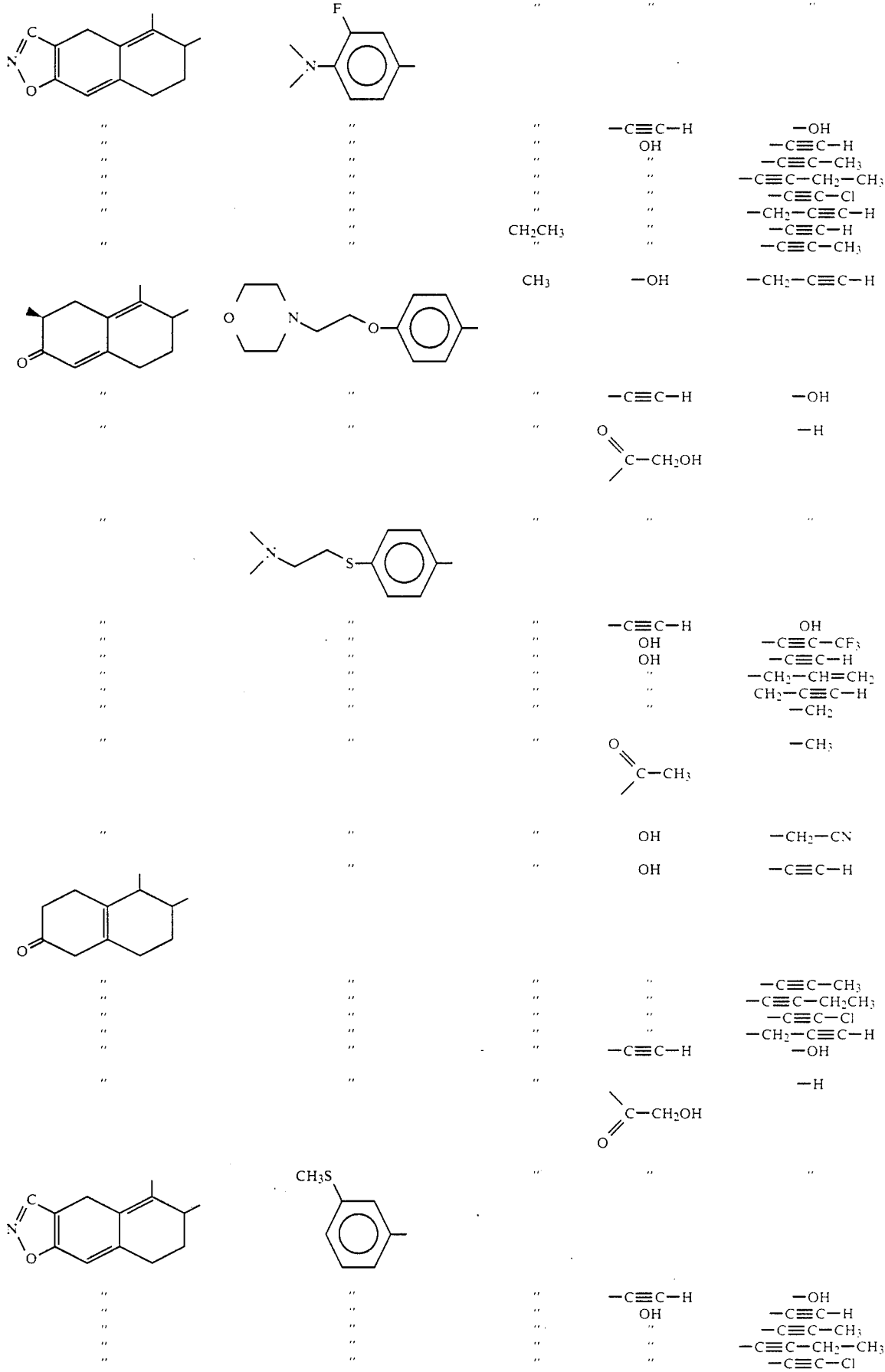

-continued

| | | | | |
|---|---|---|---|---|
| " | " | " | " | —CH₂—C≡C—H |
| " | " | CH₂CH₃ | " | —C≡C—H |
| " | " | " | " | —C≡C—CH₃ |
| 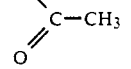 | 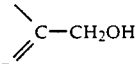 | CH₂CH₃ | OH | —CH₂—C≡C—H |
| " | " | " | " | —CH₂—CH=CH₂ |
| " | " | " | C—CH₃ ‖ O | —CH₃ |
| " | " | " | C—CH₂OH ‖ O | —H |
| " | " | " | —C≡C—H | —OH |
| " | 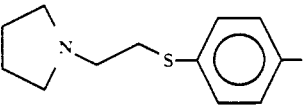 | CH₃ | OH | —C≡C—H |
| " | " | " | " | —C≡C—CH₃ |
| " | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |
| " | " | " | —C≡C—H | —OH |
| " | " | " | C—CH₂OH ‖ O | —H |
| " | " | " | C—CH₃ ‖ O | —CH₃ |
| " | " | " | C—CH₃ ‖ O | —H |
| " | 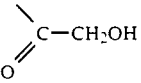 | " | " | " |
| " | " | " | " | —CH₃ |
| " | " | " | C—CH₂OH ‖ O | —H |
| " | " | " | —C≡C—H OH | —OH |
| " | " | " | " | —C≡C—H |
| " | " | " | " | —C≡C—CH₃ |
| " | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |
| " | 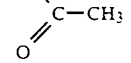 | " | " | —C≡C—H |

-continued
| | | | | |
|---|---|---|---|---|
| " | " | " | " | —C≡C—CH₃ |
| " | " | " | " | —CH₂—C≡C—H |
| 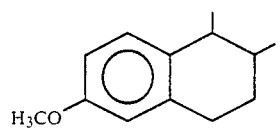 | 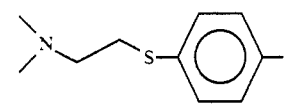 | CH₂CH₃ | OH | —CH₂—C≡C—H |
| " | " | " | " | —CH₂—CH=CH₂ |
| " | " | " | 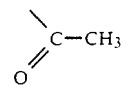 | —CH₃ |
| " | " | " | 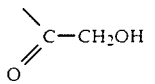 | —H |
| " | " | " | —C≡C—H | —OH |
| " | 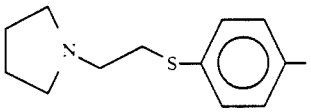 | CH₃ | OH | —C≡C—H |
| " | " | " | " | —C≡C—CH₃ |
| " | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |
| " | " | " | —C≡C—H | —OH |
| " | " | " | 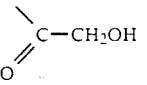 | —H |
| " | " | " | 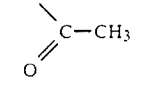 | —CH₃ |
| " | " | " | 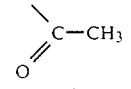 | —H |
| " |  | " | " | " |
| " | " | " | " | —CH₃ |
| " | " | " | 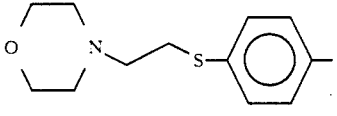 | —H |
| " | " | " | —C≡C—H | —OH |
| " | " | " | OH | —C≡C—H |
| " | " | " | " | —C≡C—CH₃ |
| " | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |

-continued

| | | | |
|---|---|---|---|
| " | Me₃Si—CH₂ attached to N(CH₃)—C₆H₄— | " | —C≡C—H |
| " | " | " | —C≡C—CH₃ |
| " | " | " | —CH₂—C≡C—E |
| [octahydronaphthalenone structure] | (CH₃)₂N—CH₂CH₂—S—C₆H₄— | CH₂CH₃ | OH, —CH₂—C≡C—H |
| " | " | " | —CH₂—CH=CH₂ |
| " | " | CH₃—C(=O)—CH₃ | —CH₃ |
| " | " | CH₃—C(=O)—CH₂OH | —H |
| " | " | —C≡C—H | —OH |
| " | pyrrolidine-N—CH₂CH₂—S—C₆H₄— | CH₃, OH | —C≡C—H |
| " | " | " | —C≡C—CH₃ |
| " | " | " | —C≡C—Cl |
| " | " | " | —C≡C—CH₂CH₃ |
| " | " | " | —CH₂—C≡C—H |
| " | " | " | —CH₂—CH=CH₂ |
| " | " | —C≡C—H | —OH |
| " | " | CH₃—C(=O)—CH₂OH | —H |
| " | " | CH₃—C(=O)—CH₃ | —CH₃ |
| " | " | CH₃—C(=O)—CH₃ | —H |
| " | morpholine-N—CH₂CH₂—S—C₆H₄— | " | " |
| " | " | " | —CH₃ |
| " | " | CH₃—C(=O)—CH₂OH | —H |
| " | " | —C≡C—H, OH | —OH |
| " | " | " | —C≡C—H |
| " | " | " | —C≡C—CH₃ |
| " | " | " | —C≡C—Cl |
| " | " | " | —C≡C—CH₂CH₃ |
| " | " | " | —CH₂—C≡C—H |
| " | " | " | —CH₂—CH=CH₂ |

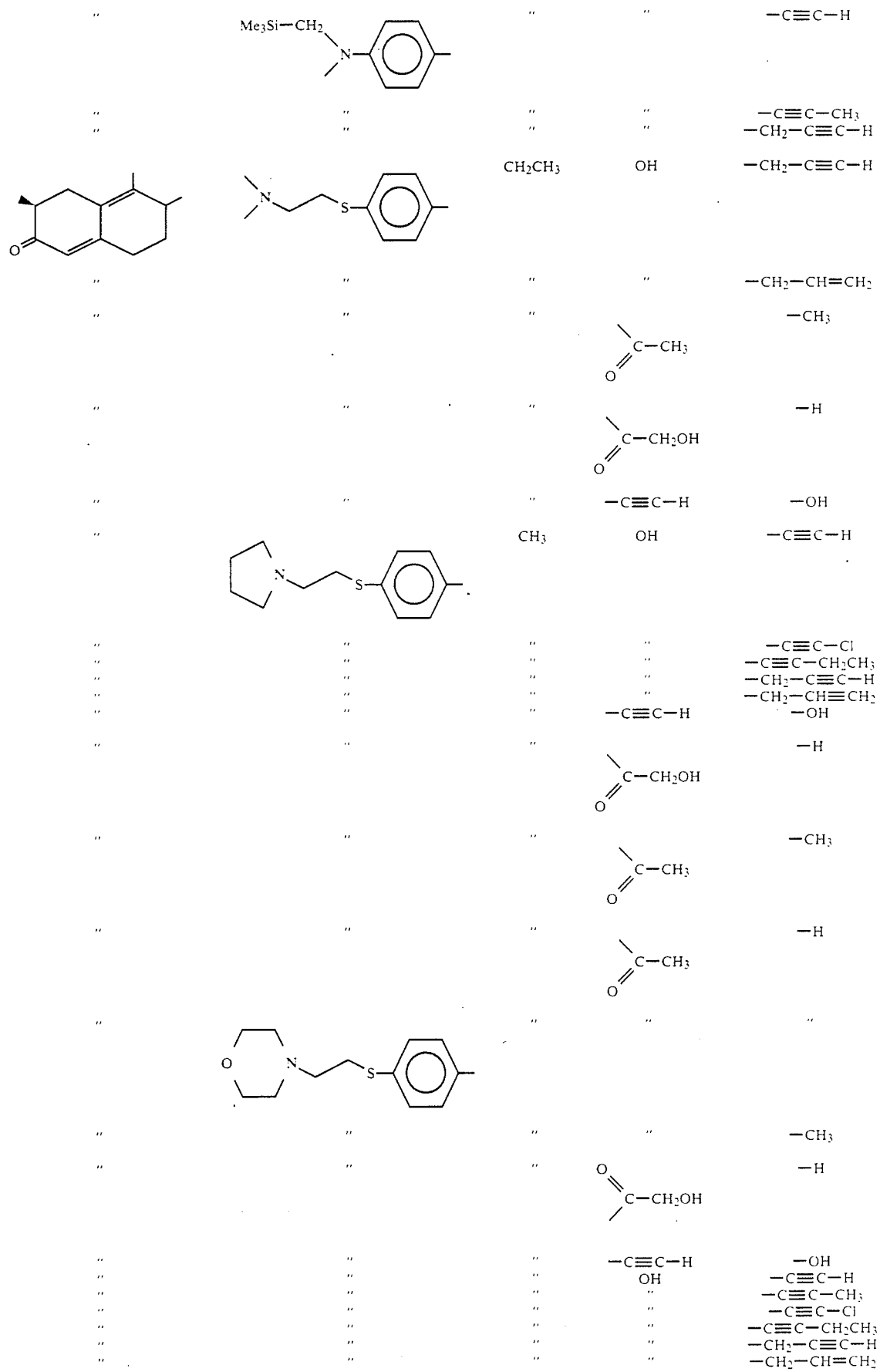

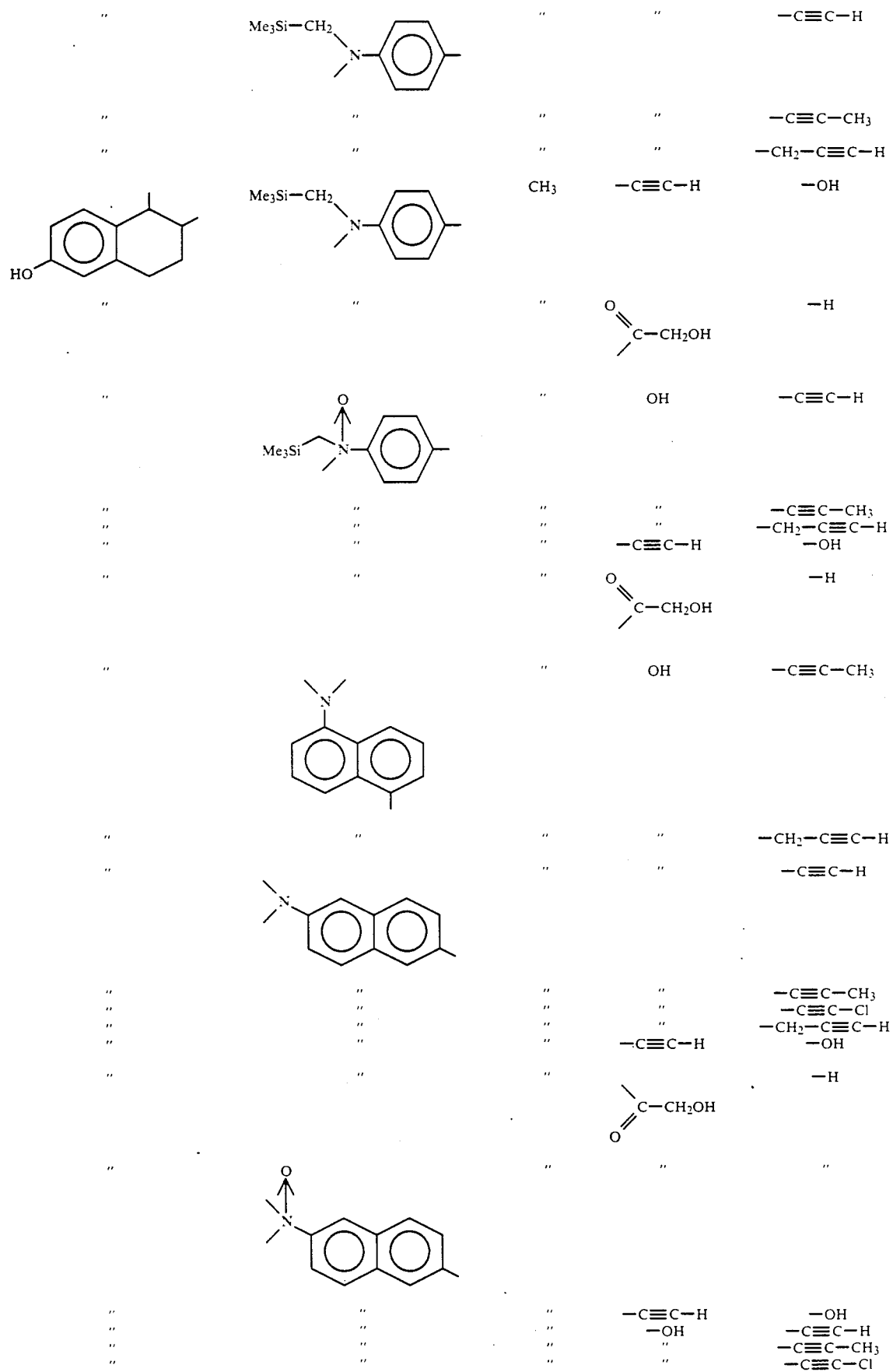

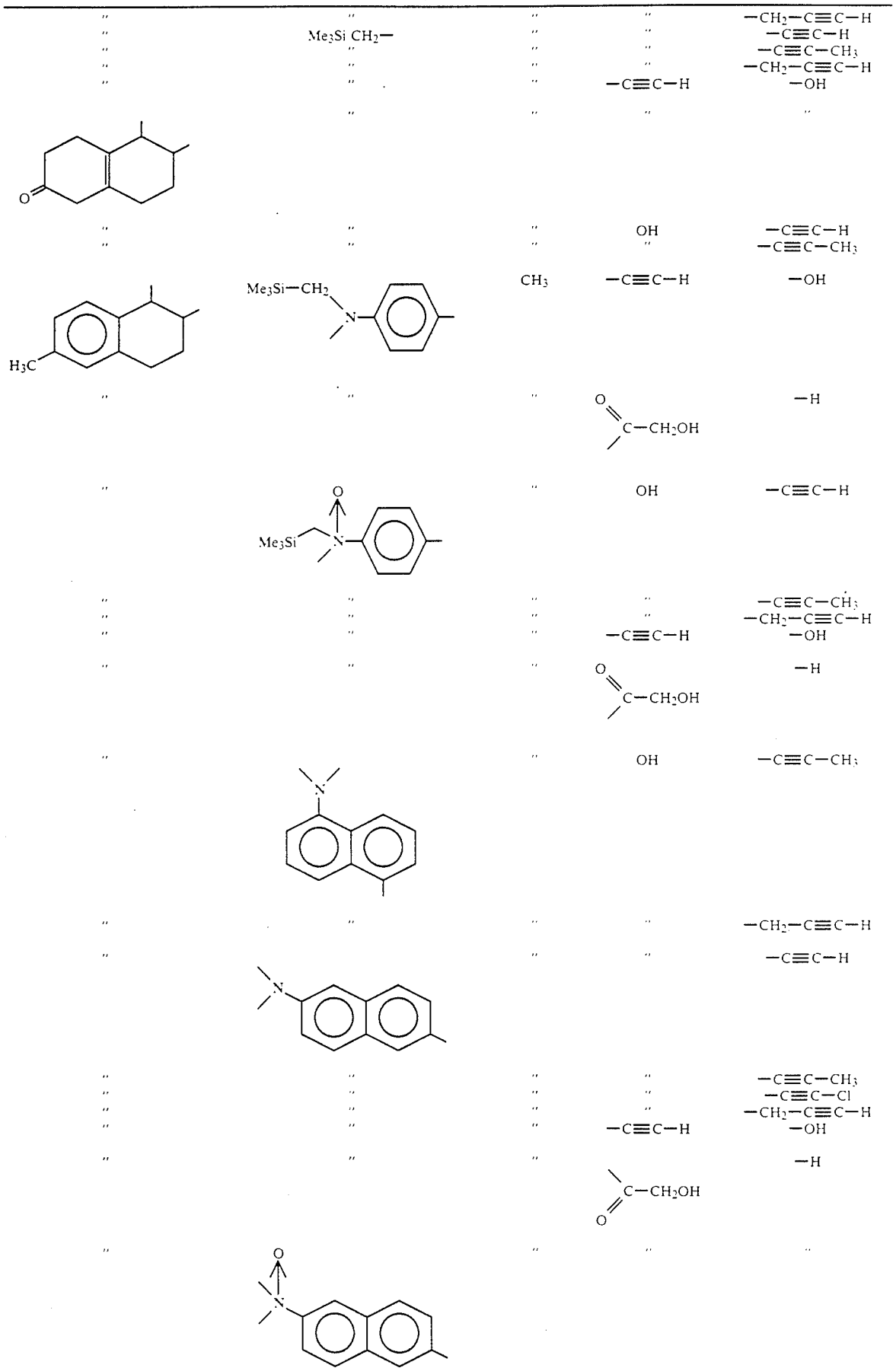

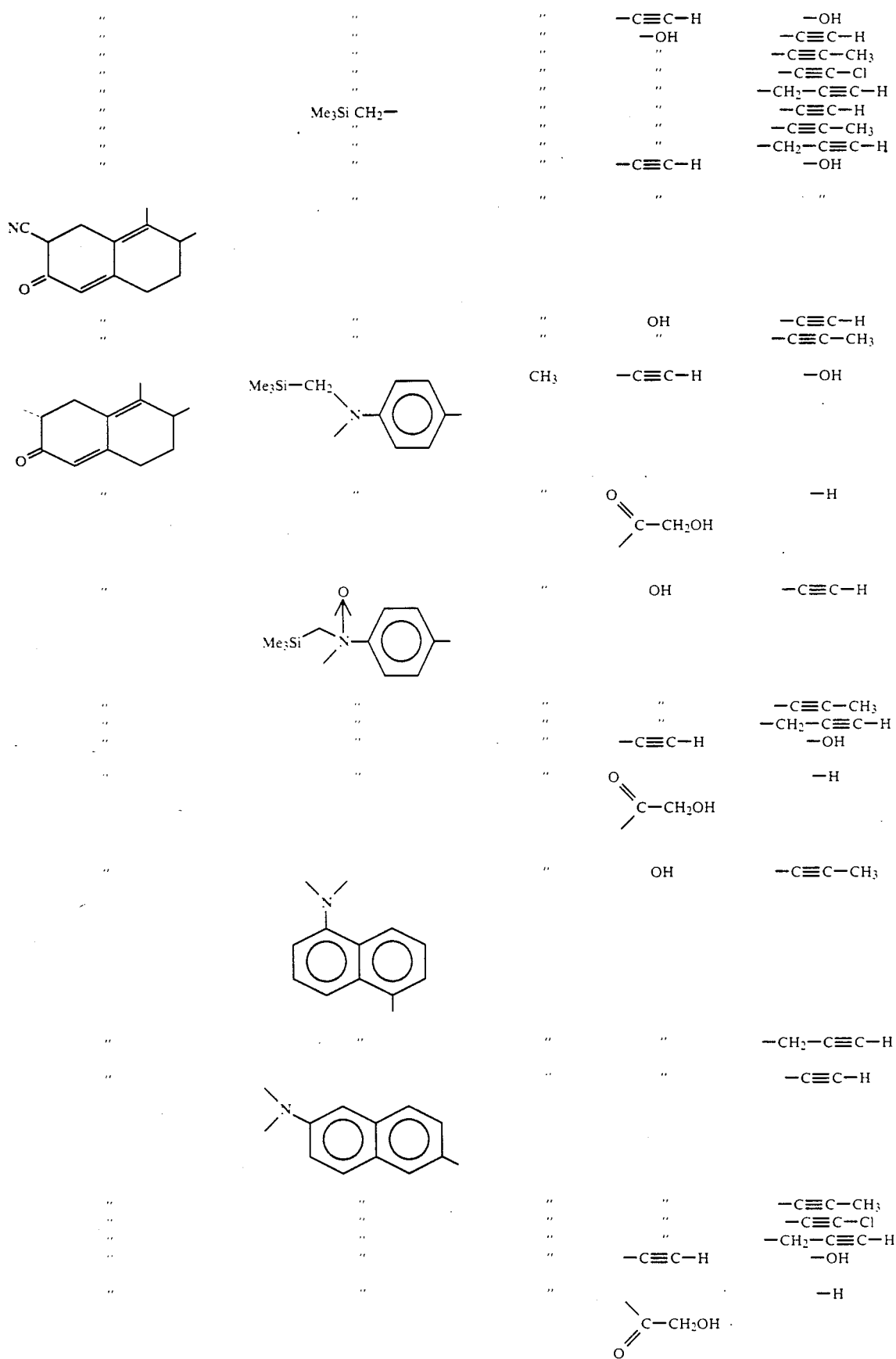

-continued
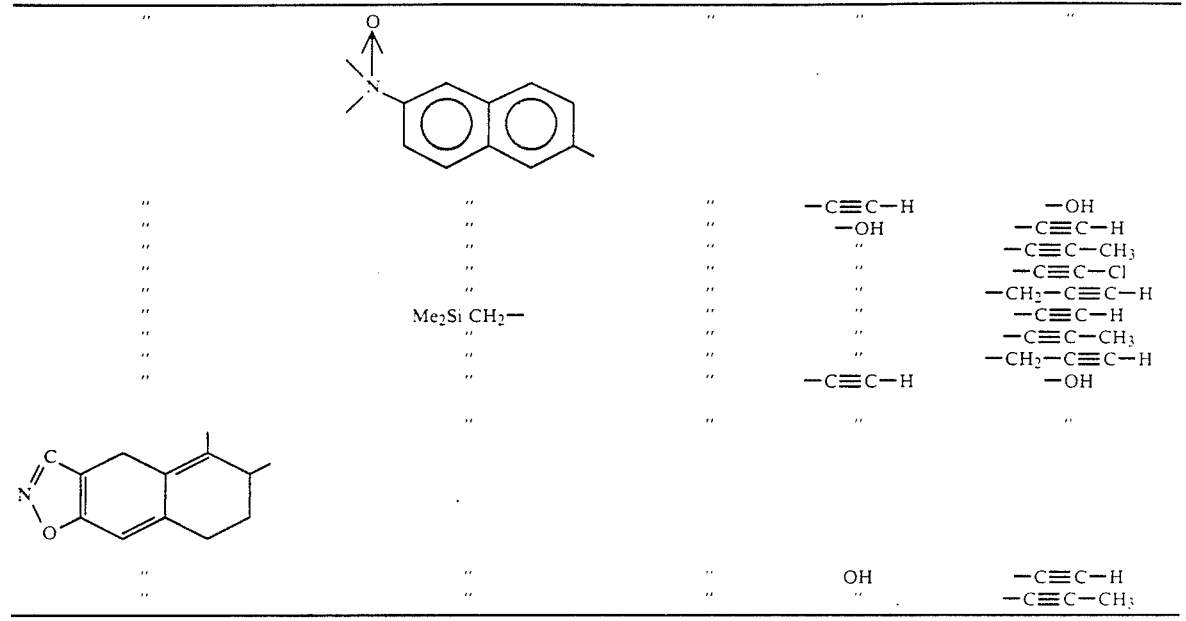
| | | | | |
|---|---|---|---|---|
| " | " | " | —C≡C—H | —OH |
| " | " | " | —OH | —C≡C—H |
| " | " | " | " | —C≡C—CH₃ |
| " | " | " | " | —C≡C—Cl |
| " | Me₂Si CH₂— | " | " | —CH₂—C≡C—H |
| " | " | " | " | —C≡C—H |
| " | " | " | " | —C≡C—CH₃ |
| " | " | " | " | —CH₂—C≡C—H |
| " | " | " | —C≡C—H | —OH |
| " | " | " | " | " |
| " | " | " | OH | —C≡C—H |
| " | " | " | " | —C≡C—CH₃ |
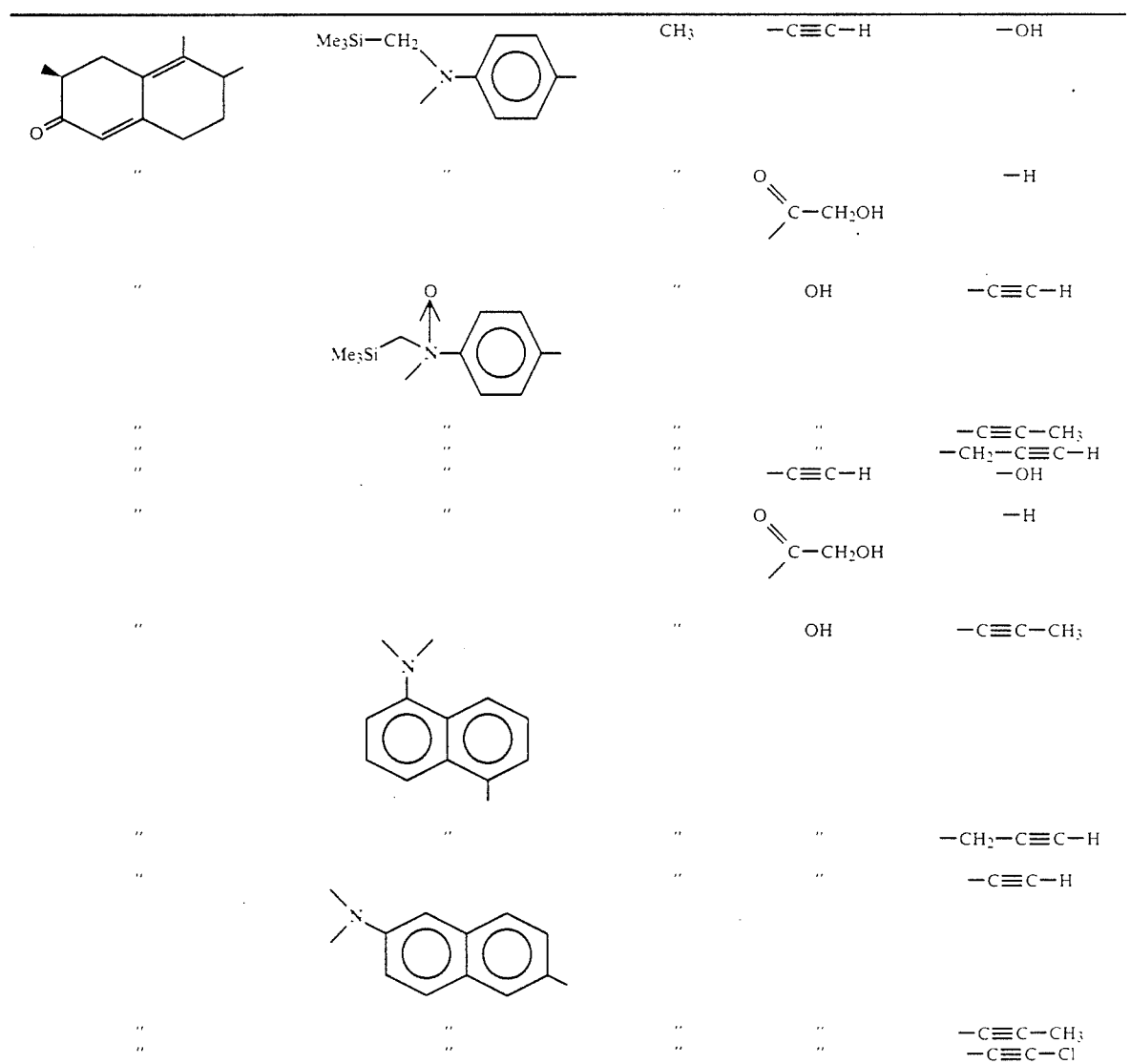

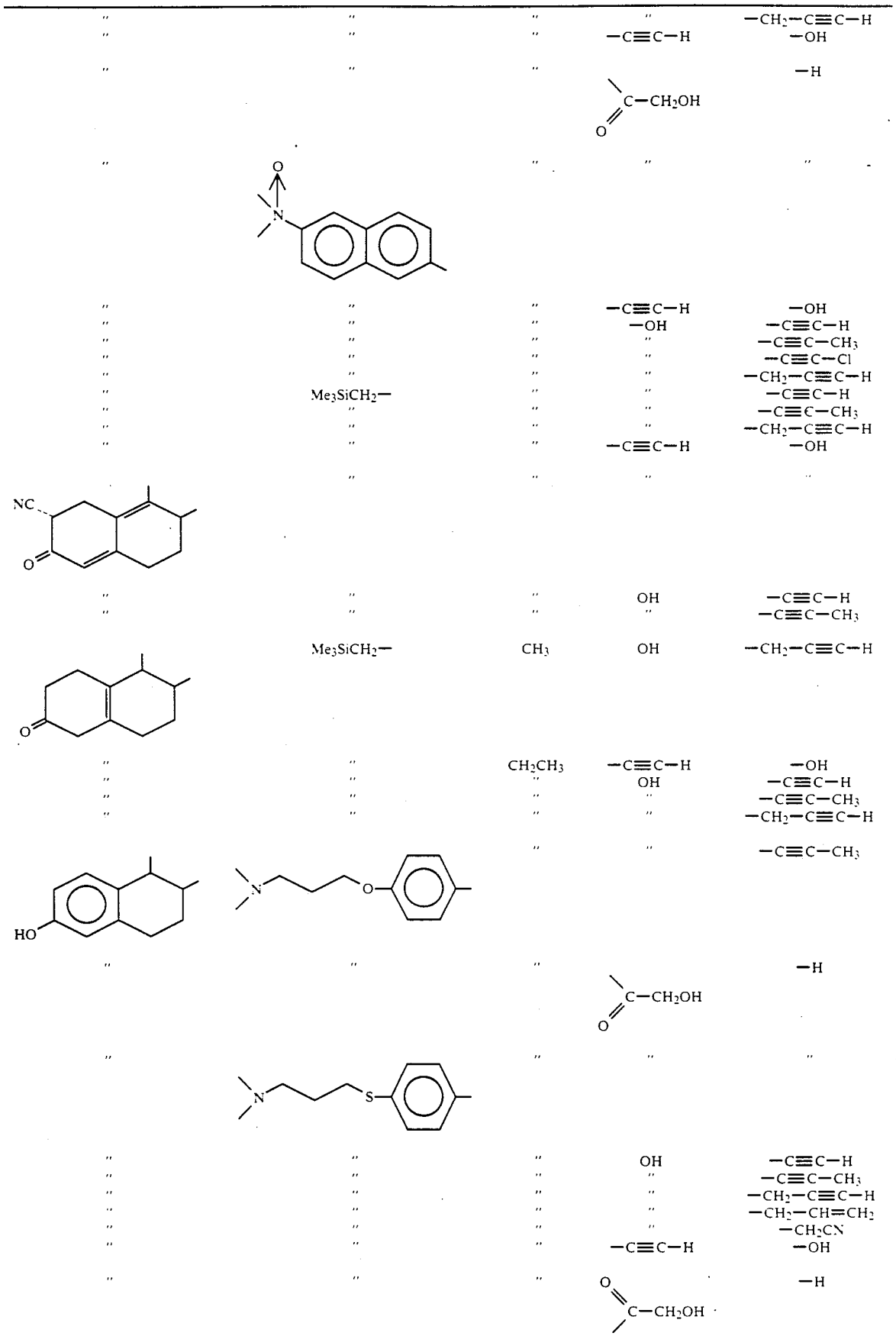

-continued

| | | | | -CH₃ |
| --- | --- | --- | --- | --- |
| | | | O=C(-CH₃)- | |
| ″ | ″ | ″ | OH | —H |
| ″ | ″ | ″ | OH | —C≡C—H |
| ″ | 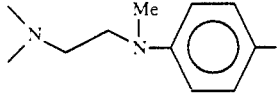 | ″ | ″ | —C≡C—CF₃ |
| ″ | ″ | ″ | ″ | —C≡C—CH₂CH₃ |
| ″ | ″ | ″ | ″ | —C≡C—Cl |
| ″ | ″ | ″ | ″ | —CH₂—C≡C—H |
| ″ | ″ | ″ | —C≡C—H | —OH |
| ″ | ″ | ″ | —C(=O)—CH₂OH | —H |
| ″ | ″ | ″ | —C(=O)—CH₃ | —CH₃ |
| ″ | ″ | CH₂CH₃ | OH | —C≡C—H |
| ″ | ″ | ″ | ″ | —C≡C—CH₃ |
| ″ | ″ | ″ | ″ | —CH₂—C≡C—H |
| 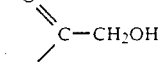 | Me₃SiCH₂— | CH₃ | OH | —CH₂—C≡C—H |
| ″ | ″ | CH₂CH₃ | —C≡C—H | —OH |
| ″ | ″ | ″ | OH | —C≡C—H |
| ″ | ″ | ″ | ″ | —C≡C—CH₃ |
| ″ | ″ | ″ | ″ | —CH₂—C≡C—H |
| ″ | ″ | ″ | ″ | —C≡C—CH₃ |
| 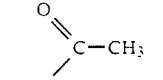 | 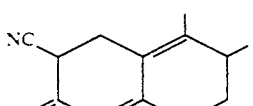 | ″ | —C(=O)—CH₂OH | —H |
| ″ | 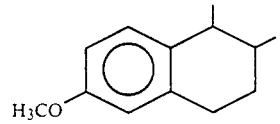 | ″ | ″ | ″ |
| ″ | ″ | ″ | OH | —C≡C—H |
| ″ | ″ | ″ | ″ | —C≡C—CH₃ |
| ″ | ″ | ″ | ″ | —CH₂—C≡C—H |
| ″ | ″ | ″ | ″ | —CH₂—CH=CH₂ |
| ″ | ″ | ″ | ″ | —CH₂CN |
| ″ | ″ | ″ | —C≡C—H | —OH |
| ″ | ″ | ″ | —C(=O)—CH₂OH | —H |
| ″ | ″ | ″ | O=C(-CH₃)- | —CH₃ |
| ″ | ″ | ″ | OH | —H |

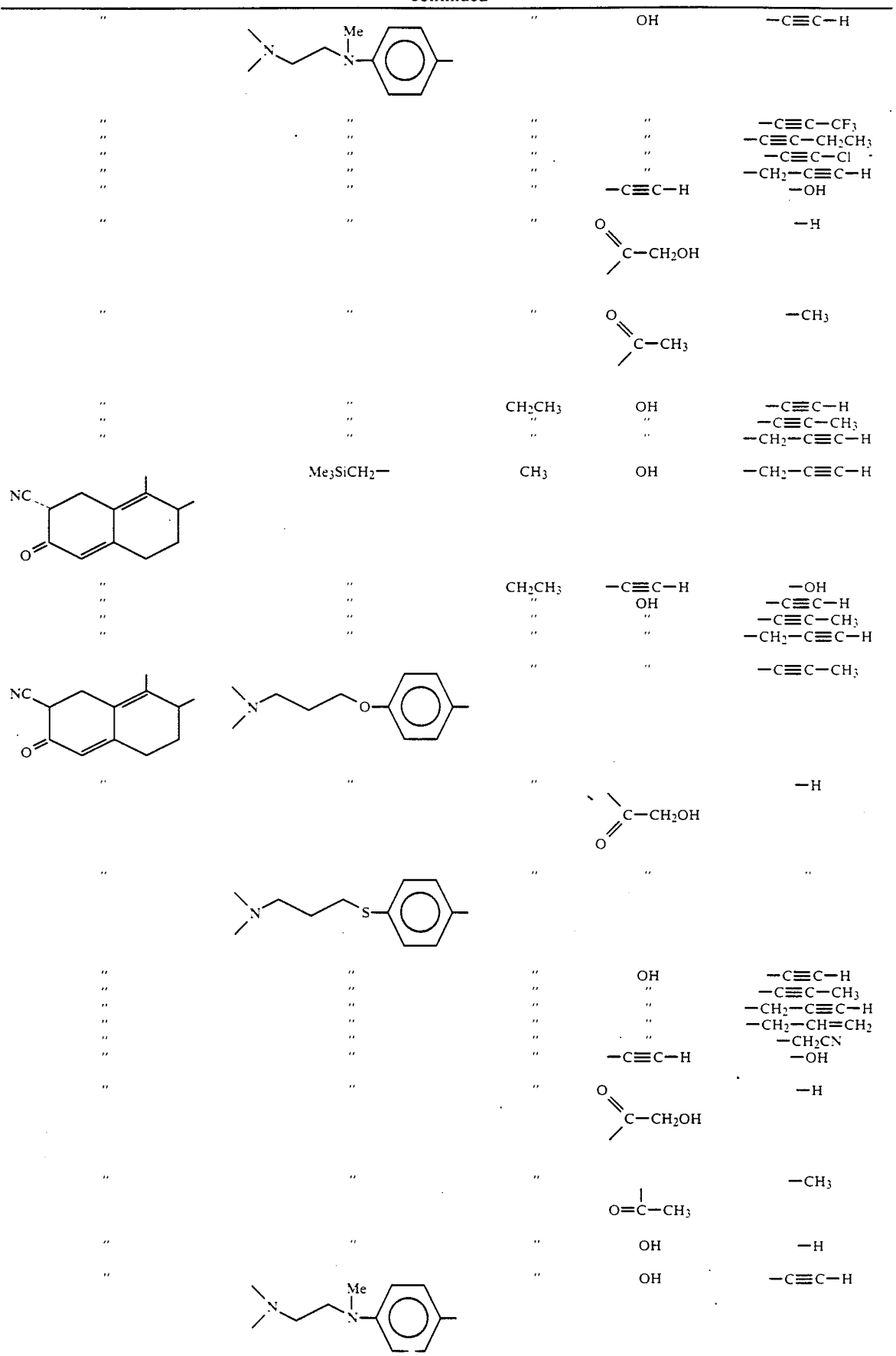

-continued

| | | | | |
|---|---|---|---|---|
| " | " | " | " | —C≡C—CF₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |
| " | " | " | ⟨C(=O)—CH₂OH⟩ | —H |
| " | " | " | ⟨C(=O)—CH₃⟩ | —CH₃ |
| " | " | CH₂CH₃ | OH | —C≡C—H |
| " | " | " | " | —C≡C—CH₃ |
| " | " | " | " | —CH₂—C≡C—H |
| 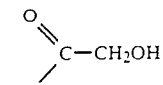 | Me₃SiCH₂— | CH₃ | OH | —CH₂—C≡C—H |
| " | " | CH₂CH₃ | —C≡C—H | —OH |
| " | " | " | OH | —C≡C—H |
| " | " | " | " | —C≡C—CH₃ |
| " | " | " | " | —CH₂—C≡C—H |
| " | " | " | " | —C≡C—CH₃ |
| 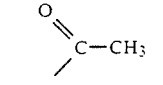 | 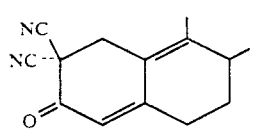 | " | ⟨C(=O)—CH₂OH⟩ | —H |
| " | 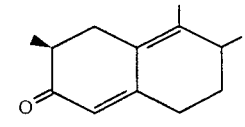 | " | " | " |
| " | " | " | OH | —C≡C—H |
| " | " | " | " | —C≡C—CH₃ |
| " | " | " | " | —CH₂—C≡C—H |
| " | " | " | " | —CH₂—CH=CH₂ |
| " | " | " | " | —CH₂CN |
| " | " | " | —C≡C—H | —OH |
| " | " | " | ⟨C(=O)—CH₂OH⟩ | —H |
| " | " | " | ⟨O=C—CH₃⟩ | —CH₃ |
| " | " | " | OH | —H |
| " | 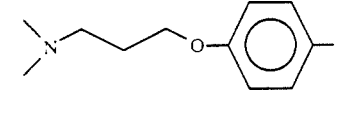 | " | OH | —C≡C—H |
| " | " | " | " | —C≡C—CF₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |

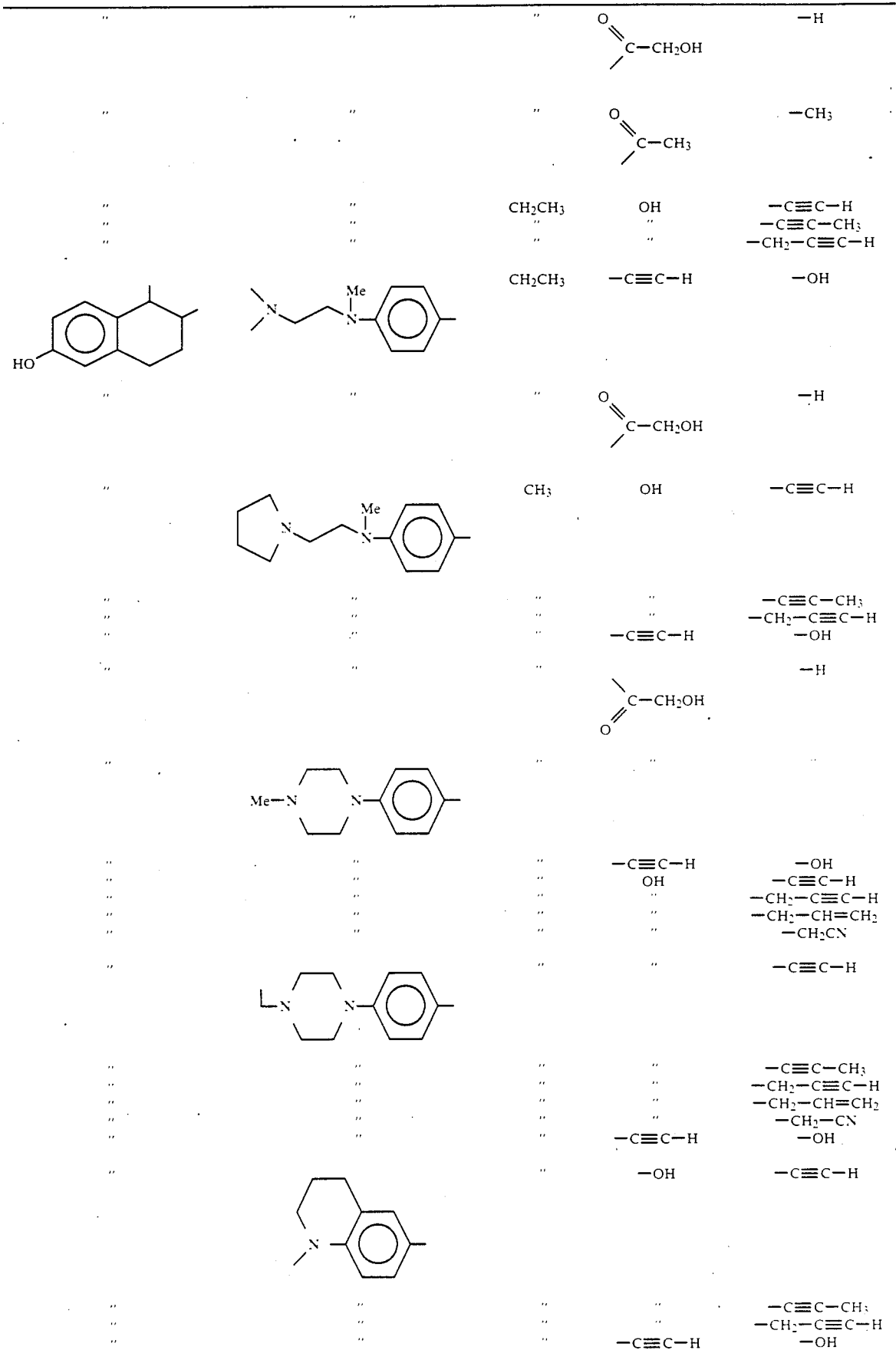

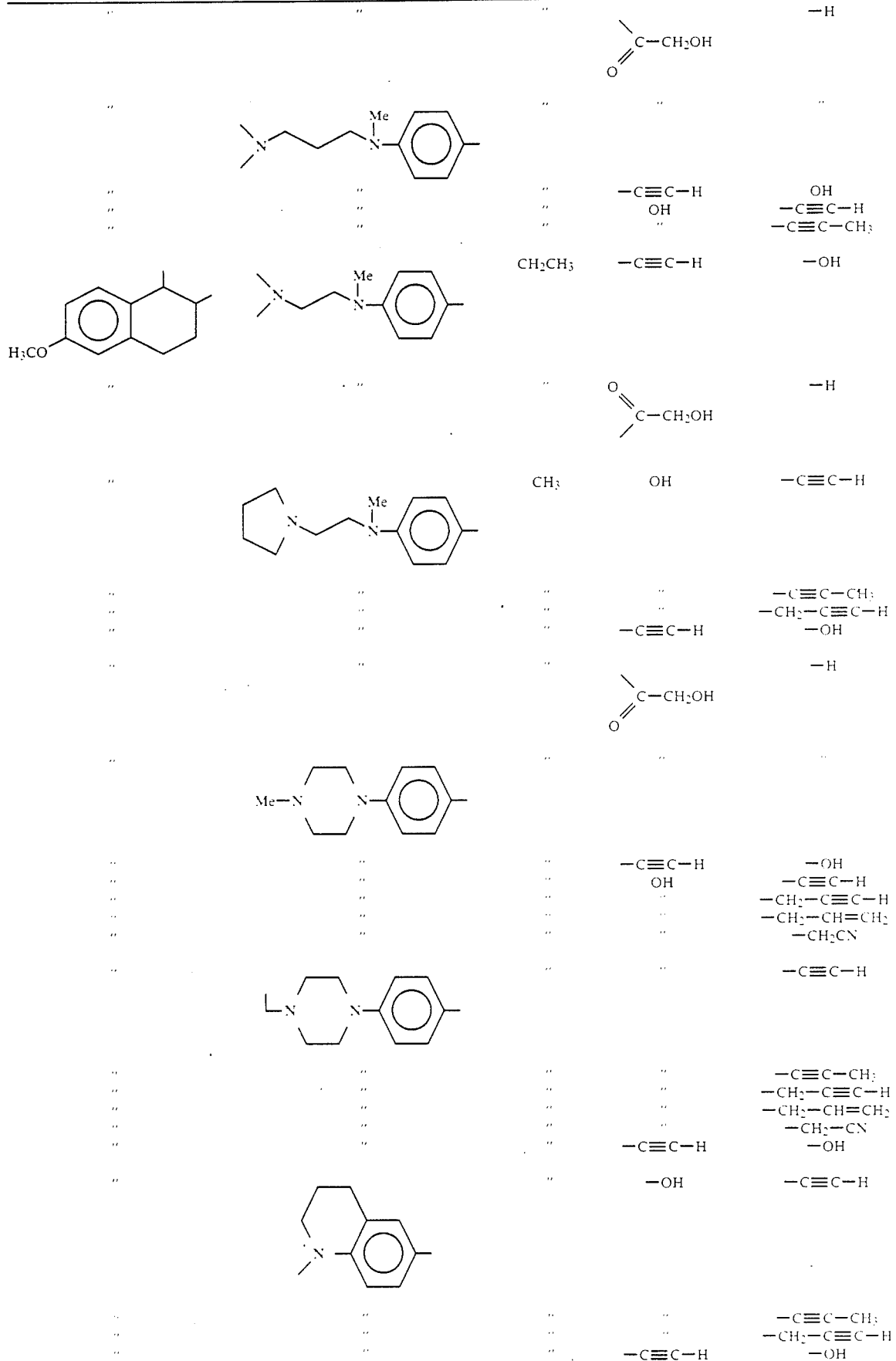

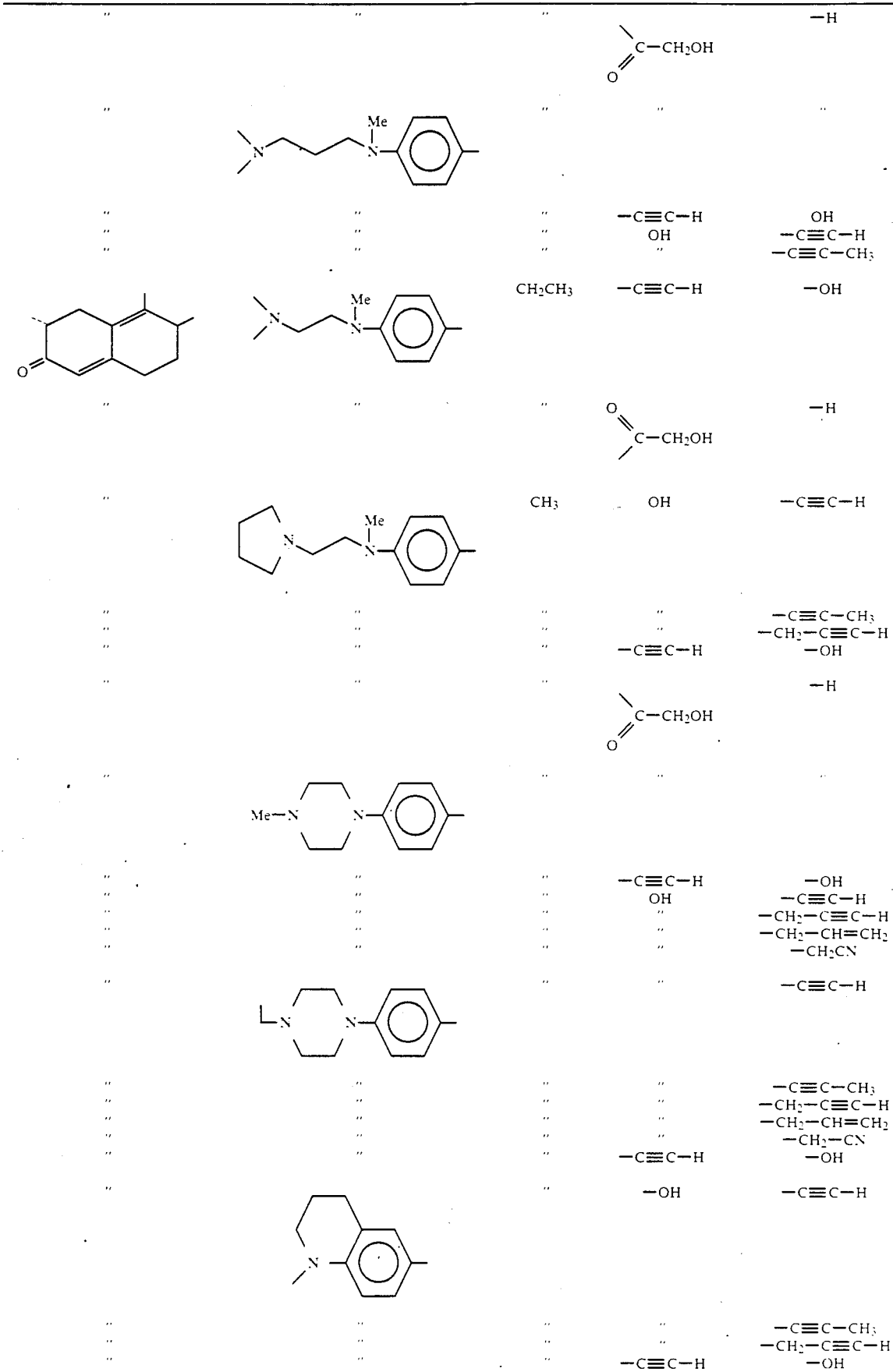

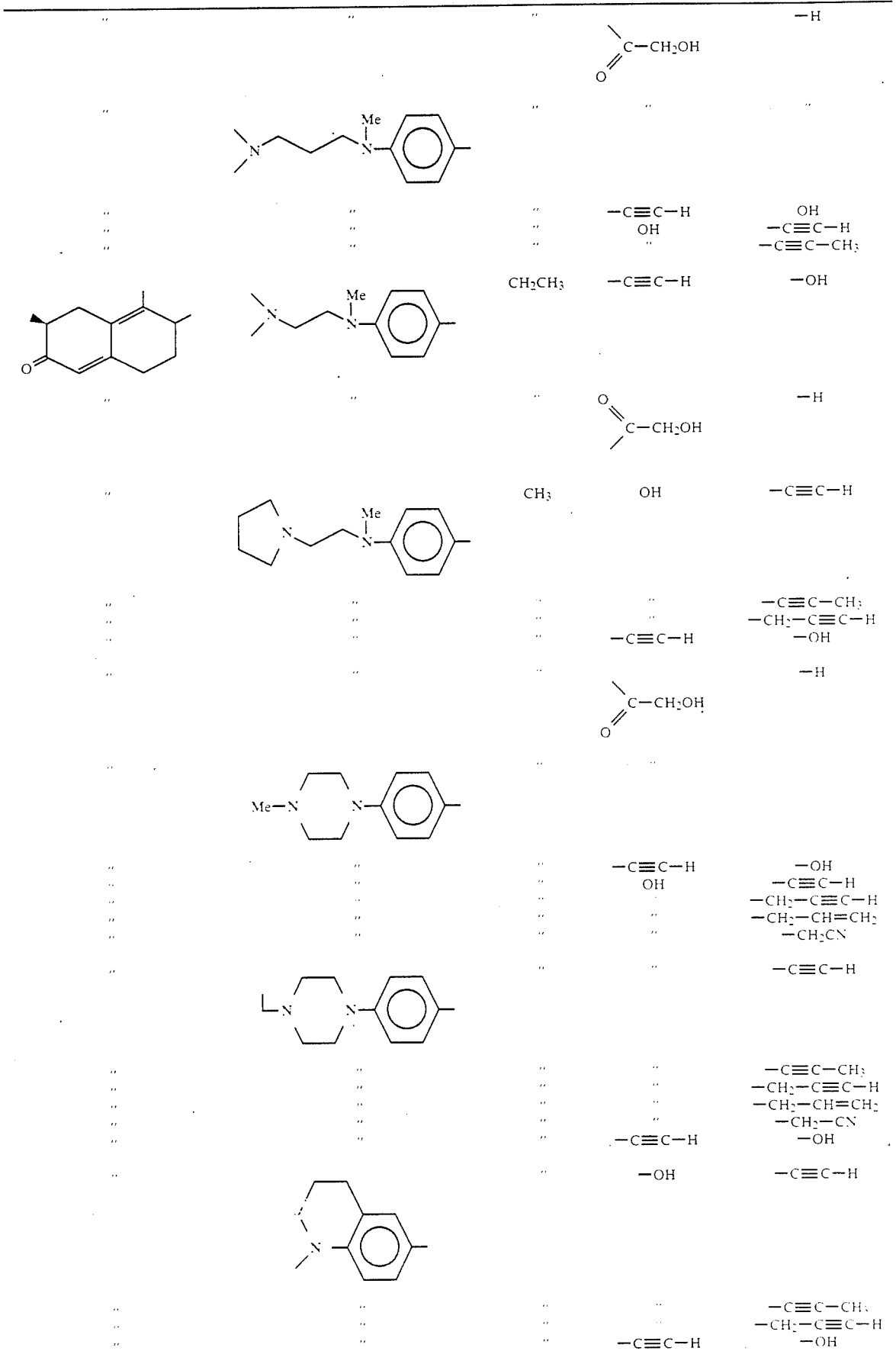

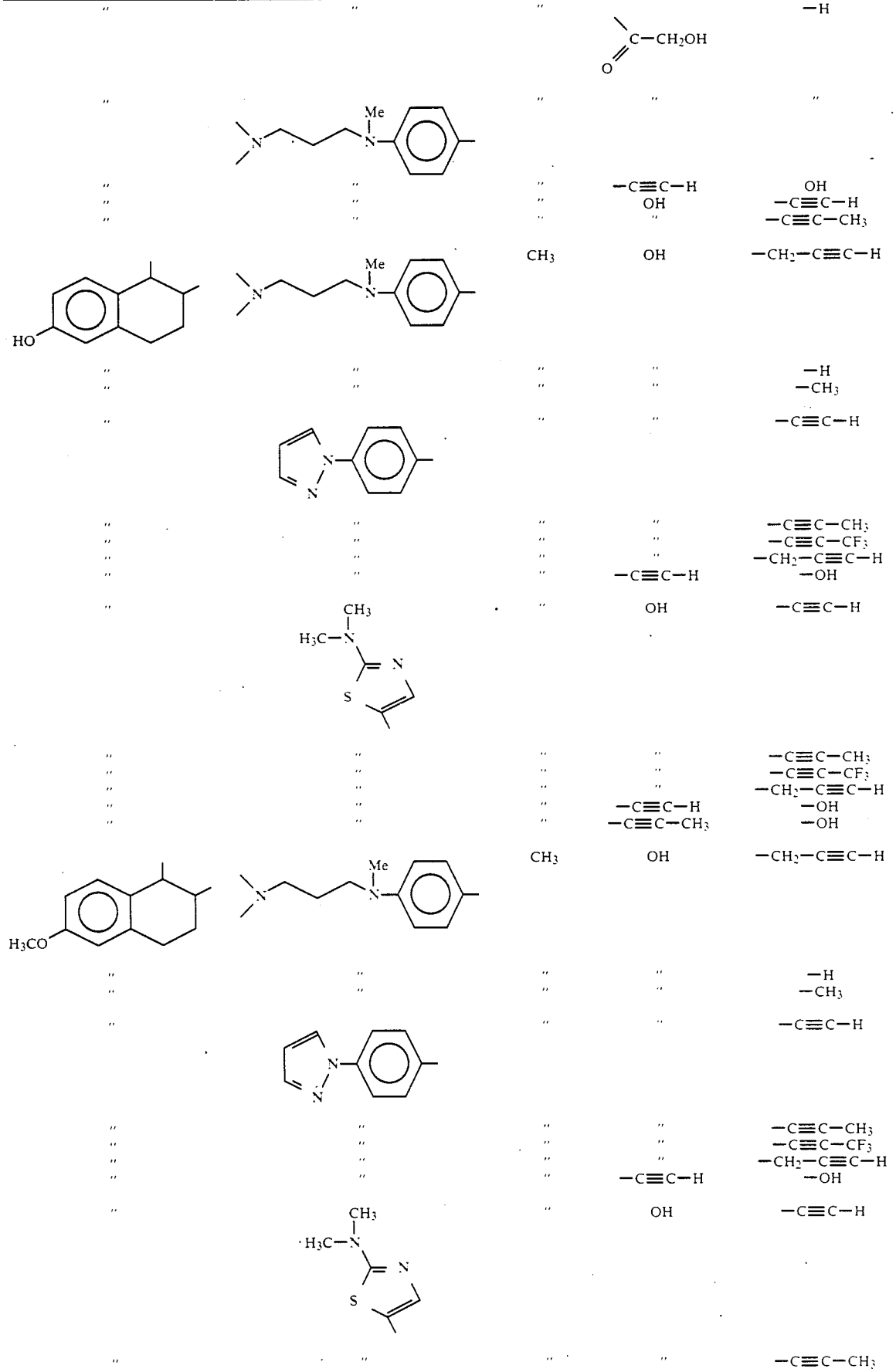

-continued

| | | | | | −C≡C−CF₃ |
| | | | | | −CH₂−C≡C−H |
| | | | | −C≡C−H | −OH |
| | | | | −C≡C−CH₃ | −OH |
| 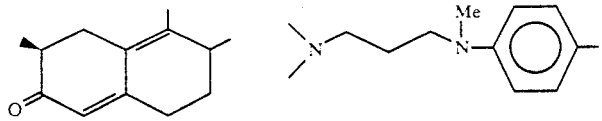 |  | | CH₃ | OH | −CH₂−C≡C−H |
| | | | | | −H |
| | | | | | −CH₃ |
| | 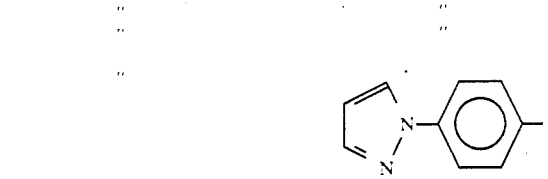 | | | | −C≡C−H |
| | | | | | −C≡C−CH₃ |
| | | | | | −C≡C−CF₃ |
| | | | | | −CH₂−C≡C−H |
| | | | | −C≡C−H | −OH |
| | 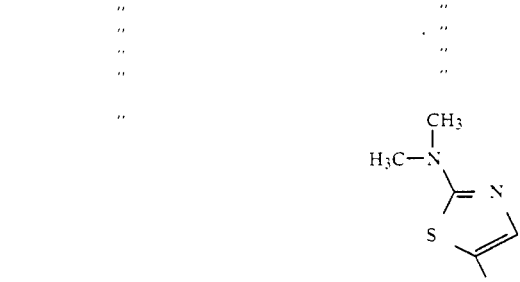 | | | OH | −C≡C−H |
| | | | | | −C≡C−CH₃ |
| | | | | | −C≡C−CF₃ |
| | | | | | −CH₂−C≡C−H |
| | | | | −C≡C−H | −OH |
| | | | | −C≡C−CH₃ | −OH |
| 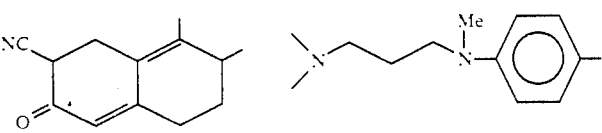 |  | | CH₃ | OH | −CH₂−C≡C−H |
| | | | | | −H |
| | | | | | −CH₃ |
| |  | | | | −C≡C−H |
| | | | | | −C≡C−CH₃ |
| | | | | | −C≡C−CF₃ |
| | | | | | −CH₂−C≡C−H |
| | | | | −C≡C−H | −OH |
| | 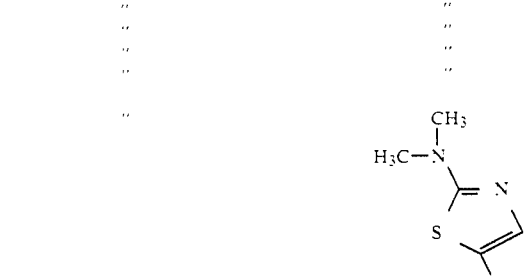 | | | OH | −C≡C−H |
| | | | | | −C≡C−CH₃ |
| | | | | | −C≡C−CF₃ |
| | | | | −CH₂−C≡C−H | |
| | | | | −C≡C−H | −OH |
| | | | | −C≡C−CH₃ | −OH |

The following compounds are additional compounds falling within the scope of the invention:

A) compounds of the formula

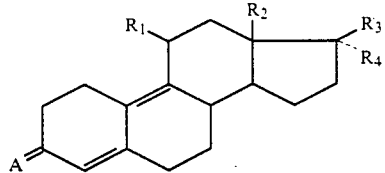

wherein the A, $R_1$, $R_2$, $R_3$ and $R_4$ substituents are indicated in the following Table.

| A | $R_1$ | $R_2$ | $R_3$ | $R_4$ |
|---|---|---|---|---|
| O | (4-dimethylaminophenyl) | $CH_3$ | OH | $-C\equiv C-H$ |
| " | " | " | " | $-C\equiv C-CF_3$ |
| " | " | " | " | $-C\equiv C-CH_2CH_3$ |
| " | " | " | " | $-CH_2-C\equiv C-H$ |
| " | " | " | " | $-C\equiv C-SiMe_3$ |
| " | " | " | $-C\equiv C-H$ | OH |
| " | " | " | $-C\equiv C-SiMe_3$ | OH |
| " | " | $CH_2CH_3$ | OH | $-C\equiv C-H$ |
| " | " | " | OH | $-C\equiv C-CH_3$ |
| " | " | " | OH | $-CH_2-C\equiv C-H$ |
| " | " | $CH_3$ | $-C(=O)-CH_2OH$ | H |
| HO—N=(E) | " | " | " | OH |
| " | " | " | OH | $-C\equiv C-H$ |
| " | " | " | " | $-C\equiv C-CH_3$ |
| " | " | " | $-C\equiv C-H$ | OH |
| HO—N=(Z) | " | " | OH | $-CH_2-C\equiv C-H$ |
| " | " | " | OH | $-C\equiv C-H$ |
| " | " | " | " | $-C\equiv C-CH_3$ |
| " | " | " | " | $-CH_2-C\equiv C-H$ |
| " | " | " | $-C\equiv C-H$ | OH |
| O | (indolin-5-yl) | " | OH | $-C\equiv C-H$ |
| " | " | " | " | $-C\equiv C-CF_3$ |
| " | " | " | " | $-CH_2-C\equiv C-H$ |
| " | " | " | " | $-C\equiv C-CH_2CH_3$ |
| " | " | " | " | $-C\equiv C-Cl$ |
| " | " | " | " | $-C\equiv C-SiMe_3$ |
| " | " | " | $-C\equiv C-H$ | OH |
| " | " | " | $-C\equiv C-SiMe_3$ | OH |
| O | (indolin-5-yl) | $CH_2CH_3$ | OH | $-C\equiv C-H$ |
| " | " | " | " | $-C\equiv C-CH_3$ |
| " | " | " | " | $-CH_2-C\equiv C-H$ |
| " | " | $CH_3$ | $-C(=O)-CH_2OH$ | —H |
| " | " | " | " | —OH |

-continued

| A | R₁ | R₂ | R₃ | R₄ |
|---|----|----|----|----|
| ,, | ,, | ,, | $-\underset{\underset{O}{\|}}{C}-CH_3$ | —H |
| HO—N=(E) | ,, | ,, | —OH | —C≡C—H |
| ,, | ,, | ,, | ,, | —C≡C—CH₃ |
| ,, | ,, | ,, | ,, | —C≡C—CH₂CH₃ |
| ,, | ,, | ,, | ,, | —CH₂—C≡C—H |
| ,, | ,, | ,, | —C≡C—H | —OH |
| ,, | ,, | ,, | $-\underset{\underset{O}{\|}}{C}-CH_2OH$ | H |
| HO—N=(Z) | ,, | ,, | ,, | ,, |
| ,, | ,, | ,, | OH | —C≡C—H |
| ,, | ,, | ,, | ,, | —C≡C—CH₃ |
| ,, | ,, | ,, | ,, | —C≡C—CH₂CH₃ |
| ,, | ,, | ,, | ,, | —CH₂—C≡C—H |
| ,, | ,, | ,, | —C≡C—H | —OH |
| O | (N-oxide indoline structure) | ,, | ,, | ,, |
| ,, | ,, | ,, | OH | —C≡C—H |
| ,, | ,, | ,, | ,, | —C≡C—CF₃ |
| ,, | ,, | ,, | ,, | —C≡C—Cl |
| ,, | ,, | ,, | ,, | —C≡C—CH₂CH₃ |
| ,, | ,, | ,, | ,, | —CH₂—C≡C—H |
| ,, | ,, | ,, | ,, | —C≡C—SiMe₃ |
| ,, | ,, | ,, | $-\underset{\underset{O}{\|}}{C}-CH_2OH$ | —H |
| HO—N=(E) | (N-oxide indoline structure) | CH₃ | OH | —C≡C—H |
| ,, | ,, | ,, | ,, | —C≡C—CH₃ |
| ,, | ,, | ,, | ,, | —CH₂—C≡C—H |
| ,, | ,, | ,, | —C≡C—H | —OH |
| HO—N=(Z) | ,, | ,, | OH | —C≡C—H |
| ,, | ,, | ,, | ,, | —C≡C—CH₃ |
| ,, | ,, | ,, | ,, | —CH₂—C≡C—H |
| O | (N,N-dimethylaminophenyl structure) | ,, | ,, | —C≡C—CH₂CH₃ |
| ,, | ,, | ,, | ,, | —C≡C—CF₃ |
| ,, | ,, | ,, | —C≡C—SiMe₃ | —OH |
| ,, | ,, | ,, | $-\underset{\underset{O}{\|}}{C}-CH_2OH$ | —H |
| ,, | ,, | ,, | ,, | —OH |
| ,, | ,, | ,, | $-\underset{\underset{O}{\|}}{C}-CH_3$ | —H |
| ,, | ,, | CH₂CH₃ | OH | —C≡C—H |
| ,, | ,, | ,, | ,, | —C≡C—CH₃ |
| ,, | ,, | ,, | ,, | —C≡C—Cl |
| ,, | ,, | ,, | ,, | —C≡C—CH₂—CH₃ |
| ,, | ,, | ,, | ,, | —C≡C—SiMe₃ |
| ,, | ,, | ,, | ,, | —CH₂—C≡C—H |

| A | R₁ | R₂ | R₃ | R₄ |
|---|---|---|---|---|
| " | " | " | −C(=O)−CH₂OH | −H |
| HO−N=(E) | " | CH₃ | −C≡C−H | −OH |
| " | " | " | −C(=O)−CH₂OH | −H |
| HO−N=(Z) | " | " | OH | −CH₂−C≡C−H |
| HO−N=(Z) | 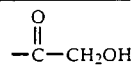 (Me₂N−C₆H₄−) | CH₃ | −C≡C−H | −OH |
| " | " | " | −C(=O)−CH₂OH | −H |
| O | 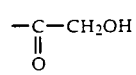 (Me₂N(O)−C₆H₄−) | " | " | " |
| " | " | " | −C≡C−H | −OH |
| " | " | " | OH | −CH₂−C≡C−H |
| " | " | " | " | −C≡C−CH₂CH₃ |
| " | " | " | " | −C≡C−CF₃ |
| " | " | " | " | −C≡C−H |
| " | " | " | " | −C≡C−SiMe₃ |
| HO−N=(E) | " | " | OH | −C≡C−H |
| " | " | " | " | −C≡C−CH₃ |
| " | " | " | " | −C≡C−CH₂CH₃ |
| " | " | " | " | −C≡C−Cl |
| " | " | " | " | −C≡C−SiMe₃ |
| " | " | " | " | −CH₂−C≡C−H |
| HO−N=(Z) | " | " | −C≡C−H | −OH |
| " | " | " | OH | −C≡C−H |
| " | " | " | " | −C≡C−CH₃ |
| " | " | " | " | −C≡C−CH₂−CH₃ |
| " | " | " | " | −C≡C−Cl |
| " | " | " | " | −C≡C−SiMe₃ |
| " | " | " | " | −CH₂−C≡C−H |
| O | 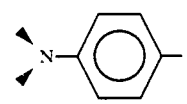 (Me₂N−C₆H₄−C₆H₄−) | " | OH | −C≡C−H |
| " | " | " | " | −C≡C−CF₃ |
| " | " | " | " | −C≡C−CH₃ |
| " | " | " | " | −C≡C−Cl |
| O | 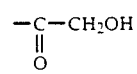 | CH₃ | OH | −CH₂−C≡C−H |
| " | " | " | " | −H |
| " | " | " | −C≡C−H | −OH |
| " | " | " | −C(=O)−CH₂OH | −H |
| " | 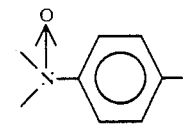 (EtMeN−C₆H₄−C₆H₄−) | " | " | " |
| " | " | " | OH | −C≡C−H |

-continued
| A | R₁ | R₂ | R₃ | R₄ |
|---|----|----|----|----|
| ″ | ″ | ″ | ″ | —C≡C—CH₃ |
| ″ | ″ | ″ | ″ | —C≡C—Cl |
| ″ | ″ | ″ | ″ | —CH₂—C≡C—H |
| ″ | ″ | ″ | —C≡C—H | —OH |
| ″ | 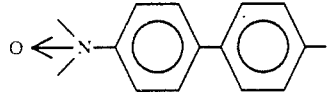 | ″ | ″ | ″ |
| ″ | ″ | ″ | OH | —C≡C—H |
| ″ | ″ | ″ | ″ | —C≡C—CF₃ |
| ″ | ″ | ″ | ″ | —C≡C—CH₃ |
| ″ | ″ | ″ | ″ | —CH₂—C≡C—H |
| ″ | ″ | ″ | ″ | —H |
| ″ | 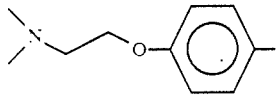 | ″ | ″ | —C≡C—H |
| ″ | ″ | ″ | ″ | —CH₂—C≡C—H |
| ″ | ″ | ″ | —C≡C—H | —OH |
| ″ | ″ | ″ | 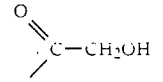 | —H |
| ″ | 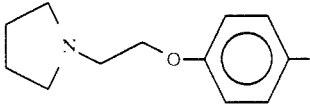 | ″ | ″ | ″ |
| ″ | ″ | ″ | —C≡C—H | —OH |
| ″ | ″ | ″ | —OH | —C≡C—H |
| ″ | ″ | ″ | ″ | —C≡C—CH₃ |
| ″ | ″ | ″ | ″ | —CH₂—C≡C—H |
| ″ | 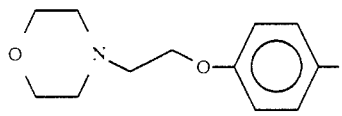 | ″ | —OH | —C≡C—H |
| ″ | ″ | ″ | ″ | —C≡C—CH₃ |
| O | 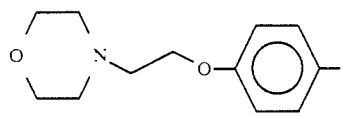 | CH₃ | —OH | —CH₂—C≡C—H |
| ″ | ″ | ″ | —C≡C—H | —OH |
| ″ | ″ | ″ | 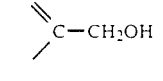 | —H |
| ″ | 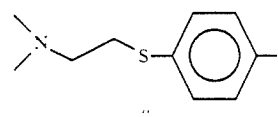 | ″ | ″ | ″ |
| ″ | ″ | ″ | —C≡C—H | OH |
| ″ | ″ | ″ | OH | —C≡C—CF₃ |
| ″ | ″ | ″ | OH | —C≡C—H |
| ″ | ″ | ″ | ″ | —CH₂—CH=CH₂ |
| ″ | ″ | ″ | ″ | CH₂—C≡C—H |
| ″ | ″ | ″ | ″ | —CH₂' |

-continued

| A | R₁ | R₂ | R₃ | R₄ |
|---|----|----|----|-----|
| " | " | " | $\underset{O}{\overset{}{C}}-CH_3$ | —CH₃ |
| " | " | " | " | —CH₂—CN |
| HO—N=(E) | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |
| " | " | " | " | —H |
| " | " | " | $\underset{O}{\overset{}{C}}-CH_2OH$ | " |
| HO—N=(Z) | " | " | " | " |
| " | " | " | —C≡C—H | —OH |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —CH₂—C≡C—H |
| O | " | CH₂CH₃ | " | —C≡C—H |
| " | " | " | " | —C≡C—CH₃ |
| O | 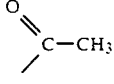 | CH₂CH₃ | OH | —CH₂—C≡C—H |
| " | " | " | " | —CH₂—CH=CH₂ |
| " | " | " | " | —CH₃ |
| " | " | " | $\underset{O}{\overset{}{C}}-CH_3$ | |
| " | " | " | $\underset{O}{\overset{}{C}}-CH_2OH$ | —H |
| " | " | " | —C≡C—H | —OH |
| " | 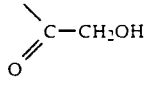 | CH₃ | OH | —C≡C—H |
| " | " | " | " | —C≡C—CH₃ |
| " | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |
| " | " | " | —C≡C—H | —OH |
| " | " | " | " | —H |
| " | " | " | $\underset{O}{\overset{}{C}}-CH_2OH$ | |
| " | " | " | $\underset{O}{\overset{}{C}}-CH_3$ | —CH₃ |
| " | " | " | $\underset{O}{\overset{}{C}}-CH_3$ | —H |

-continued

| A | R₁ | R₂ | R₃ | R₄ |
|---|---|---|---|---|
| " | morpholine-N-CH₂CH₂-S-C₆H₄- | " | " | |
| " | " | " | " | —CH₃ |
| " | " | " | " | —H |
| | | | $\underset{\parallel}{O}$ C—CH₂OH | |
| " | " | " | —C≡C—H | —OH |
| " | " | " | OH | —C≡C—H |
| " | " | " | " | —C≡C—CH₃ |
| " | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |
| " | Me₃Si—CH₂—N(CH₃)—C₆H₄— | " | " | —C≡C—H |
| " | " | " | " | —C≡C—CH₃ |
| " | " | " | " | —CH₂—C≡C—H |
| O | Me₃Si—CH₂—N(CH₃)—C₆H₄— | CH₃ | —C≡C—H | —OH |
| " | " | " | $\underset{\parallel}{O}$ C—CH₂OH | —H |
| " | Me₃Si—CH₂—N⁺(O⁻)(CH₃)—C₆H₄— | " | OH | —C≡C—H |
| " | " | " | " | —C≡C—CH₃ |
| " | " | " | " | —CH₂—C≡C—H |
| " | " | " | —C≡C—H | —OH |
| " | " | " | $\underset{\parallel}{O}$ C—CH₂OH | —H |
| " | " | " | OH | —C≡C—CH₃ |
| " | 1-(N,N-dimethylamino)naphthalen-5-yl | " | " | |
| " | " | " | " | —CH₂—C≡C—H |
| " | " | " | " | —C≡C—H |
| " | 2-(N,N-dimethylamino)-6-naphthyl | " | " | |
| " | " | " | " | —C≡C—CH₃ |
| " | " | " | " | —C≡C—Cl |
| " | " | " | " | —CH₂—C≡C—H |

-continued

| A | $R_1$ | $R_2$ | $R_3$ | $R_4$ |
|---|---|---|---|---|
| " | " | " | $-C\equiv C-H$ | $-OH$ |
| " | " | " | $\underset{O}{\overset{\parallel}{C}}-CH_2OH$ | $-H$ |
| " | [N-oxide dimethylamino naphthyl group] | " | | |
| " | " | " | $-C\equiv C-H$ | $-OH$ |
| " | " | " | $-OH$ | $-C\equiv C-H$ |
| " | " | " | " | $-C\equiv C-CH_3$ |
| " | " | " | " | $-C\equiv C-Cl$ |
| " | " | " | " | $-CH_2-C\equiv C-H$ |
| " | $Me_3Si\ CH_2-$ | " | " | $-C\equiv C-H$ |
| " | " | " | " | $-C\equiv C-CH_3$ |
| " | " | " | " | $-CH_2-C\equiv C-H$ |
| $HO-N=(E)$ | " | " | $-C\equiv C-H$ | $-OH$ |
| " | " | " | $OH$ | $-C\equiv C-H$ |
| " | " | " | " | $-C\equiv C-CH_3$ |
| $HO-N=(E)$ | $Me_3Si\ CH_2-$ | $CH_3$ | $OH$ | $-CH_2-C\equiv C-H$ |
| $HO-N=(Z)$ | " | " | $-C\equiv C-H$ | $-OH$ |
| " | " | " | $OH$ | $-C\equiv C-H$ |
| " | " | " | " | $-C\equiv C-CH_3$ |
| " | " | " | " | $-CH_2-C\equiv C-H$ |
| $O$ | [dimethylaminopropoxy tolyl group] | " | " | $-C\equiv C-CH_3$ |
| " | " | " | $\underset{O}{\overset{\parallel}{C}}-CH_2OH$ | $-H$ |
| " | [dimethylaminopropylthio tolyl group] | " | " | " |
| " | " | " | $OH$ | $-C\equiv C-H$ |
| " | " | " | " | $-C\equiv C-CH_3$ |
| " | " | " | " | $-CH_2-C\equiv C-H$ |
| " | " | " | " | $-CH_2-CH=CH_2$ |
| " | " | " | " | $-CH_2CN$ |
| " | " | " | $-C\equiv C-H$ | $-OH$ |
| " | " | " | $\underset{O}{\overset{\parallel}{C}}-CH_2OH$ | $-H$ |
| " | " | " | $\underset{O=C-CH_3}{\overset{\mid}{\phantom{C}}}$ | $-CH_3$ |
| " | " | " | $OH$ | $-H$ |
| " | " | " | $OH$ | $-C\equiv C-H$ |
| " | [dimethylamino-ethyl-N-methyl-anilino tolyl group] | " | " | " |
| " | " | " | " | $-C\equiv C-CF_3$ |
| " | " | " | " | $-C\equiv C-CH_2CH_3$ |
| " | " | " | " | $-C\equiv C-Cl$ |
| " | " | " | " | $-CH_2-C\equiv C-H$ |

-continued

| A | R₁ | R₂ | R₃ | R₄ |
|---|---|---|---|---|
| " | " | " | −C≡C−H | −OH |
| " | " | " | 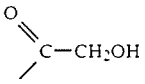 | −H |
| " | " | " | 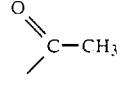 | −CH₃ |
| " | " | CH₂CH₃ | OH | −C≡C−H |
| " | " | " | " | −C≡C−CH₃ |
| " | " | " | " | −CH₂−C≡C−H |
| O | 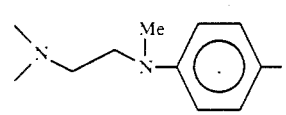 | CH₂CH₃ | −C≡C−H | −OH |
| " | " | " | 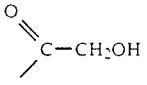 | −H |
| " | 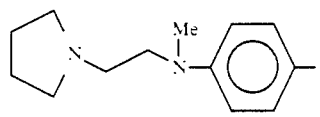 | CH₃ | OH | −C≡C−H |
| " | " | " | " | −C≡C−CH₃ |
| " | " | " | " | −CH₂−C≡C−H |
| " | " | " | −C≡C−H | −OH |
| " | " | " | 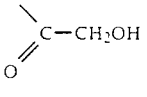 | −H |
| " | 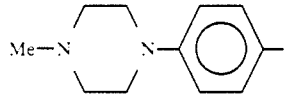 | " | " | " |
| " | " | " | −C≡C−H | −OH |
| " | " | " | " | −C≡C−H |
| " | " | " | " | −CH₂−C≡C−H |
| " | " | " | " | −CH₂−CH=CH₂ |
| " | " | " | " | −CH₂CN |
| " | 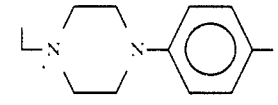 | " | " | −C≡C−H |
| " | " | " | " | −C≡C−CH₃ |
| " | " | " | " | −CH₂−C≡C−H |
| " | " | " | " | −CH₂−CH=CH₂ |
| " | " | " | " | −CH₂−CN |
| " | " | " | −C≡C−H | −OH |
| " | 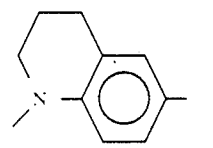 | " | −OH | −C≡C−H |
| " | " | " | " | −C≡C−CH₃ |
| " | " | " | " | −CH₂−C≡C−H |
| " | " | " | −C≡C−H | −OH |

-continued

| A | R₁ | R₂ | R₃ | R₄ |
|---|----|----|----|----|
| " | " | " |  | —H |
|   |   |   | \C—CH₂OH (C=O) |  |
| " | Me₂N-CH₂CH₂CH₂-N(Me)-C₆H₄- | " | " | " |
| " | " | " | —C≡C—H | OH |
| " | " | " | OH | —C≡C—H |
| " | " | " | " | —C≡C—CH₃ |
| O | Me₂N-CH₂CH₂CH₂-N(Me)-C₆H₄- | CH₃ | OH | —CH₂—C≡C—H |
| " | " | " | " | —H |
| " | " | " | " | —CH₃ |
| " | pyridazinyl-C₆H₄- | " | " | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| " | (H₃C)(H₃CN)C=N-thiazolyl- | " | OH | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| " | " | " | —C≡C—CH₃ | —OH |

B) compounds of the formula

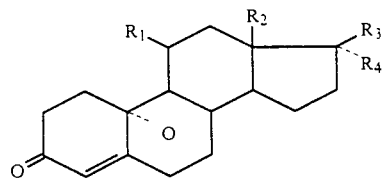

wherein R₁, R₂, R₃ and R₄ have the definitions in the following Table.

| R₁ | R₂ | R₃ | R₄ |
|----|----|----|----|
| Et(Me)N-C₆H₄- | CH₃ | OH | —C≡C—H |
| " | " | " | —C≡C—CH₃ |
| " | " | " | —C≡C—CF₃ |
| " | " | " | —CH₂CH₃ |
| " | " | " | —CH₂—C≡C—H |

-continued
| R₁ | R₂ | R₃ | R₄ |
|---|---|---|---|
| 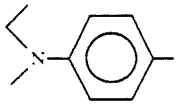 | CH₃ | —C≡C—H | —OH |
| 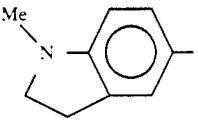 | " | OH | —C≡C—H |
| " | " | " | —C≡C—CH₃ |
| " | " | " | —C≡C—CF₃ |
| " | " | " | —C≡C—CH₂CH₃ |
| " | " | " | —CH₂—C≡C—H |
| " | " | " | —H |
| " | " | " | —CH₂CH₃ |
| " | " | —C≡C—H | —OH |
| " | " | 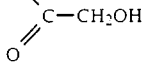 | —H |
| " | " | 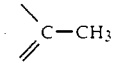 | —CH₃ |
| 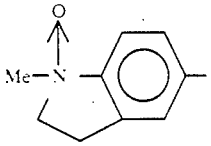 | " | " | " |
| " | " | OH | —C≡C—H |
| " | " | " | —C≡C—CH₃ |
| " | " | " | —C≡C—CF₃ |
| " | " | " | —CH₂CH₃ |
| " | " | " | —CH₂—C≡C—H |
| " | " | —C≡C—H | —OH |
| " | " | OH | H |
| 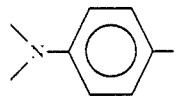 | " | 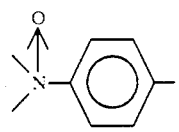 | CH₃ |
| " | " | OH | —C≡C—H |
| " | " | " | —C≡C—CH₃ |
| " | " | " | —C≡C—CF₃ |
| " | " | " | —CH₂CH₃ |
| " | " | " | —CH₂—C≡C—H |
| 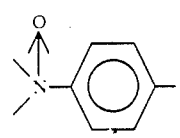 | " | OH | —C≡C—H |
| " | " | " | —C≡C—CH₃ |
| " | CH₃ | OH | —C≡C—CF₃ |
| " | " | " | —CH₂—CH₃ |
| " | " | " | —CH₂—C≡C—H |
| " | " | " | H |
| " | " | " | CH₃ |

-continued

| R₁ | R₂ | R₃ | R₄ |
|----|----|----|----|
| " | " | —C≡C—H | OH |

In the following examples there are described several preferred embodiments to illustrate the invention. However, it is to be understood that the invention is not intended to be limited to the specific embodiments.

EXAMPLE 1

2,2-dimethyl-11β-(4-dimethylaminophenyl)-17α-(prop-1-ynyl)-Δ$^{4,9}$-estradiene-17β-ol-3-one STEP A: 11β-(4-dimethylaminophenyl)-17α-(prop-1-ynyl)-17β-(2RS-tetrahydropyranyloxy)-Δ$^{4,9}$-estradiene-3-one 570 mg of p-toluene sulfonic acid were added to a solution of 1.075 g of 11β-(4-dimethylaminophenyl)-17α-(prop-1-ynyl)-Δ$^{4,9}$-estradiene-17β-ol-3-one [prepared in Example 1 of EPC Application Ser. No. 57,115] in 10 ml of tetrahydrofuran and 2 ml of 3,4-dihydro-pyran and the mixture was stirred at room temperature for one hour. 1 ml of triethylamine was added to the mixture which was then diluted with ethyl acetate. The organic phase was washed with aqueous saturated sodium bicabonate solution, dried and evaporated to dryness under reduced pressure to obtain 2 g of raw 11β-(4-dimethylaminophenyl)-17α-(prop-1-ynyl)-17β-(2RS-tetrahydropyranyloxy)-Δ$^{4,9}$-estradiene-3-one in the form of a yellow oil.

STEP B: 2,2-dimethyl-11β-(4-dimethylaminophenyl)-17α-(prop-1-ynyl)-17β-(2RS tetrahydropyranyloxy)-Δ$^{4,9}$-estradiene-3-one A solution of the product of Step A in 15 ml of anhydrous tetrahydrofuran was cooled to −60° C. and over 5 to 6 minutes 1 ml and 3 ml of a solution of 2M potassium tert.-butylate in tetrahydrofuran and 3 ml of a solution of 0.38 ml of methyl iodide in tetrahydrofuran were alternatively added thereto. The mixture was stirred for another five minutes and one ml of triethylamine was added thereto. The temperature was allowed to rise to room temperature and the mixture was evaporated to dryness to obtain 2,2-dimethyl-11β-(4-dimethylaminophenyl)-17α-(prop-1-ynyl)-17β-(2RS tetrahydropyranyloxy)-Δ$^{4,9}$-estradiene-3-one.

STEP C: 2,2-dimethyl-11β-(4-dimethylaminophenyl)-17α-(prop-1-ynyl)-Δ$^{4,9}$-estradiene-17β-ol-3-one 2.5 ml of 5N hydrochloric acid were added to a solution of the product of Step B in 10 ml of methanol and after standing for 15 minutes at room temperature, the mixture was diluted with water. The methanol was distilled off under reduced pressure and 2.5 ml of concentrated ammonium hydroxide were added thereto. The mixture was vacuum filtered and the product was washed with water and dissolved in ethyl acetate. The organic phase was dried and evaporated to dryness and the 1.5 g of residue were chromatographed over silica gel. Elution with a 9-1 benzene-ethyl acetate mixture yielded 990 mg of product which was crystallized from heptane. The mixture was vacuum filtered and the product was washed and dried to obtain 980 mg of 2,2-dimethyl-11β-(4-dimethylaminophenyl)-17α-(prop-1-ynyl)-Δ$^{4,9}$-estradiene-17β-ol-3-one melting at 170°–172° C.

A 2.2 g sample of the said product were dissolved in methylene chloride and the mixture was filtered. The filtrate was evaporated to dryness and the residue was dissolved in 10 ml of refluxing isopropyl ether and the solution cooled and crystallization was induced by scraping. The mixture stood at 5° C. and was then vacuum filtered. The product was washed and dried to obtain 1.88 g of the pure product melting at 171° C. and having a specific rotation of $[\alpha]_D^{20} = +183.5° \pm 3.5°$ (c=1% in chloroform).

| Analysis: C₃₁H₃₉NO₂ | | | |
|---|---|---|---|
| Calculated: | % C 81.36 | % H 8.59 | % N 3.06 |
| Found: | 81.1 | 8.8 | 3.2 |

EXAMPLE 2

11β-(4-dimethylaminophenyl)-17α-(prop-1-ynyl)-Δ$^{1,3,5(10)}$-estratriene-3,17β-diol and its 17β-acetoxy derivative 2 ml of 98% acetic anhydride and 1 ml of acetyl bromide were added dropwise under a nitrogen atmosphere to a solution of 2 g of 11β-(4-dimethylaminophenyl)-17α-(prop-1-ynyl)-Δ$^{4,9}$-estradiene-17β-ol-3-one in 20 ml of dry methylene chloride and the mixture was stirred at room temperature for one hour. 100 ml of aqueous sodium bicarbonate were added to the mixture which was stirred for 30 minutes. The decanted aqueous phase was extracted with methylene chloride and the combined organic phases were dried and evaporated to dryness. The 2.65 g of residue were dissolved in 25 ml of methanol and 2.6 ml of sodium hydroxide solution were added thereto at room temperature under nitrogen. The mixture was stirred for 45 minutes and was then acidified with 14 ml of 2N hydrochloric acid. The mixture was made alkaline by addition of ammonium hydroxide and was extracted with methylene chloride. The organic phase was washed with water, dried and evaporated to dryness under reduced pressure. The 2.3 g of residue were chromatographed over silica gel and eluted with an 8-2 methylene chloride-ethyl acetate mixture to obtain 430 mg of 11β-(4-dimethylaminophenyl)-17α-(prop-1-ynyl)-17β-acetoxy-Δ$^{1,3,5(10)}$-estratriene-3-ol with an Rf=0.58 and 800 mg of 11β-(4-dimethylaminophenyl)-17α-(prop-1-ynyl)-Δ$^{1,3,5(10)}$-estratriene-3,17β-diol with an Rf=0.36.

The 430 mg of the 17β-acetoxy compound were dissolved in 4 ml of refluxing methylene chloride and the solution was filtered. 4 ml of isopropyl ether were added to the filtrate and the mixture was evaporated to a small volume and iced. The mixture was vacuum filtered and the product was washed with isopropyl ether and dried at 60° C. under reduced pressure to obtain 370 mg of the 17β-acetoxy compound melting at 236° C. and having a specific rotation of $[\alpha]_D^{20} = 194.5° \pm 3°$.

| Analysis: C₃₁H₃₇NO₃ | | | |
|---|---|---|---|
| Calculated: | % C 78.95 | % H 7.91 | % N 2.97 |
| Found: | 78.7 | 7.9 | 3.0 |

880 mg of the 3,17β-diol compound from 2 preparations were dissolved in 12 ml of refluxing methylene chloride and the mixture was filtered. 12 ml of isopropyl ether were added to the filtrate and the mixture was concentrated to a volume of 5 ml. The mixture was iced and vacuum filtered and the product was washed with iced isopropyl ether and dried to obtain 770 mg of the 3,17β-diol compound melting at 246° C. and having a specific rotation of $[\alpha]_D^{20} = -188.5° \pm 2.5°$.

| Analysis: $C_{29}H_{35}NO_2$ | | | |
|---|---|---|---|
| Calculated: | % C 81.08 | % H 8.21 | % N 3.26 |
| Found: | 81.1 | 8.2 | 3.1 |

EXAMPLE 3

2-(acetyloxy methylene)-11β-(4-dimethylaminophenyl)-17α-(prop-1-ynyl)-Δ$^{4,9}$-estradiene-17β-ol-3-one STEP A: 2-hydroxy methylene-11β-(4-dimethylaminophenyl)-17α-(prop-1-ynyl)-Δ$^{4,9}$-estradiene-17β-ol-3-one 5 g of a 55.5% suspension of sodium hydride in oil were washed three times with 50 ml of diethyl oxide to remove surnagent and then 100 ml of dry benzene and 5 g of 11β-(4-dimethylaminophenyl)-17α-(prop-1-ynyl)-Δ$^{4,9}$-estradiene-17β-ol-3-one were added thereto. 9.4 ml of ethyl formate were added thereto dropwise and the mixture was stirred at room temperature for 20 hours and was then poured into 200 ml of water. The mixture was washed three times with 50 ml of diethyl oxide and the washliquids were extracted twice with 50 ml of water. The combined aqueous phases were adjusted to a pH of 3.2 by addition of 70 ml of 2N hydrochloric acid and then made basic by addition of 40 ml of aqueous saturated sodium bicarbonate solution. The mixture was extracted once with 100 ml and then three times with 50 ml of diethyloxide. The combined organic phases were washed with 50 ml of aqueous saturated sodium chloride solution, dried and evaporated to dryness under reduced pressure to obtain 5.2 g of raw 2-hydroxy methylene-11β-(4-dimethylaminopropyl)-17α-(prop-1-ynyl)-Δ$^{4,9}$-estradiene-17β-ol-3-one which was used as is for the next step.

STEP B: 2-(acetyloxymethylene)-11β-(4-dimethylaminophenyl)-17α-(prop-1-ynyl)-Δ$^{4,9}$-estradiene-17β-ol-3-one 0.2 ml of pyridine and then 0.16 ml of acetyl chloride were added at 5° C. to a solution of 460 mg of the product of Step A in 20 ml of dry chloroform and the mixture stood in an ice bath for one hour after which 10 ml of aqueous sodium bicarbonate solution were added thereto. The mixture was stirred for 5 minutes and the decanted aqueous phase was washed with water, dried and evaporated to dryness under reduced pressure. The 510 mg of residue were dissolved in 10 ml of methylene chloride and 50 mg of activated carbon were added thereto. The mixture was filtered and the filtrate was evaporated to dryness to obtain 490 mg of product. The latter was empasted with petroleum ether and the product was washed with petroleum ether and then twice with 5 ml of isopropyl ether and dried at 50° C. under reduced pressure to obtain 380 mg of 2-(acetyloxymethylene)-11β-(4-dimethylaminophenyl)-17α-(prop-1-ynyl)-Δ$^{4,9}$-estradiene-17β-ol-3-one with a specific rotation of $[\alpha]_D^{20} = +182° \pm 3°$ (c = 1% in chloroform).

| Analysis: $C_{32}H_{39}NO_4$ | | | |
|---|---|---|---|
| Calculated: | % C 76.92 | % H 7.46 | % N 2.8 |
| Found: | 77.0 | 7.6 | 2.6 |

EXAMPLE 4

2-(4-morpholinylmethylene)-11β-(4-dimethylaminophenyl)-17α-(prop-1-ynyl)-Δ$^{4,9}$-estradiene-17β-ol-3-one 0.24 ml of morpholine were added to a solution of 1.065 g of 2-hydroxymethylene-11β-(4-dimethylaminophenyl)-17α-(prop-1-ynyl)-Δ$^{4,9}$-estradiene-17β-ol-3-one in 10 ml of methanol and the mixture was heated to 55° C. for one hour and then evaporated to dryness under reduced pressure at 50° C. The 1.25 g of residue was chromatographed over alumina and eluted with a 70-30-1 cyclohexane-acetone-triethylamine mixture to obtain 1.06 g of 2-(4-morpholinylmethylene)-11β-(4-dimethylaminophenyl)-17α-(prop-1-ynyl)-Δ$^{4,9}$-estradiene-17β-ol-3-one with a Rf = 0.4, and with specific rotation of $[\alpha]_D^{20} = +263° \pm 4.5°$ (c = 0.7% in chloroform).

EXAMPLE 5

2α-methyl-11β-(4-dimethylaminophenyl)-17α-(prop-1-ynyl)-Δ$^{4,9}$-estradiene-17β-ol-3-one and its 2β-isomer A solution of 0.82 ml of cyclohexyl isopropylamine in 5 ml of tetrahydrofuran was slowly introduced at −70° C. under argon to a mixture of 3 ml of 1.6M of butyllithium in hexane and 5 ml of tetrahydrofuran and after standing for 10 minutes, a solution of 2.2 g of 11β-(4-dimethylaminophenyl)-17β-(2RS tetrahydropyranyloxy)-17α-(prop-1-ynyl)-Δ$^{4,9}$-estradiene-3-one in 8 ml of anhydrous tetrahydrofuran was added thereto at −70° C. The mixture stood at −70° C. for 10 minutes and then 0.5 ml of methyl iodide were added thereto. The mixture stood at −70° C. for 30 minutes and then was allowed to return to room temperature. One ml of triethylamine was added to the mixture which was diluted with ethyl acetate. The organic phase was washed with water, dried and evaporated to dryness to obtain 2.5 g of product. The latter was dissolved in 25 ml of methanol and 4 ml of 50% hydrochloric acid were added to the mixture which stood at room temperature for two hours and was diluted with water. The mixture was extracted with methylene chloride and the organic phase was washed with water, dried and evaporated under reduced pressure to obtain 2.04 g of a mixture of the two epimers of 2-methyl-11β-(4-dimethylaminophenyl)-17α-(prop-1-ynyl)-Δ$^{4,9}$-estradiene-17β-ol-3-one. The mixture was chromatographed over silica gel and eluted with a 2-3 ether-petroleum ether mixture to obtain 600 mg of the 2β-methyl and 345 mg of the 2α-methyl epimer and about 280 mg of the mixture. 1.1 g of the 2β-methyl isomer were crystallized from a methylene chloride-isopropyl ether to obtain 1.04 g of the 2β-methyl isomer melting at 211° C. 703 mg of 2α-methyl isomer were crystallized from a methylene chloride-isopropyl ether mixture to obtain 614 mg of the product melting at 204° C. Another crystallization of the product gave 560 mg of product melting at 205° C.

| Analysis: $C_{30}H_{37}NO_2$ | | | |
|---|---|---|---|
| Calculated: | | % C 81.22 | % H 8.40 | % N 3.15 |
| Found: | 2α-isomer | 81.2 | 8.5 | 3.2 |

-continued

| Analysis: C$_{30}$H$_{37}$NO$_2$ | | | |
|---|---|---|---|
| 2β-isomer | 80.8 | 8.6 | 3.2 |

EXAMPLE 6

11β-(3-methoxyphenyl)-17α-(prop-1-ynyl)-Δ$^{5(10)}$-estrene-17β-ol-3-one and
11β-(3-methoxyphenyl)-17α-(E)-(prop-1-enyl)-Δ$^{5(10)}$-estrene-17β-ol-3-one.

STEP A: 3,3-ethylenedioxy-11β-(3-methoxyphenyl)-17α-(prop-1-ynyl)-Δ$^9$-estrene-5α,17β-diol A mixture of 33.8 ml of 0.8M of 3-methoxyphenyl magnesium bromide in tetrahydrofuran and 285 mg of cuprous chloride was stirred under nitrogen at −20° C. for 15 minutes and a solution of 3.3 g of 3,3-ethylenedioxy-5α,10α-epoxy-17α-(prop-1-ynyl)-Δ$^{9(11)}$-estrene-17β-ol in 33 ml of tetrahydrofuran was added over 15 minutes. After a few minutes, 33 ml of tetrahydrofuran were added and the mixture was stirred at −20° C. for one hour and poured into a mixture of 15 g of ammonium chloride in 200 ml of iced water. The mixture was stirred for 30 minutes and was extracted three times with ether. The organic phase was washed with water, dried and evaporated to dryness under reduced pressure to obtain 5.3 g of residue. The latter was chromatographed over silica gel and eluted with a 95-5 methylene chloride-acetone mixture containing 1% of triethylamine to obtain 2.7 g of product with an Rf=0.30. 200 mg of product were crystallized from an isopropyl ether-methylene chloride mixture to obtain 165 mg of 3,3-ethylenedioxy-11β-(3-methoxyphenyl)-17α-(prop-1-ynyl)-Δ$^9$-estrene-5α,17β-diol in the form of white crystals melting at 228° C.

| Analysis: C$_{30}$H$_{38}$O$_5$ | | |
|---|---|---|
| | % C 75.28 | % H 8.80 |
| Calculated: | | |
| Found: | 75.3 | 8.1 |

STEP B: 11β-(3-methoxyphenyl)-17α-(prop-1-ynyl)-Δ$^{4,9}$-estradiene-17β-ol-3-one A mixture of 2.5 g of the product of Step A, 2.5 g of Redex resin and 125 ml of 95% ethanol was refluxed with stirring for 90 minutes and was cooled and filtered. The filter was rinsed with 95% ethanol and the filtrate was evaporated to dryness under reduced pressure to obtain 2.38 g of residue. The latter was chromatographed over silica gel and eluted with a 3-2 petroleum ether-ethyl acetate mixture. The 1.75 g of amorphous product was crystallized from an ether-cyclo-hexane mixture and was vaccum filtered. The product was rinsed with cyclohexane and dried under reduced pressure to obtain 1.42 of 11β-(3-methoxyphenyl)-17α-(prop-1-ynyl)-Δ$^{4,9}$-estradiene-17β-ol-3-one melting at 164° C.

| Analysis: C$_{28}$H$_{32}$O$_3$ | | |
|---|---|---|
| | % C 80.73 | % H 7.74 |
| Calculated: | | |
| Found: | 80.7 | 7.9 |

STEP C:
170 mg of cut lithium were added in small portions at −55° C. to a solution of 20 ml of tetrahydrofuran, 5 ml of tert.-butanol, 4.17 g of 11β-(3-methoxyphenyl)-17α-(prop-1-ynyl)-Δ$^{4,9}$-estradiene-17β-ol-3-one and 100 ml of liquid ammonia and after two hours at −55° C., 50 ml of aqueous ammonium chloride solution were slowly added thereto. The temperature was allowed to rise to room temperature and the mixture was extracted with ethyl acetate. The organic phase was washed with aqueous sodium chloride solution, dried and evaporated to dryness to obtain 4.3 g of resin. The latter was chromatographed over silica gel and eluted with a 7-3 cyclohexane-ethyl acetate mixture to obtain 380 mg of 11β-(3-methoxyphenyl)-17α-(E)-(prop-1-enyl)-5,(10)-estrene-17β-ol-3-one with a Rf=0.27 and a specific rotation of $[\alpha]_D^{20} = +10.5°\pm1°$ (c=1.2% in chloroform) and 2.65 g of 11β-(3-methoxyphenyl)-17α-(prop-1-ynyl)-Δ$^{5(10)}$-estrene-17β-ol-3-one with an Rf=0.25 and a specific rotation of $[\alpha]_D^{20} = -30°\pm1.5°$ (c=1% in chloroform).

| Analysis: 17α-(prop-1-enyl) C$_{28}$H$_{36}$O$_3$ | | |
|---|---|---|
| | % C 79.96 | % H 8.63 |
| Calculated: | | |
| Found: | 79.8 | 8.9 |

| Analysis: 17α-(prop-1-ynyl) C$_{28}$H$_{34}$O$_3$ | | |
|---|---|---|
| | % C 80.34 | % H 8.19 |
| Calculated: | | |
| Found: | 80.4 | 8.3 |

EXAMPLE 7

11β-(4-dimethylaminophenyl)-17α-(prop-1-ynyl)-isoxazolo[4,5-b]-Δ$^{4,9}$-estradiene-17β-ol 350 mg of hydroxylamine hydrochloride were added to a solution of 1.2 g of 2-hydroxymethylene-11β-(4-dimethylaminophenyl)-17α-(prop-1-ynyl)-Δ$^{4,9}$-estradiene-17β-ol-3-one in 6 ml of tert.-butanol and the mixture was refluxed for 10 minutes, cooled and diluted with water. The mixture was extracted with methylene chloride and the organic phase was washed, dried and evaporated to dryness under reduced pressure. The 1.23 g of residue was chromatographed over 90 g of silica gel and eluted with a 4-6 petroleum ether-ether mixture to obtain 755 mg of 11β-(4-dimethylaminophenyl)-17α-(prop-1-ynyl)-isoxazolo[4,5-b]-Δ$^{4,9}$-estradiene-17β-ol.

EXAMPLE 8

2-cyano-11β-(4-dimethylaminophenyl)-17α-(prop-1-ynyl)-Δ$^{4,9}$-estradiene-17β-ol-3-one Nitrogen was bubbled at room temperature through a solution of 1.2 g of the product of Step A of Example 7 in 10 ml of methanol for 15 minutes and 3 ml of N potassium hydroxide solution were added thereto. The solution stood under nitrogen at room temperature for three hours and was diluted with water. The mixture was extracted with methylene chloride and the organic phase was washed with water, dried and evaporated to dryness under reduced pressure. The 1.19 g of residue was chromatographed over silica gel and eluted with a 7-3 ether-petroleum ether mixture to obtain 685 mg of 2-cyano-11β-(4-dimethylaminophenyl)-17α-(prop-1-ynyl)-Δ$^{4,9}$-estradiene-17β-ol-3-one.

| Analysis: C$_{30}$H$_{34}$N$_2$·$\frac{1}{4}$ H$_2$O | | | | |
|---|---|---|---|---|
| | % C 78.48 | % H 7.57 | % N 6.10 | % H$_2$O =1 |
| Calculated: | | | | |
| Found: | 78.2 | 7.6 | 5.9 | =0.8 |

EXAMPLE 9

2,2-dicyano-11β-(4-dimethylaminophenyl)-17α-(prop-1-ynyl)-Δ$^{4,9}$-estradiene-17β-ol-3-one 4.4 ml of a solution of 1.6M of butyllithium in hexane were added under nitrogen to 10 ml of anhydrous tetrahydrofuran and after cooling the mixture to −70° C., a solution of 1.15 ml of N-cyclohexyl-isopropylamine in 15 ml of anhydrous tetrahydrofuran was added thereto. The solution was cooled to −70° C. and a solution of 1.290 g of 11β-(4-dimethylaminophenyl)-17α-(prop-1-ynyl)-Δ$^{4,9}$-estradiene-17β-ol-3-one in 12 ml of tetrahydrofuran was added thereto to obtain solution A.

Solution A was added dropwise at −60° C. to a solution of 2.55 g of tosyl cyanide in 15 ml of tetrahydrofuran and the mixture stood at −60° C. for 40 minutes and then allowed to rise to room temperature. The mixture was poured into water and was extracted with ethyl acetate. The organic phase was washed, dried and evaporated to dryness under reduced pressure and the 2.85 g of residue were chromatographed over 80 g of silica gel. Elution with a 4-1 benzene-ethyl acetate mixture yielded 1.06 g of product which was crystallized from a methylene chloride-isopropyl ether mixture to obtain 774 mg of 2,2-dicyano-11β-(4-dimethylaminophenyl)-17α-(prop-1-ynyl)-Δ$^{4,9}$-estradiene-17β-ol-3-one melting at 265° C.

| Analysis: $C_{31}H_{33}N_3O_2$ | | | |
|---|---|---|---|
| Calculated: | % C 77.63 | % H 6.93 | % N 8.76 |
| Found: | 77.6 | 7.0 | 8.7 |

EXAMPLE 10

11β-(4-dimethylaminophenyl)-17α-(prop-1-ynyl)-Δ$^{5(10)}$-estrene-17β-ol-3-one 15 ml of anhydrous tetrahydrofuran and 2.5 ml of tert.-butanol were added to liquid ammonia at −60° C. and then 2.15 g of 11β-(4-dimethylaminophenyl)-17α-(prop-1-ynyl)-Δ$^{4,9}$-estradiene-17β-ol-3-one were added thereto. 80 mg of lithium were added to the solution in 6 fractions over 30 minutes and after another 30 minutes at −60° C., the mixture was placed in an ice bath. 40 ml of an aqueous solution of 100 g/l of ammonium chloride were slowly added to the mixture which was stirred at room temperature for 30 minutes. The mixture was extracted with ethyl acetate and the organic phase was washed with aqueous ammonium chloride solution, dried and evaporated to dryness. The 2.3 g of residue were chromatographed over 90 g of silica gel and eluted with a 4-1 benzene-ethyl acetate mixture to obtain 1.67 g of 11β-(4-dimethylaminophenyl)-17α-(prop-1-ynyl)-Δ$^{5(10)}$-estrene-17β-ol-3-one. An analytical sample which was obtained by chromatography over silica gel and elution with a 2-1 ether-heptane mixture had a specific rotation $[α]_D^{20} = −68.5° ±2.0$ (c=1% in chloroform).

| Analysis: $C_{29}H_{37}NO_2$ | | | |
|---|---|---|---|
| Calculated: | % C 80.7 | % H 8.64 | % N 3.25 |
| Found: | 80.6 | 8.90 | 3.05 |

EXAMPLE 11

3-methoxy-11β-(4-dimethylaminophenyl)-17α-(prop-1-ynyl)-Δ$^{1,3,5(10)}$-estratriene-17β-ol 0.06 ml of methyl sulfate were added all at once to a solution of 215 mg of 11β-(4-dimethylaminophenyl)-17α-(prop-1-ynyl)-Δ$^{1,3,5(10)}$-estratriene-3,17β-diol, 6 ml of 0.1N sodium hydroxide solution and 6 ml of acetone cooled in an ice bath and the mixture was removed from the ice bath, stirred for 2½ hours and then was diluted with 30 ml of ethyl acetate. The decanted organic phase was washed with aqueous sodium chloride solution, dried and evaporated to dryness under reduced pressure. The 155 mg of residue were chromatographed over silica gel and eluted with a 3-2 petroleum ether-ethyl acetate mixture after dissolution in methylene chloride to obtain 120 mg of 3-methoxy-11β-(4-dimethylaminophenyl)-17α-(prop-1-ynyl)-Δ$^{1,3,5(10)}$-estratriene-17β-ol with an Rf=0.4.

EXAMPLE 12

3-methoxy-11β-(4-dimethylaminophenyl)-17α-(prop-1-ynyl)-17β-acetoxy-Δ$^{1,3,5(10)}$-estratriene 0.08 ml of methyl sulfate were added with stirring under nitrogen to a mixture of 330 mg of 11β-(4-dimethylaminophenyl)-17α-(prop-1-ynyl)-17β-acetoxy-Δ$^{1,3,5(10)}$-estratriene-3-ol, 1.65 ml of acetone, 0.33 ml of water and 0.42 ml of 2N sodium hydroxide solution and the mixture was stirred for one hour and was diluted with water. The mixture was extracted with ethyl acetate and the organic phase was dried and evaporated to dryness under reduced pressure. The residue was chromatographed over silica gel and eluted with a 4-1 cyclohexane-ethyl acetate mixture to obtain 220 mg of 3-methoxy-11β-(4-dimethylaminophenyl)-17α-(prop-1-ynyl)-17β-acetoxy-Δ$^{1,3,5(10)}$-estratriene.

EXAMPLE 13

11β-[4-(2-dimethylaminoethoxy)-phenyl]-Δ$^{1,3,5(10)}$-estratriene-3,17β-diol STEP A: 3,3-ethylenedioxy-11β-[4-(2-dimethylaminoethoxy)phenyl]-Δ$^9$-estrene-5α-ol-17-one A solution of 97.4 g of 4-bromo-4-(2-dimethylaminoethoxy)-benzene in 480 ml of tetrahydrofuran was added at about 35° C. over 75 minutes to a mixture of 11.5 g of magnesium turnings and 20 ml of tetrahydrofuran and the mixture was stirred for one hour and 380 ml of the solution were poured into a suspension of 23.5 g of a complex of $CuBr.(CH_3)_2S$ and 235 ml of tetrahydrofuran. After stirring for 15 minutes at room temperature, a solution of 30 g of 3,3-ethylenedioxy-5α,10α-epoxy-Δ$^{9(11)}$-estrene-17-one [described in EPC application No. 57.115] in 150 ml of tetrahydrofuran was added to the mixture over 20 minutes and the mixture was stirred at room temperature for 16 hours and was poured into 3 liters of aqueous saturated ammonium chloride solution. The mixture was extracted with ether and the organic phase was washed with aqueous saturated ammonium chloride solution then with aqueous saturated sodium chloride solution, dried and evaporated to dryness under reduced pressure. The 66.7 g of residue were chromatographed over silica gel and eluted with a 9-1 chloroform-methanol mixture containing 1% of triethylamine and then over alumina and eluted with an 8-2 benzene-ethyl acetate mixture to obtain 30.65 g of 3,3- ethylenedioxy-11β-[4-(2-dimethylaminoethoxy)-phenyl]-Δ$^9$-estrene-5α-ol-17-one.

STEP B: 11β-[4-(2-dimethylaminoethoxy)-phenyl]-Δ$^{4,9}$-estradiene-3,17-dione

A mixture of 5 g of the product of Step A, 100 ml of methanol and 15 ml of 2N hydrochloric acid was stirred at room temperature for 3 hours and was then poured into 400 ml of ether. The mixture was made alkaline by the addition of 100 ml of 0.5M sodium bicarbonate solution and was stirred for 15 minutes. The decanted aqueous phase was extracted with ether and the organic phase was washed with aqueous saturated sodium chloride solution, dried and evaporated to dryness under reduced pressure. The 3.90 g of product were empasted with a minimum of isopropyl ether 3 times to obtain 3.10 g of 11β-[4-(2-dimethylaminoethoxy)-phenyl]-Δ$^{4,9}$-estradiene-3,17-dione melting at 206° C.

STEP C: 11β-[4-(2-dimethylaminoethoxy)-phenyl]-Δ$^{1,3,5(10)}$-estratriene-3-ol-17-one A mixture of 4 g of acetic anhydride and 2 ml of acetyl bromide was added at 0° to 5° C. to a solution of 4 g of the product of Step B in 40 ml of methylene chloride and the mixture was allowed to rise to room temperature and was then stirred for 2 hours. The mixture was poured into 200 ml of aqueous saturated sodium bicarbonate solution and was stirred for 15 minutes. The mixture was extracted with methylene chloride and the organic phase was washed with water, dried and evaporated to dryness under reduced pressure. The 4.33 g of residue were dissolved in 40 ml of methanol and after the addition of 4 ml of sodium hydroxide, the mixture was stirred for 90 minutes at room temperature and was poured into 200 ml of water. The mixture was adjusted to a pH of ≃2 by addition of 30 ml of 2N hydrochloric acid and was then adjusted to a pH of ≃9 by addition of 5 ml of ammonium hydroxide. The mixture was extracted with methylene chloride and the organic phase was washed with water, dried and evaporated to dryness under reduced pressure. The residue was chromatographed over silica gel and was eluted with a 9-1 methylene chloride-methanol mixture to obtain 2.6 g of 11β-[4-(2-dimethylaminoethoxy)-phenyl]-Δ$^{1,3,5(10)}$-estratriene-3-ol-17-one.

STEP D: 11β-[4-(2-dimethylaminoethoxy)-phenyl]-Δ$^{1,3,5(10)}$-estratriene-3,17β-diol 545 mg of sodium borohydride were added in small fractions to a mixture of 2.1 g of the product of Step C and 21 ml of methanol and the mixture was stirred at room temperature for one hour and was poured into 210 ml of a mixture of ice and water. The mixture was extracted with methylene chloride and the organic phase was washed with aqueous saturated sodium chloride solution, dried and evaporated to dryness under reduced pressure. The residue was chromatographed over silica gel and eluted with an 8-2 acetone-methanol mixture to obtain 1.37 g of product which was crystallized from a methylene chloride-isopropyl ether to obtain 1.27 g of 11β-[4-(2-dimethylaminoethoxy)-phenyl]-Δ$^{1,3,5(10)}$-estratriene-3,17-diol melting at 130° C. and having a specific rotation of $[\alpha]_D^{20} = -46.5° \pm 1.5°$ (c=0.8% in chloroform).

EXAMPLE 14

11β-[4-2-dimethylaminoethoxy)-phenyl]-Δ$^{1,3,5(10)}$-estratriene-17β-ol

STEP A: A AND B isomers of 11β-[4-(2-dimethylaminoethoxy)-phenyl]-Δ$^{4,9}$-estradiene-3,17β-diol 1.74 g of sodium borohydride were added in small fractions over 20 minutes to a solution of 5 g of 11β-[4-(2-dimethylamino ethoxy)-phenyl]-Δ$^{4,9}$-estradiene-3,17-dione in 100 ml of methanol and the mixture was stirred at room temperature for one hour and was poured into 750 ml of ice and water. The mixture was stirred for 30 minutes and was vacuum filtered. The product was washed until the wash water was neutral and dried to obtain 4.6 g of A and B isomers of 11β-[4-(2-dimethylaminoethoxy)-phenyl]-Δ$^{4,9}$-estradiene-3,17β-diol melting at 110° C.

STEP B: 11β-[4-(2-dimethylaminoethoxy)-phenyl]-Δ$^{1,3,5(10)}$-estratriene-17β-ol A mixture of 1 g of the product of Step A, 20 ml of tetrahydrofuran and 1 ml of 6N hydrochloric acid was stirred at room temperature for 3 hours and was poured into 200 ml of aqueous saturated sodium bicarbonate solution. The mixture was extracted with ethyl acetate and the organic phase was washed with aqueous saturated sodium chloride solution, dried and evaporated to dryness under reduced pressure. The residue was chromatographed over silica gel and eluted with an 8-2 petroleum ether-acetone mixture to obtain 325 mg of product which was dissolved in a 1-1 methylene chloride-isopropyl ether mixture. The solution was slowly concentrated to half its volume to obtain 300.5 mg of 11β-[4-(2-dimethylaminoethoxy)-phenyl]-Δ$^{1,3,5(10)}$-estratriene-17β-ol melting at 155° C. and having a specific rotation of $[\alpha]_D^{20} = -38.5° \pm 2°$ (c=0.8% in chloroform).

EXAMPLE 15

3-(2-dimethylamino-ethoxy)-11β-phenyl-Δ$^{1,3,5(10)}$-estratriene-17β-ol

STEP A: 3,3-ethylenedioxy-11β-phenyl-Δ$^9$-estrene-5α-ol-17-one 80 g of bromobenzene were added over 70 minutes to a refluxing mixture of 13 g of magnesium turnings and 30 ml of tetrahydrofuran and the mixture was allowed to return to 20° C. with stirring. The mixture was cooled to -25° C. to obtain 330 ml of a solution of 0.85M of phenyl magnesium bromide. 4.165 g of cuprous chloride were added thereto all at once and the mixture was stirred at -25° C. for 10 minutes after which a solution of 11.5 g of 3,3-ethylenedioxy-5α,10α-epoxy-Δ$^{9(11)}$-estrene-17-one in 60 ml of tetrahydrofuran was added dropwise at -25° C. over 20 minutes. The mixture was held at -25° C. for two hours and was then poured into a mixture of 600 ml of ice and 45 g of ammonium chloride. The mixture was stirred for 30 minutes and was extracted with ether. The organic phase was washed with water, dried and evaporated to dryness under reduced pressure. The residue was chromatographed over silica gel and eluted with a 6-4 benzene-ethyl acetate mixture contain 1% of triethylamine to obtain 7.86 g of 3,3-ethylenedixoy-11β-phenyl-Δ$^9$-estrene-5α-ol-17-one melting at 173° C. and having a specific rotation of $[\alpha]_D^{20} = +54.5° \pm 1.5°$ (c=1% in chloroform.

STEP B: 11β-phenyl-Δ$^{4,9}$-estradiene-3,17-dione

A mixture of 7.4 g of the product of Step A in 225 ml of 95% ethanol was heated to 40° C. and 7.4 g of redex CF resin were added thereto all at once. The mixture was refluxed with stirring under an inert gas for one hour and was filtered. The product was empasted four times with 20 ml of 95% ethanol and the filtrate was evaporated to dryness under reduced pressure. The 6.5 g of resin were chromatographed over silica gel and eluted with a 9-1 chloroform-ethyl acetate mixture. The 486 mg of product were dissolved at reflux in a mixture of 12.5 ml of isopropyl ether and 3 ml of methylene chloride and the mixture was filtered hot. The filtrate was concentrated to a small volume and crystallization was refluxed was effected. The mixture was vacuum filtered and the product was washed with isopropyl ether to obtain 369.4 mg of 11β-phenyl-Δ$^{4,9}$-estradiene-3,17-one melting at a 197° C. and having a specific rotation of [α]$_D^{20}$= +223°±3° (c=0.5% in chloroform).

STEP C: 11β-phenyl-Δ$^{1,3,5(10)}$-estratriene-3-ol-17-one

A mixture of 3.75 ml of acetic anhydride and 1.9 ml of acetyl bromide was added dropwise with stirring at 0° C. to a solution of 3.76 g of the product of Step B in 26.3 ml of methylene chloride and the mixture was stirred at room temperature for 75 minutes and was added dropwise with stirring to 90 ml of aqueous saturated sodium bicarbonate solution. After stirring for 15 minutes, the mixture was extracted with methylene chloride and the organic phase was washed with water, dried and evaporated to dryness under reduced pressure. The residue was added to 26.3 ml of methanol and then 18.8 ml of sodium hydroxide solution were added thereto. The mixture was stirred for 16 hours and was acidified to a pH of about 1 at approximately 20° C. by addition of 40 ml of sulfuric acid diluted to one-fifth. The mixture was stirred for 20 minutes and was then vacuum filtered. The product was empasted four times with 25 ml of water to obtain 4.030 g of product which was crystallized from methylene chloride to obtain 3.01 g of 11β-phenyl-Δ$^{1,3,5(10)}$-estratriene-3-ol-17-one melting at 290° C. and having a specific rotation of [α]$_D^{20}$= −9°±2° (c=0.5% in chloroform).

STEP D: 11β-phenyl-Δ$^{1,3,5(10)}$-estratriene-3,17β-diol 144 mg of sodium borohydride were added over 10 minutes under an inert atmosphere with stirring to a mixture of 1 g of the product of Step C in 10 ml of methanol at 50° C. and after stirring at 50° C. for one hour, the mixture was cooled to 20° C. The pH was adjusted to 5 by dropwise addition of 0.4 ml of acetic acid and the mixture was stirred for 10 minutes and poured into 30 ml of ice and water. The mixture was stirred for 30 minutes and was vacuum filtered. The product was empasted with water and dried to obtain 896 mg of 11β-phenyl-Δ$^{1,3,5(10)}$-estratriene-3,17β-diol melting at 228° C. and having a specific rotation of [α]$_D^{20}$= −34°±2° (c=0.5% in chloroform).

STEP E: 3-(2-dimethylaminoethoxy)-11β-phenyl-Δ$^{1,3,5(10)}$-estratriene-17β-ol 3.5 ml of an 95% ethanolic solution of N sodium hydroxide were added all at once to a mixture of 1.220 g of the product of Step D and 12.2 ml of 95% ethanol and the mixture was heated to 60° C. after which a solution of the amine prepared from 555 mg of dimethylamino-2-chlorethane hydrochloride in 1.7 ml of 95% ethanol was added all at once. The mixture was neutralized by the addition of freshly prepared 3.85 ml of N sodium hydroxide in 95% ethanol and the mixture was refluxed with stirring under an inert atmosphere for 90 minutes and was cooled to 20° C. and filtered. The product was empasted with 10 ml of 95% ethanol and the filtrate was evaporated to dryness. The residue and 20 ml of methylene chloride and 20 ml of water was stirred for 10 minutes and the decanted aqueous phase was extracted with methylene chloride. The organic phase was washed with water, dried and evaporated to dryness under reduced pressure. The 1.261 g of residue was chromatographed over silica gel and eluted with a 6-4 chloroform-methanol mixture to obtain 939 mg of 3-(2-dimethylaminoethoxy)-11β-phenyl-Δ$^{1,3,5(10)}$-estratriene-17β-ol with a specific rotation of [α]$_D^{20}$= −32°±2° (c=0.7% in chloroform).

EXAMPLE 16

11β-(4-pyridyl)-17α-(prop-1-ynyl-Δ$^{4,9}$-estradiene-17β-ol-3-one

STEP A: 3,3-[1,2-ethanediyl-bisoxy]-17α-(prop-1-ynyl)-Δ$^{5(10),9(11)}$-estradiene-17β-ol 207 ml of a solution of 1.15% ethyl magnesium bromide in tetrahydrofuran were stirred at 0° C. while bubbling gaseous propyne dried over calcium chloride therethrough for 90 minutes and the temperature was then allowed to return to room temperature. The mixture was stirred for one hour while the bubbling was continued. Then a solution of 30 g of 3,3-[1,2-ethanediyl-bisoxy]-Δ$^{5(10),9(11)}$-estradiene-17-one in 120 ml of anhydrous tetrahydrofuran and one drop of triethylamine was added to the mixture over 30 minutes and the mixture was stirred for 2 hours at room temperature and was then poured into a mixture of ice, distilled water and ammonium chloride. The stirred mixture was extracted 3 times with ether and the organic phase was washed with water, dried and evaporated to dryness under reduced pressure. The residue was dried under reduced pressure to obtain 35.25 g of 3,3-[1,2-ethanediyl-bisoxy]-17α-(prop-1-ynyl)-Δ$^{5(10),9(11)}$-estradiene-17β-ol.

NMR Spectrum (deuterochloroform):

Peaks at 0.83 ppm (hydrogens of 18-methyl); at 1.85 ppm (hydrogens of methyl of C≡C—CH$_3$); at 5.65 ppm (hydrogens of 11-carbon); at 4 ppm (hydrogens of ethylene ketal).

STEP B: 3,3-[1,2-ethanediyl-bisoxy]-5α,10α-epoxy-17α-(prop-1-ynyl)-Δ$^{9(11)}$-estrene-17β-ol A mixture of 30 g of the product of Step A in 150 ml of methylene chloride was stirred while bubbling nitrogen therethrough and after cooling the mixture to 0° C., 1.8 ml of hexafluoroacetone sesquihydrate were added all at once. The mixture was stirred while 4.35 ml of 85% oxygenated water were added and the mixture was stirred at 0° C. for 72 hours while continuing to bubble nitrogen therethrough. The solution was poured into a mixture of 250 g of ice and 500 ml of 0.2N sodium thiosulfate solution and the mixture was stirred for a few moments and was then extracted with methylene chloride. The organic phase was washed with distilled water, dried over sodium sulfate in the presence of pyridine and evaporated to dryness under reduced pressure. The residue was dried under reduced pressure and the 31.6 g of residue were chromatographed over silica gel. Elution with a 9-1 benzene-ethyl acetate mixture yield 3,3-[1,2-ethanediyl-bisoxy]-5α10α-epoxy-17α-(prop-1-ynyl)-Δ$^{9(11)}$-estrene-17β-ol.

NMR Spectrum (deuterochloroform):

Peaks at 0.82 ppm (hydrogens of 18-CH$_3$); at 1.83 ppm (hydrogens of methyl of C≡C—CH$_3$); at 6.1 ppm (hydrogens of 11-carbon); at 3.92 ppm (hydrogens of ethylene ketal).

STEP C: 3,3-[1,2-ethanediyl-bisoxy]-11β-(4-pyridyl)-17α-(prop-1-ynyl)-Δ$^9$-estrene-5α,17β-diol 100 ml of a tetrahydrofuran solution of 0.5 to 0.6M 4-chloropyridyl magnesium bromide prepared from 15 g of 4-chloro-pyridine and 6 g of magnesium was added at 20° C. to a solution of 6.16 g of dimethyl sulfide-cuprous bromide complex in 40 ml of tetrahydrofuran and the mixture was stirred under an inert atmosphere at room temperature for 20 minutes. Then, a solution containing 3.7 g of 3,3-[1,2-ethanediyl-bisoxy]-5α,10α-epoxy-17α-(prop-1-ynyl)-$\Delta^{9(11)}$-estrene-17β-ol was added thereto over 10 minutes and the mixture was stirred at room temperature for one hour and was then poured into a mixture of cold water and ammonium chloride. The mixture was stirred at room temperature for 30 minutes and was extracted with ether. The organic phase was washed with an aqueous saturated sodium chloride solution, was dried and evaporated to dryness under reduced pressure. The 6 g of residue were chromatographed over silica gel and eluted with a 1-1 methylene chloride-acetone mixture containing 1 ppm of triethylamine to obtain 3.15 g of 3,3-[1,2-ethanediyl-bisoxy]-11β-(4-pyridyl)-17α-(prop-1-ynyl)-$\Delta^9$-estrene-5α,17β-diol which was dried towards 60° C. at 0.1 mm Hg which had a specific rotation of $[\alpha]_D^{20} = -52° \pm 1.5°$ (c=1% in chloroform).

STEP D: 11β-(4-pyridyl)-17α-(prop-1-ynyl)-$\Delta^{4,9}$-estradiene-17β-ol-3-one A solution of 2.9 g of the product of Step C, 14 ml of methanol and 7 ml of 2N hydrochloric acid was stirred under an inert atmosphere at room temperature for 3 hours and was then admixed with a solution of 200 ml of ether and 90 ml of aqueous saturated sodium bicarbonate solution. The mixture was stirred at room temperature for 15 minutes and the decanted aqueous phase was extracted with ether. The organic phase was washed with aqueous saturated sodium chloride solution, dried and evaporated to dryness under reduced pressure. The 2.3 g of residue were chromatographed over silica gel and eluted with a 6-4 methylene chloride-acetone mixture. The 1.7 g of product was dried for 24 hours at 0.1 mm Hg and for 8 hours at 80° C. to obtain 11β-(4-pyridyl)-17α-(prop-1-ynyl)-$\Delta^{4,9}$-estradiene-17β-ol-3-one with a specific rotation of $[\alpha]_D^{20} = +30.5° \pm 1°$ (c=1% in chloroform).

Using the same procedure, 11β-(3-pyridyl)-17α-(prop-1-ynyl)-$\Delta^{4,9}$-estradiene-17β-ol-3-one with a specific rotation of $[\alpha]_D^{20} = +14°$ (c=1% in chloroform) and 11β-(2-pyridyl)-17α-(prop-1-yny)-$\Delta^{4,9}$-estradiene-17β-ol-3-one with a specific rotation of $[\alpha]_D^{20} = -2°$ (c=1% in chloroform) were prepared.

EXAMPLE 17

11β-[3-(N,N-dimethylamino)-propyl]-17α-(prop-1-ynyl)-$\Delta^{4,9}$-estradiene-17β-ol-3-one STEP A: 3,3-[1,2-ethanediyl-bisoxy]-11β-[3-(N,N-dimethylamino)-propyl]-17α-(prop-1-ynyl)-$\Delta^9$-estrene-5α,17β-diol 12.33 g of dimethyl sulfide-cuprous bromide complex were added over 5 minutes at 0° C. to a solution of 0.85M of 3-(N,N-dimethylamino)-propyl magnesium chloride [prepared from 42 g of chloro 3-(N,N-dimethylamino)-propane and 10.5 g of magnesium] and the mixture was stirred at 0° C. for 25 minutes. A solution of 3.70 g of 3,3-[1,2-ethanediyl-bisoxy]-5α,10α-epoxy-17α-(prop-1-ynyl)-$\Delta^{9(11)}$-estrene-17β-ol in 50 ml of tetrahydrofuran was added to the mixture dropwise and the mixture was then stirred at 0° C. for 3 hours and was poured into a mixture of 40 g of ammonium chloride and 200 ml of iced water. The mixture was stirred at room temperature for 15 minutes and was then extracted with ether. The organic phase was washed with aqueous saturated sodium chloride solution, dried and evaporated to dryness under reduced pressure. The 4.6 g of residue were chromatographed over silica gel and eluted with an 8-2 methylene-chloride-methanol mixture to obtain 2.55 g of 3,3-[1,2-ethanediyl-bisoxy]-11β-[3-(N,N-dimethylamino)-propyl]-17α-(prop-1-ynyl)-$\Delta^9$-estrene-5α,17β-diol with a specific rotation of $[\alpha]_D^{20} = -86° \pm 1.5°$ (c=1% in chloroform).

STEP B: 11β-[3-(N,N-dimethylamino)-propyl]-17α-(prop-1-ynyl)-$\Delta^{4,9}$-estradiene-17β-ol-3-one A mixture of 2.4 g of the product of Step A, 14 ml of methanol and 7 ml of 2N hydrochloric acid was stirred under an inert atmosphere at room temperature for 4 hours and then 200 ml of isopropyl ether and 90 ml of aqueous saturated sodium bicarbonate solution were added thereto. The mixture was stirred at room temperature for 30 minutes and the decanted aqueous phase was extracted with ether. The organic extract was washed with aqueous saturated sodium chloride solution, was dried and evaporated to dryness under reduced pressure. The 1.8 g of residue were chromatographed over silica gel and eluted with an 8-2 chloroform-methanol mixture. The 1.30 g of product were dried at 30° to 40° C. at 0.1 mm Hg to obtain 1.25 g of 11β-[3-(N,N-dimethylamino)-propyl]-17α-(prop-1-ynyl)-$\Delta^{4,9}$-estradiene-17β-ol-3-one with a specific rotation of $[\alpha]_D^{20} = -114° \pm 2.5°$ (c=1% in chloroform).

EXAMPLE 18

11β-[4-(N,N-dimethylaminoethoxy)-phenyl]-17α-(prop-1-ynyl)-$\Delta^{4,9}$-estradiene-17β-ol-3-one STEP A: 3,3-[1,2-ethanediyl-bisoxy]-11β-[4-(N,N-dimethylaminoethoxy)-phenyl]-17α-(prop-1-ynyl)-$\Delta^9$-estrene-5α,17β-diol A solution of 24 g of 4-(N,N-dimethylaminoethoxy)-bromobenzene was added dropwise over 45 minutes to 90 ml of anhydrous tetrahydrofuran and 2 ml of 1,1-dibromoethane were added as catalyst. After the addition, the mixture was stirred at 25° C. for one hour to obtain a solution of 0.7M of 4-(N,N-dimethylaminoethoxy)-bromobenzene magnesium which was then added to a solution of 6.16 g of dimethylsulfide-cuprous bromide complex in 20 ml of tetrahydrofuran. The mixture was stirred at room temperature for 20 minutes and a solution of 3.7 g of 3,3-[1,2-(ethanediyl-bisoxy)]-5α,10α-epoxy-17α-prop-1-ynyl-$\Delta^{9(11)}$-estrene-17β-ol in 50 ml of tetrahydrofuran was added thereto dropwise over a few minutes. The mixture was stirred under an inert atmosphere for one hour and was then poured into a solution of 15 g of ammonium chloride in 20 ml of iced water. The mixture was extracted with ether and the organic phase was washed with aqueous saturated sodium chloride solution, was dried and evaporated to dryness under reduced pressure. The 18.3 g of oil were chromatographed over silica gel and eluted with chloroform to obtain 4.5 g of 3,3-[1,2-ethanediyl-bisoxy]-11β-[4-(N,N-dimethylaminoethoxy)-phenyl]-17α-(prop-1-ynyl)-$\Delta^9$-estrene-5α,17β-diol with a specific rotation of $[\alpha]_D^{20} = -44° \pm 1.5°$ (c=1% in chloroform).

STEP B: 11β-[4-(N,N-dimethylaminoethoxy)-phenyl]-17α-(prop-1-ynyl)-$\Delta^{4,9}$-estradiene-17β-ol-3-one 9.5 ml of 2N hydrochloric acid were added to a solution of 4.5 g of the product of Step A in 20 ml of methanol and the solution was stirred at room temperature for 2 hours. 260 ml of ether and 110 ml of an aqueous saturated sodium bicarbonate solution were added to the mixture which was stirred at room temperature for 15 minutes. The decanted aqueous phase was extracted with ether and the organic phase was dried and evaporated to dryness under reduced pressure. The 3.3 g of residue were chromatographed over silica gel and eluted with a 92.5-7.5 methylene chloride-methanol mixture to obtain 1.8 g of amorphous 11β-[4-(N,N-dimethylaminoethoxy)-phenyl]-17α-(prop-1-ynyl)-Δ$^{4,9}$-estradiene-17β-ol-3-one with a specific rotation of [α]$_D^{20}$= +71° (c=1% in chloroform).

EXAMPLE 19

11β-[4-(N,N-dimethylamino)-phenyl]-17α-(prop-1-ynyl)-Δ$^{4,9}$-estradiene-17β-ol-3-one STEP A: 3,3-[1,2-ethanediyl-bisoxy]-11β-[4-(N,N-dimethylamino)-phenyl]-17α-(prop-1-ynyl)-Δ$^9$-estrene-5α,17β-diol A solution of 38 mmoles of p-dimethylaminophenyl magnesium bromide in tetrahydrofuran was added to a suspension of 4.1 g of a cuprous bromide-dimethylsulfide complex in 20 ml of tetrahydrofuran and then a solution of 2.45 g of 3,3-[1,2-ethanediyl-bisoxy]-5α,10α-epoxy-17α-(prop-1-ynyl)-Δ$^{9(11)}$-estrene-17β-ol in tetrahydrofuran was added thereto. The mixture was stirred for 10 minutes and was then hydrolyzed with 50 ml of aqueous saturated ammonium chloride solution. The decanted aqueous phase was extracted with ether and the organic phase was washed with water, dried and evaporated to dryness under reduced pressure. The 11 g of residue were chromatographed over silica gel and eluted with a 6-4 cyclohexane-ethyl acetate mixture to obtain 1.8 g of 3,3-[1,2-ethanediyl-bisoxy]-11β-[4-(N,N-dimethylamino)-phenyl]-17α-(prop-1-ynyl)-Δ$^9$-estrene-5α,17β-diol which after crystallization from isopropyl ether and ethyl acetate had a specific rotation of [α]$_D^{20}$= −66.5° (c=1% in chloroform) and a melting point of 210° C. and 750 mg of the corresponding 11α-compound.

STEP B: 11β-[4-(N,N-dimethylamino)-phenyl]-17α-(prop-1-ynyl)-Δ$^{4,9}$-estradiene-17β-ol-3-one 2 ml of concentrated hydrochloric acid were added to a solution of 1.53 g of the product of Step A in 60 ml of methanol and after stirring the mixture for 30 minutes at room temperature, 150 ml of ether and then 50 ml of aqueous N sodium hydroxide solution were added thereto. The reaction mixture was stirred for 15 minutes and the decanted organic phase was dried and evaporated to dryness under reduced pressure. The 1.4 g of residue were chromatographed over silica gel and was eluted with a 7-3 cyclohexane-ethyl acetate mixture to obtain 0.932 g of 11β-[4-(N,N-dimethylamino)-phenyl]-17α-(prop-1-ynyl)-Δ$^{4,9}$-estradiene-17β-ol-3-one melting at 150° C. and a specific rotation of [α]$_D^{20}$= +138.5° (c=0.5% in chloroform).

EXAMPLE 20

11β-[4-trimethylsilyl-phenyl]-17α-(prop-1-ynyl)-Δ$^{4,9}$-estradiene-17β-ol-3-one STEP A: 3,3-[1,2-ethanediyl-bisoxy]-11β-(4-trimethylsilyl-phenyl)-17α-(prop-1-ynyl)-Δ$^9$-estrene-5α,17β-diol 200 mg of cuprous chloride were added under an inert atmosphere at −30° C. to 45 ml of solution of 0.65M of 4-trimethylsilyl-phenyl magnesium bromide in tetrahydrofuran and a solution of 3.3 g of 3,3-[1,2-ethanediyl-bisoxy]-5α,10α-epoxy-17α-(prop-1-ynyl)-Δ$^{9(11)}$-estrene-17β-ol in 25 ml of tetrahydrofuran were added thereto dropwise at −20° C. After one hour, the mixture was hydrolyzed with aqueous ammonium chloride solution and was extracted with ether. The organic phase was dried and evaporated to dryness under reduced pressure and the residue was chromatographed over silica gel. Elution with a 94-6 methylene chloride-acetone mixture containing 0.1% of triethylamine yielded 2.087 g of 3,3-[1,2-ethanediyl-bisoxy]-11β-(4-trimethylsilyl-phenyl)-17α-(prop-1-ynyl)-Δ$^9$-estrene-5α,17β-diol which after crystallization from isopropyl ether and then ethyl acetate melted at 226° C. and a specific rotation of [α]$_D^{20}$= −60°±1.5° (c=0.9% in chloroform).

STEP B: 11β-(4-trimethylsilyl-phenyl)-17α-(prop-1-ynyl)-Δ$^{4,9}$-estradiene-17β-ol-3-one 1.7 g of Redex sulfonic acid resin were added to a solution of 1.68 g of the product of Step A in 17 ml of 90% alcohol and the mixture was refluxed for 30 minutes and vacuum filtered. The filter was rinsed with methylene chloride and the filtrate was evaporated to dryness under reduced pressure. The residue was taken up in methylene chloride and the solution was dried and evaporated to dryness under reduced pressure. The residue was chromatographed over silica gel and was eluted with an 85-15 benzene-ethyl acetate mixture to obtain 1.217 g of 11β-(4-trimethylsilyl-phenyl)-17α-(prop-1-ynyl)-Δ$^{4,9}$-estradiene-17β-ol-3-one melting at 212° C. and having a specific rotation of [α]$_D^{20}$= −94° (c=0.9% in chloroform).

The same procedure was used to prepare 11β-[3-trimethylsilyl-phenyl]-17α-(prop-1-ynyl)-Δ$^{4,9}$-estradiene-17β-ol-3-one with a specific rotation of [α]$_D^{20}$= −52.5°±2° (c=1% in chloroform).

EXAMPLE 21

11β-[4-(N,N-dimethylamino)-phenyl]-17β-ethynyl-Δ$^{4,9}$-estradiene-17α-ol-3-one STEP A: 3,3-dimethoxy-17β-ethynyl-Δ$^{5(10),9(11)}$-estradiene-17α-ol A mixture of 16.8 g of 3,3-dimethoxy-17α-ethynyl-Δ$^{5(10),9(11)}$-estradiene-17β-ol, 175 ml of anhydrous tetrahydrofuran and 4.35 g of lithium bromide was stirred at room temperature for 5 minutes and then the mixture was cooled to −60° C. and 3.9 ml of methane sulfonyl chloride were added thereto. The mixture was stirred at −60° C. for one hour and was then poured into 500 ml of aqueous saturated ammonium chloride solution. The mixture was stirred for 10 minutes and was extracted with methylene chloride. The organic phase was dried and after the addition of 2.5 ml of pyridine, the mixture was evaporated to dryness at 0° C. under reduced pressure. 75 mg of tetrahydrofuran were added to the residue and 12.5 ml of 0.75 g of silver nitrate in water were added thereto. The mixture was held at −30° C. for 18 hours and at room temperature for 4 hours and was then poured into 500 ml of aqueous semisaturated ammonium chloride solution containing 5 g of sodium cyanide. The mixture was stirred at 20° C. for 30 minutes and was extracted with chloroform. The organic phase was washed with aqueous saturated sodium chloride solution, dried and evaporated to dryness under reduced pressure. The residue was chromatographed over silica gel and was eluted with a 9-1 petroleum ether-ethyl acetate mixture to obtain 3 g of 3,3-dimethoxy-17β-ethynyl-Δ$^{5(10),9(11)}$-estradiene-17α-ol melting at −150° C. and having a specific rotation of [α]$_D^{20}$= +125°±2.5° (c=1% in chloroform).

STEP B: 3,3-dimethoxy-5α,10α-epoxy-17β-ethynyl-Δ$^{9(11)}$-estrene-17α-ol 0.12 ml of hexachloroacetone and 0.65 ml of oxygenated water (200 volumes) were added at 0° C. to a mixture of 2.6 g of the product of Step A, 12 ml of methylene chloride and one drop of pyridine and the mixture was stirred for one hour after which 13 ml of chloroform were added. The mixture was stirred for 18 hours and was then poured into 100 ml of aqueous saturated sodium thiosulfate solution. The mixture was stirred for 10 minutes and was extracted with chloroform. The organic phase was washed with aqueous saturated sodium chloride solution, dried and evaporated to dryness under reduced pressure to obtain 2.8 g of 3,3-dimethoxy-5α,10α-epoxy-17β-ethynyl-Δ$^{9(11)}$-estrene-17α-ol which was used as is for the next step. The product contained a small amount of the 5β,10β-epoxy compound.

STEP C: 3,3-dimethoxy-11β-[4-(N,N-dimethylamino)-phenyl]-17β-ethynyl-Δ$^9$-estrene-5α,17α-diol A mixture of 2.8 g of the product of Step B, 56 ml of anhydrous tetrahydrofuran and 80 mg of anhydrous copper chloride was stirred under an inert atmosphere at room temperature for 5 minutes and was then placed in an ice bath. 33 ml of 0.95M 4-dimethylaminophenyl magnesium bromide in tetrahydrofuran were added dropwise to the mixture which was then allowed to return to room temperature.

63 ml of 4-dimethylaminophenyl magnesium bromide were added to a suspension of 6.15 g of dimethylsulfide-copper bromide complex in 30 ml of anhydrous tetrahydrofuran while keeping the temperature below 28.5° C. and the mixture was stirred for 30 minutes. Then, the above solution was added dropwise thereto and the mixture was stirred at room temperature for 18 hours and was then poured into aqueous saturated ammonium chloride solution. The mixture was stirred for 10 minutes and was extracted with chloroform. The organic phase was washed with water, dried and evaporated to dryness under reduced pressure. The residue was chromatographed over silica gel and was eluted with a 1-1 petroleum ether-ethyl acetate mixture containing 0.5 ppm of triethylamine. The 1.28 g of product was chromatographed over silica gel and was eluted with the same mixture to obtain 0.84 g of 3,3-dimethoxy-11β-[4-(N,N-dimethylamino)-phenyl]-17β-ethynyl-Δ$^9$-estrene-5α,17α-diol.

STEP D: 11β-[4-(N,N-dimethylamino)-phenyl]-17β-ethynyl-Δ$^{4,9}$-estradiene-17α-ol-3-one A mixture of 0.76 g of the product of Step C, 15 ml of methanol and 1.6 ml of 2N hydrochloric acid was stirred for 90 minutes and was then poured into an aqueous saturated sodium bicarbonate solution. The mixture was extracted with chloroform and the organic phase was dried and evaporated to dryness under reduced pressure. The 0.76 g of residue was chromatographed over silica gel and was eluted with a 1-1 petroleum ether-ethyl acetate mixture and then with a 3-1 ether-petroleum ether mixture to obtain 0.435 g of 11β-[4-(N,N-dimethylamino)-phenyl]-17β-ethynyl-Δ$^{4,9}$-estradiene-17α-ol-3-one which after crystallization from isopropyl ether melted at 142° C. and had a specific rotation of $[\alpha]_D^{20} = +235.5° \pm 4.5°$ (c=0.45% in chloroform).

EXAMPLE 22

11β-[4-(N,N-dimethylamino)-phenyl]-17α-phenyl-Δ$^{4,9}$-estradiene-17β-ol-3-one

STEP A: 3,3-[1,2-ethanediyl-bisoxy]-5α,10α-epoxy-Δ$^{9(11)}$-estrene-17-one 2 drops of pyridine were added to a mixture of 11.18 g of 3,3-[1,2-ethanediyl-bisoxy]-Δ$^{5(10),9(11)}$-estradiene-17-one and 56 ml of methylene chloride and 4.3 ml of hexafluoroacetone sesquihydrate were added to the mixture at 0° C. 1.6 ml of 85% oxygenated water were added to the mixture and the mixture was stirred under an inert atmosphere at 0° C. for 23 hours and was poured into a mixture of 200 g of ice and 200 ml of 0.5M sodium thiosulfate solution. The mixture was stirred for 30 minutes and was extracted with methylene chloride containing a trace of pyridine. The organic phase was washed with water, dried and evaporated to dryness to obtain 11.4 g of 3,3-[1,2-ethanediyl-bisoxy]-5α,10α-epoxy-Δ$^{9(11)}$-estrene-17-one which was used as is for the next step.

STEP B: 3,3-[1,2-ethanediyl-bisoxy]-11β-[4-(N,N-dimethylamino)-phenyl]-Δ$^9$-estrene-5α-ol-17-one A mixture of 200 g of 4-dimethylamino benzene bromide in 950 ml of anhydrous tetrahydrofuran was added over 2½ hours at 35° C. ±5° C. to a mixture of 29 g of magnesium turnings and 50 ml of anhydrous tetrahydrofuran under an inert atmosphere to obtain a solution of 0.8M of magnesium.

284 ml of the said magnesium solution were added dropwise over 75 minutes at 0° to 5° C. under an inert atmosphere to a mixture of 25 g of the product of Step A, 500 ml of anhydrous tetrahydrofuran and 0.757 g of copper chloride and the mixture was stirred for 15 minutes and poured into aqueous saturated ammonium chloride solution. The mixture was extracted with ethyl acetate and the organic phase was washed with aqueous saturated ammonium chloride solution and with aqueous saturated sodium chloride solution, dried and evaporated to dryness under reduced pressure. The 46 g of residue were chromatographed over silica gel and were eluted with a 1-1 petroleum ether-ethyl acetate mixture containing 1 ppm of triethylamine to obtain 17.76 g of product melting at 178° C. The impure fractions were subjected again to chromatography over silica gel and were eluted with an 8-2 petroleum ether-acetone mixture containing 1 ppm of triethylamine to obtain another 6.35 g of 3,3-[1,2-ethanediyl-bisoxy]-11β-[4-(N,N-dimethylamino)-phenyl]-Δ$^9$-estrene-5α-ol-17-one melting at 176° C. which was used as is for the next step.

STEP C: 3,3-[1,2-ethanediyl-bisoxy]-11β-[4-(N,N-dimethylamino)-phenyl]-17α-phenyl-Δ$^9$-estrene-5α,17β-diol A solution of 4.51 g of the product of Step B in 45.1 ml of anhydrous tetrahydrofuran was added over 30 minutes at 25° C. to a solution of 33.3 ml of phenyllithium (1.5 moles) and the mixture was stirred for 4 hours at room temperature and was then poured into aqueous saturated ammonium chloride solution. The mixture was extracted with ether and the organic phase was washed with aqueous saturated sodium chloride solution, dried and evaporated to dryness. The 5.6 g of residue were chromatographed over silica gel and were eluted with a 9-1 methylene chloride-acetone mixture containing of triethylamine to obtain 1.16 g of 3,3-[1,2-ethanediyl-bisoxy]-11β-[4-(N,N-dimethylamino)-phenyl]-17α-phenyl-Δ$^9$-estrene-5α,17β-diol which after crystallization from an isopropyl ether-methylene chloride mixture melted at 240° C. and had a specific rotation of $[\alpha]_D^{20} = +53° \pm 2.5°$ (c=0.5% in CHCl$_3$).

STEP D: 11β-[4-(N,N-dimethylamino)-phenyl]-17α-phenyl-Δ$^{4,9}$-estradiene-17β-ol-3-one 3 ml of 2N hydrochloric acid were added under an inert atmosphere at 0° to 5° C. to a mixture of 1.5 g of the product of Step C in 45 ml of methanol and the mixture was stirred at 0° to 5° C. for one hour. Then, 90 ml of ether and 90 ml of an aqueous 0.25M of sodium bicarbonate solution were added to the mixture and the mixture was stirred for 5 minutes. The decanted aqueous phase was extracted with ether and the organic phase was washed with aqueous saturated sodium chloride solution, dried and evaporated to dryness. The 1.3 g of residue were chromatographed over silica gel and were eluted with a 1-1 petroleum ether ether mixture to obtain 0.93 g of 11β-[4-(N,N-dimethylamino)-phenyl]-17α-phenyl-Δ$^{4,9}$-estradiene-17β-ol-3-one which after crystallization from methylene chloride-isopropyl ether melted at 226° C. and had a specific rotation of $[\alpha]_D^{20} = +151.5°$ (c=0.4% in chloroform).

EXAMPLE 23

11β-[4-(N,N-dimethylamino)-phenyl]-23-methyl-19,21-dinor-17α-Δ$^{4,9,23}$-cholatriene-20-yn-17β-ol-3-one STEP A: 3,3-[1,2-ethanediyl-bisoxy]-11β-[4-(N,N-dimethylamino)-phenyl]-23-methyl-19,21-dinor-17α-Δ$^{9,23}$-choladiene-20-yn-5α,17β-diol 10.61 ml of 2-methyl-1-buten-3-yne were added under an inert atmosphere to a mixture of 4.5 g of potassium tert.-butylate in 90 ml of anhydrous tetrahydrofuran and the mixture was stirred for 15 minutes at −10° C. A solution of 4.5 g of the product of Step B of Example 22 in 45 ml of anhydrous tetrahydrofuran was added over 15 minutes to the reaction mixture and the mixture was stirred at −10° C. for 30 minutes and then for 4 hours at 0° to 5° C. The mixture was poured into 500 ml of aqueous saturated solution of ammonium chloride and the mixture was extracted with ethyl acetate. The organic phase was washed with aqueous saturated sodium chloride solution, dried and evaporated to dryness to obtain 5.56 g of raw 3,3-[1,2-ethanediyl-bisoxy]-11β-[4-(N,N-dimethylamino)-phenyl]-23-methyl-19,21-dinor-17α-Δ$^{9,23}$-choladiene-20-yn-5α,17β-diol melting at 205° C. which was used as is for the next step. The raw product was chromatographed over silica gel and was eluted with a 9-1 methylene chloride-ethyl acetate containing 1 part per 1000 of triethylamine and crystallized from ethyl acetate to obtain the product melting at 215° C.

STEP B: 11β-[4-(N,N-dimethylamino)-phenyl]-23-methyl-19,21-dinor-17α-Δ$^{4,9,23}$-cholatriene-20-yne-17β-ol-3-one A mixture of 5 g of the product of Step A, 300 ml of methanol and 10 ml of 2N hydrochloric acid was stirred under an inert atmosphere for 15 minutes at 20° C. and then 300 ml of methylene chloride and then 300 ml of aqueous 0.25M sodium bicarbonate solution were added thereto. The mixture was stirred for 10 minutes and the decanted aqueous phase was extracted with methylene chloride. The organic phase was washed with water, dried and evaporated to dryness. The 4.5 g of residue were chromatographed over silica gel and were eluted with a 1-1 petroleum ether-ethyl acetate mixture to obtain after crystallization from diisopropyl oxide 2.01 g of 11β-[4-(N,N-dimethylamino)-phenyl]-23-methyl-19,21-dinor-17α-Δ$^{4,9,23}$-cholatriene-20-yne-17β-ol-3-one melting at 185° C. and having a specific rotation of $[\alpha]_D^{20} = +88.5° \pm 1.5°$ (c=1% in CHCl$_3$).

EXAMPLE 24

11β-[4-(N,N-dimethylamino)-phenyl]-17β-methoxy-23-methyl-19,21-dinor-17α-Δ$^{4,9,23}$-cholatriene-20-yne-3-one 10.61 ml of 2-methyl-1-buten-3-yne were added dropwise at −10° C. to a suspension of 4.5 g of potassium tert.-butylate in 90 ml of anhydrous tetrahydrofuran under an inert atmosphere and the mixture was stirred at −10° C. for 15 minutes. Then, a mixture of 4.5 g of the product of Step B of Example 22 in 45 ml of anhydrous tetrahydrofuran was added over 15 minutes to the mixture which was then stirred at −10° C. for 30 minutes) and at 0° to 5° C. for 4 hours. 7.5 ml of methyl iodide were added to the mixture which was then stirred in an ice bath for 30 minutes and then poured into 500 ml of 0.1N hydrochloric acid. The mixture was stirred for 30 minutes at room temperature and was then extracted with ethyl acetate. The organic phase was washed with aqueous saturated sodium bicarbonate solution, then with aqueous saturated sodium chloride solution, dried and evaporated to dryness. The residue was chromatographed over silica gel and was eluted with a 95-5 methylene chloride-ethyl acetate mixture to obtain 2.7 g of 11β-[4-(N,N-dimethylamino)-phenyl]-17β-methoxy-23-methyl-19,21-dinor-17α-Δ$^{4,9,23}$-cholatriene-20-yne-3-one which after crystallization from methanol melted at 105° C.

EXAMPLE 25

11β-[4-(N,N-dimethylamino)-phenyl]-21-chloro-19-nor-17α-Δ$^{4,9}$-pregnadiene-20-yne-17β-ol-3-one STEP A: 3,3-[1,2-ethanediyl-bisoxy]-11β-[4-(N,N-dimethylamino)-phenyl]-21-chloro-19-nor-17α-Δ$^9$-pregnene-20-yne-5α,17β-diol A solution of 7 ml of trichloroethylene in 28 ml of anhydrous ether was added with stirring under an inert atmosphere at 0° to 5° C. to a mixture of 77.5 ml of 1M butyllithium in hexane and 310 ml of anhydrous ether and the mixture was stirred for one hour while the temperature rose to 20° C. A solution of 7 g of Step B of Example 22 in 70 ml of tetrahydrofuran was added to the resulting mixture dropwise over 30 minutes at 0° to 5° C. and the mixture was stirred at 0° to 5° C. for 30 minutes after which the temperature was allowed to rise to 20° C. and was slowly poured into an aqueous saturated ammonium chloride solution and the decanted aqueous phase was extracted with methylene chloride. The organic phase was washed with water, dried and evaporated to dryness to obtain 8.5 g of raw product melting at 220° C. The latter was added to 42.5 ml of diisopropyl oxide and the mixture was stirred for 30 minutes and vacuum filtered to obtain 6.38 g of product melting at 230° C. The latter was chromatographed over silica gel and was eluted with a 7-3 benzene-ethyl acetate mixture containing 1 ppm of triethylamine. The product was dissolved in methylene chloride and was precipitated by addition of diisopropyl oxide to obtain 3,3-[1,2-ethanediyl-bisoxy]-11β-[4-(N,N-dimethylamino)-phenyl]-21-chloro-19-nor-17α-Δ$^9$-pregnene-20-yne-5α,17β-diol melting at 240° C. and having a specific rotation of $[\alpha]_D^{20} = -83.5° \pm 1.5°$ (c=1% in CHCl$_3$).

STEP B: 11β-[4-(N,N-dimethylamino)-phenyl]-21-chloro-19-nor-17α-Δ$^{4,9}$-pregnadiene-20-yne-17β-ol-3-one 15 ml of 2N hydrochloric acid were added under an inert atmosphere to a mixture of 6.38 g of the product of Step A in 191.4 ml of 95% ethanol and after stirring the mixture for one hour, 300 ml of methylene chloride and then 200 ml of aqueous 0.25 mm sodium bicarbonate solution were added thereto. The decanted aqueous phase was extracted with methylene chloride and the organic phase was washed with water, dried and evaporated to dryness under reduced pressure. The 6 g of residue were chromatographed over silica gel and were eluted with a 7-3 benzene-ethyl acetate mixture to obtain 3.95 g of 11β-[4-(N,N-dimethylamino)-phenyl]-21-chloro-19-nor-17α-Δ$^{4,9}$-pregnadiene-20-yne-17β-ol-3-one which after crystallization from ethyl acetate melted at 240° C. and had a specific rotation of $[\alpha]_D^{20} = +111° \pm 2°$ (c=1% in chloroform).

EXAMPLE 26

N-oxide of 11β-[4-(N,N-dimethylamino)-phenyl]21-chloro-19-nor-17α-Δ$^{4,9}$-pregnadiene-20-yne-17β-ol-3-one A mixture of 0.54 g of 85% M-chloroperbenzoic acid in 10.8 ml of methylene chloride was added under an inert atmosphere at 0° to 5° C. to a mixture of 1.2 g of the product of Example 25 in 24 ml of methylene chloride and the mixture was stirred for one hour at 0° to 5° C. and was then poured into aqueous 0.2N sodium thiosulfate solution. The mixture was extracted with methylene chloride and the organic phase was washed with aqueous saturated sodium bicarbonate solution, with water, dried and evaporated to dryness. The 1.3 g of residue was chromatographed over silica gel and was eluted with a 7-3 methylene chloride-methanol mixture to obtain 1.15 g of N-oxide of 11β-[4-(N,N-dimethylamino)-phenyl]-21-chloro-19-nor-17α-Δ$^{4,9}$-pregnadiene-20-yne-17β-ol-3-one with a specific rotation of $[\alpha]_D^{20} = +47.5° \pm 1.5°$ (c=0.7% in chloroform).

EXAMPLE 27

N-oxide of 11β-[4-(N,N-dimethylamino)-phenyl]-9α,10α-epoxy-21-chloro-19-nor-17α-Δ$^4$-pregnene-20-yne-17β-ol-3-one A mixture of 1.17 g of 85% m-chloroperbenzoic acid in 23.4 ml of methylene chloride was added over 15 minutes at 0° to 5° C. to a solution of 1.18 g of the product of Example 25 in 23.6 ml of methylene chloride and the mixture was stirred for 2 hours at 20° C. after which another 1.17 g of 85% M-chloroperbenzoic acid were added. The mixture was stirred for one hour and was poured into a solution of aqueous 0.2N sodium thiosulfate. The mixture was extracted with methylene chloride and the organic phase was washed with aqueous saturated sodium bicarbonate solution and then with water, dried and evaporated to dryness to obtain 1.14 g of residue melting at 220° C. The residue was chromatographed over silica gel and was eluted with an 8-2 methylene chloride-methanol mixture to obtain 1 g of N-oxide of 11β-[4-(N,N-dimethylamino)-phenyl]-9α,10α-epoxy-21-chloro-19-nor-17α-Δ$^4$-pregnene-20-yne-17β-ol-3-one melting at 270° C. and having a specific rotation of $[\alpha]_D^{20} = +39.5° \pm 2.5°$ (c=0.5% in chloroform).

EXAMPLE 28

9α,10α-epoxy-11β-[4-(N,N-dimethylamino)-phenyl]-21-chloro-19-nor-17α-Δ$^4$-pregnene-20-yne-17β-ol-3-one 0.34 g of triphenylphosphine were added under an inert atmosphere to a mixture of 0.63 g of the product of Example 27 in 6.3 ml of acetic acid and the mixture was stirred at room temperature for 45 minutes and was then poured into water. The mixture was extracted with methylene chloride and the organic phase was washed with water, dried and evaporated to dryness. The 0.9 g of residue was chromatographed over silica gel and was eluted with a 1-1 petroleum ether-ethyl acetate mixture. The product was crystallized from a methylene chloride-isopropyl ether mixture to obtain 0.346 g of 9α,10α-epoxy-11β-[4-(N,N-dimethylamino)-phenyl]-21-chloro-19-nor-17α-Δ$^4$-pregnene-20-yne-17β-ol-3-one melting at 265° C. and having a specific rotation of $[\alpha]_D^{20} = +45° \pm 2°$ (c=0.8% in chloroform).

EXAMPLE 29

11β-[4-(N,N-dimethylamino)-phenyl]-21-phenyl-19-nor-17α-Δ$^{4,9}$-pregnadiene-20-yne-17β-ol-3-one STEP A: 3,3-[1,2-ethanediyl-bisoxy]-11β-[4-(N,N-dimethylamino)-phenyl]-21-phenyl-19-nor-17α-Δ$^9$-pregnene-20-yne-5α,17-diol A mixture of 4.17 g of potassium tert.-butylate in 83 ml of anhydrous tetrahydrofuran was stirred under an inert atmosphere for 10 minutes and then 4.5 ml of phenyl acetylene were added dropwise at −10° C. The suspension was stirred for 5 minutes and then a solution of 4.17 g of the product of Step B of Example 22 in 41 ml of anhydrous tetrahydrofuran was added thereto dropwise at −10° C. Then, the temperature rose to 0° C. and held there for one hour and was then poured into an aqueous saturated ammonium chloride solution. The mixture was extracted with ether and the organic phase was washed with aqueous saturated sodium chloride solution, dried and evaporated to dryness. The 4.7 g of residue were chromatographed over silica gel and eluted with a 95-5 methylene chloride-acetone mixture to obtain 3.71 of of 3,3-[1,2-ethanediyl-bisoxy]-11β-[4-(N,N-dimethylamino-phenyl]-21-phenyl-19-nor-17α-Δ$^9$-pregnene-20-yne-5α,17β-diol melting at 168° C. and having a specific rotation of $[\alpha]_D^{20} = -119.5° \pm 2°$ (c=1% in chloroform).

STEP B: 11β-[4-(N,N-dimethylamino)-phenyl]-21-phenyl-19-nor-17α-Δ$^{4,9}$-pregnadiene-20-yne-17β-ol-3-one 6.3 ml of 2N hydrochloric acid were added to a solution of 3.49 g of the product of Step A in 68 ml of methanol and the mixture was stirred for 30 minutes and was poured into a mixture of 180 ml of ether and 90 ml of aqueous 0.25M sodium bicarbonate solution. The mixture was stirred for 5 minutes and the decanted aqueous phase was extracted with ether. The organic phase was washed with aqueous 0.25M sodium bicarbonate solution, then with aqueous sodium chloride, dried and evaporated to dryness. The 4.35 g of residue were chromatographed over silica gel and eluted with with a 95-5 methylene chloride-acetone mixture to obtain 2.13 g of 11β-[4-(N,N-dimethylamino)-phenyl]-21-phenyl-19-nor-17α-Δ$^{4,9}$-pregnadiene-20-yne-17β-ol-3-one which after crystallization from isopropyl ether had a specific rotation of $[\alpha]_D^{20} = +22.5° \pm 1°$ (c=1% in chloroform).

EXAMPLE 30

11β-[4-(N,N-dimethylamino)-phenyl]-17α-(propa-1,2-dienyl)-Δ⁴,⁹-estradiene-17β-ol-3-one STEP A: 3,3-[1,2-ethanediyl-bisoxy]-11β-[4-(N,N-dimethylamino)-phenyl]-17α-(propa-1,2-dienyl)-Δ⁹-estrene-5α,17β-diol and 3,3-[1,2-ethanediyl-bisoxy]-11β-[4-(N,N-dimethylamino)-phenyl]-17α-(prop-2-ynyl)-Δ⁹-estrene-5α,17β-diol Allene was bubbled into 50 ml of anhydrous tetrahydrofuran at 0° to 5° C. until 2.1 g were absorbed and 23.9 ml of a solution of a 1.3M of butyllithium in hexane were added thereto over 15 minutes at −70° C. The mixture was stirred at −70° C. for 15 minutes and then a solution of 3.5 g of the product of Step B of Example 22 in 35 ml of anhydrous tetrahydrofuran were added thereto at −70° C. over 25 minutes. The mixture was stirred at −70° C. for one hour and was poured slowly into an iced aqueous saturated ammonium chloride solution. The mixture was extracted with ether and the organic phase was washed with aqueous saturated sodium chloride solution, dried and evaporated to dryness. The 3.4 g of residue were chromatographed over silica gel and eluted with a 1-1 petroleum ether-ethyl acetate mixture containing 1 ppm of triethylamine to obtain 1.73 g of 3,3-[1,2-ethanediyl-bisoxy]-11β-[4-(N,N-dimethylamino)-phenyl]-17α-(propa-1,2-dienyl)-Δ⁹-estrene-5α,17β-diol melting at 178° C. and having a specific rotation of $[\alpha]_D^{20} = -32° \pm 2°$ (c=0.7% in chloroform) and 1.5 g of 3,3-[1,2-ethanediyl-bisoxy]-11β-[4-(N,N-dimethylamino)-phenyl]-17α-(prop-2-ynyl)-Δ⁹-estrene-5α,17β-diol melting at 150° C. and having a specific rotation of $[\alpha]_D^{20} = -15° \pm 2°$ (c=0.9% in chloroform).

STEP B: 11β-[4-(N,N-dimethylamino)-phenyl]-17α-(propa-1,2-dienyl)-Δ⁴,⁹-estradiene-17β-ol-3-one A mixture of 1.73 g of the 17α-(propa-1,2-dienyl)isomer of Step A, 51.8 ml of 95% ethanol and 3.5 ml of 2N hydrochloric acid was stirred under an inert atmosphere at 20° C. for one hour and then 50 ml of methylene chloride and 50 ml of aqueous 0.25M sodium bicarbonate solution were added thereto. The decanted aqueous phase was extracted with methylene chloride and the organic phase was washed with water, dried and evaporated to dryness. The 1.51 g of residue were dissolved in 10 ml of hot methylene chloride and 15 ml of isopropyl ether were added to the solution. The mixture was concentrated and allowed to stand to obtain 1.23 g of product which were crystallized form a methylene chloride-isopropyl ether mixture to obtain 1.11 g of 11β-[4-(N,N-dimethylamino)-phenyl]-17α-(propa-1,2-dienyl)-Δ⁴,⁹-estradiene-17β-ol-3-one melting at 228° C. and having a specific rotation of $[\alpha]_D^{20} = +139.5° \pm 3°$ (c=0.8% in chloroform).

EXAMPLE 31

11β-[4-(N,N-dimethylamino)-phenyl]-17α-(prop-2-ynyl)-Δ⁴,⁹-estradiene-17β-ol-3-one A mixture of 0.94 g of the 17α-(prop-2-ynyl)-isomer of Step A of Example 30, 28.2 ml of 95% ethanol and 2 ml of 2N hydrochloric acid was stirred at 20° C. for one hour and then 50 ml of methylene chloride and 50 ml of an aqueous 0.25M sodium bicarbonate solution were added thereto. The mixture was stirred for 5 minutes and the decanted aqueous phase was extracted with methylene chloride. The organic phase was washed with water, dried and evaporated to dryness and the residue was chromatographed over silica gel. Elution with a 1-1 petroleum ether-ethyl acetate mixture yielded 0.42 g of 11β-[4-(N,N-dimethylamino)-phenyl]-17α-(prop-2-ynyl)-Δ⁴,⁹-estradiene-17β-ol-3-one with a specific rotation of $[\alpha]_D^{20} = +143° \pm 3°$ (c=0.8% in chloroform).

EXAMPLE 32

11β-[4-(N,N-dimethylamino)-phenyl]-17α-ethynyl-Δ⁴,⁹-estradiene-17β-ol-3-one

STEP A: 3,3-[1,2-ethanediyl-bisoxy]-11β-[4-(N,N-dimethylamino)-phenyl]-17β-cyano-17α-trimethylsilyloxy-Δ⁹-estrene-5α-ol A solution of 13 mmoles of [4-(N,N-dimethylamino)-phenyl]-magnesium bromide in anhydrous tetrahydrofuran was added under an inert atmosphere to a suspension of 2.05 g of dimethylsulfide-copper bromide complex in 10 ml of anhydrous tetrahydrofuran and the mixture was stirred for 30 minutes after which 20 ml of anhydrous triethylamine were added thereto. A solution of 0.95 g of 3,3-[1,2-ethanediyl-bisoxy]-5α,10α-epoxy-17β-cyano-17α-trimethylsilyloxy-Δ⁹⁽¹¹⁾-estrene in anhydrous tetrahydrofuran were added to the mixture which was then stirred for 15 hours at room temperature and poured into 50 ml of aqueous saturated ammonium chloride solution. The decanted aqueous phase was extracted with ether and the organic phase was washed with water, dried and evaporated to dryness. The residue was chromatographed over silica gel and was eluted with an 8-2 benzene-ethyl acetate mixture to obtain 1.1 g of 3,3-[1,2-ethanediyl-bisoxy]-11β-[4-(N,N-dimethylamino)-phenyl]-17β-cyano-17α-trimethylsilyloxy-Δ⁹-estrene-5α-ol which after crystallization from isopropyl ether melted at 247° C. and had a specific rotation of $[\alpha]_D^{20} = -12.5°$ (c=1% in chloroform).

STEP B: 3,3-[1,2-ethanediyl-bisoxy]-11β-[4-(N,N-dimethylamino)-phenyl]-17α-ethynyl-Δ⁹-estrene-5α,17β-diol 1 g of the acetylide complex of lithium ethylenediamine was added to a mixture of 0.8 g of the product of Step A in 8 ml of ethylenediamine and the mixture was stirred under an inert atmosphere at −50° C. for 90 minutes. The mixture was cooled to 20° C. and was poured into aqueous ammonium chloride solution. The mixture was extracted with ether and methylene chloride and the organic phase was dried and evaporated to dryness. The residue was chromatographed over silica gel and was eluted with a 7-3 benzene-ethyl acetate mixture. The product was crystallized from isopropyl ether to obtain 0.43 g of 3,3-[1,2-ethanediyl-bisoxy]-11β-[4-(N,N-dimethylamino)-phenyl]-17α-ethynyl-Δ⁹-estrene-5α,17β-diol melting at 199° C. and having a specific rotation of $[\alpha]_D^{20} = -43° \pm 1.5°$ (c=1% in chloroform).

STEP C: 11β-[4-(N,N-dimethylamino)-phenyl]-17α-ethynyl-Δ⁴,⁹-estradiene-17β-ol-3-one 1 ml of 2N hydrochloric acid was added to a solution of 0.25 g of the product of Step B in 6 ml of methanol and the mixture was stirred at 20° C. for 40 minutes and then was poured into water containing 2.5 ml of N sodium hydroxide. The mixture was extracted with ether and the organic phase was dried and evaporated to dryness. The residue was chromatographed over silica gel and was eluted with a 7-3 benzene-ethyl acetate mixture to obtain 0.25 of 11β-[4-(N,N-dimethylamino)-phenyl]-17α-ethynyl-Δ⁴,⁹-estradiene-17β-ol-3-one.

| Analysis: $C_{23}H_{33}NO_2$; molecular weight = 415.54 | | | |
|---|---|---|---|
| Calculated: | % C 80.92 | % H 8.00 | % N 3.37 |
| Found: | 80.7 | 8.1 | 3.1 |

EXAMPLE 33

11β-[4-(N,N-dimethylamino)-phenyl]-17α-ethynyl-Δ⁴,⁹-estradiene-17β-ol-3-one

STEP A: 3,3-[1,2-ethanediyl-bisoxy]-11β-[4-(N,N-dimethylamino)-phenyl]-17α-ethynyl-Δ⁹-estrene-5α,17β-diol 12.25 g of the acetylide complex of lithium ethylenediamine were added under an inert atmosphere to a solution of 6 g of the product of Step B of Example 22 in 180 ml of tetrahydrofuran and the mixture was stirred at 55° C. for 4 hours and was then cooled and poured into 600 ml of an iced aqueous saturated ammonium chloride solution. The mixture was extracted with ether and the organic phase was washed with aqueous saturated sodium chloride solution, dried and evaporated to dryness. The residue was chromatographed over silica gel and eluted with a 7-3 benzene-ethyl acetate mixture containing 1 ppm of triethylamine. The 4.5 g of product was crystallized from a methylene chloride-diisopropyl oxide mixture to obtain 3,3-[1,2-ethanediyl-bisoxy]-11β-[4-(N,N-dimethylamino)-phenyl]-17α-ethynyl-Δ⁹-estrene-5α,17β-diol melting at 202° C. and having a specific rotation of $[\alpha]_D^{20} = -47.5° \pm 1.5°$ (c = 1% in chloroform).

STEP B: 11β-[4-(N,N-dimethylamino)-phenyl]-17α-ethynyl-Δ⁴,⁹-estradiene-17β-ol-3-one 5 ml of 2N hydrochloric acid were added to a suspension of 2 g of the product of Step A in 50 ml of 95% ethanol and the mixture was stirred at 20° C. for one hour. 100 ml of ether and then 100 ml of aqueous. 0.25M sodium bicarbonate solution were added to the mixture and the decanted aqueous phase was extracted with ether. The organic phase was washed with aqueous saturated sodium chloride solution, dried and evaporated to dryness and the residue was chromatographed over silica gel. Elution with a 6-4 petroleum ether-ethyl acetate mixture yielded 1.52 g of 11β-[4-(N,N-dimethylamino)-phenyl]-17α-ethynyl-Δ⁴,⁹-estradiene-17β-ol-3-one which after crystallization from diisopropyl oxide melted at 172° C. and had a specific rotation of $[\alpha]_D^{20} = +182° \pm 2.5°$ (c = 1% in chloroform).

EXAMPLE 34

11β-[3-(N,N-dimethylamino)-phenyl]-17α-(prop-1-ynyl)-Δ⁴,⁹-estradiene-17β-ol-3-one STEP A: 3,3-[1,2-ethanediyl-bisoxy]-11β-[3-(N,N-dimethylamino)-phenyl]-17α-(prop-1-ynyl)-Δ⁹-estrene-5α,17β-diol A mixture of 10 g of m-bromo-dimethylaniline in 45 ml of anhydrous tetrahydrofuran was added under an inert atmosphere over 45 minutes to a mixture of 1.46 g of magnesium and 5 ml of anhydrous tetrahydrofuran and the reaction was started by addition of dibromomethane. The mixture was stirred for one hour to obtain a solution of 0.95M of magnesium and 42.2 ml of the solution were added at 0° to 5° C. over 30 minutes under an inert atmosphere to a mixture of 3.7 g of 3,3-[1,2-ethanediyl-bisoxy]-5α,10α-epoxy-17α-(prop-1-ynyl)-Δ⁹(¹¹)-estrene-17β-ol, 74 ml of anhydrous tetrahydrofuran and 99 mg of copper chloride and the mixture was stirred for 30 minutes at 0° to 5° C. and was poured into an aqueous saturated ammonium chloride solution. The mixture was extracted with ether and the organic phase was washed with aqueous saturated sodium chloride solution, dried and evaporated to dryness. The residue was chromatographed over silica gel and eluted with a 9-1 methylene chloride-acetone mixture containing 1 part per 1000 triethylamine to obtain 3.5 g of 3,3-[1,2-ethanediyl-bisoxy]-11β-[3-(N,N-dimethylamino)-phenyl]-17α-(prop-1-ynyl)-Δ⁹-estrene-5α,17β-diol melting at 262° C. and having a specific rotation of $[\alpha]_D^{20} = -64° \pm 1.5°$ (c = 1% in chloroform) and 0.66 g of the corresponding 5β-ol isomer melting at 210° C. and having a specific rotation of $[\alpha]_D^{20} = +32.5° \pm 1°$ (c = 0.8% in chloroform).

STEP B: 11β-[3-(N,N-dimethylamino)-phenyl]-17α-(prop-1-ynyl)-Δ⁴,⁹-estradiene-17β-ol-3-one 10 ml of 2N hydrochloric acid were added at 0° to 5° C. under an inert gas to a mixture of 3.3 g of the product of step A in 100 ml of methanol and the mixture was stirred at 0° to 5° C. for one hour. 200 ml of diethyl oxide and then 200 ml of aqueous 0.25M sodium bicarbonate solution were added to the mixture which was then stirred for 5 minutes. The decanted aqueous phase was extracted with diethyloxide and the organic phase was washed with aqueous saturated sodium chloride solution, dried and evaporated to dryness. The 3 g of residue were chromatographed over silica gel and eluted with a 7-3 benzene-ethyl acetate mixture to obtain 1.43 g of amphorous 11β-[3-(N,N-dimethylamino)-phenyl]-17α-(prop-1-ynyl)-Δ⁴,⁹-estradiene-17β-ol-3-one with a specific rotation of $[\alpha]_D^{20} = -43° \pm 2.5°$ (c = 1% in CHCl₃).

EXAMPLE 35

N-oxide of 11β-[4-(N,N-dimethylamino)-phenyl]-17α-(prop-1-ynyl)-Δ⁴,⁹-estradiene-17β-ol-3-one A solution of 0.71 g of 85% m-chloroperbenzoic acid in 14.2 ml of methylene chloride was added over 10 minutes at 0° to 5° C. to a mixture of 1.5 g of the product of Example 19 in 30 ml of methylene chloride and the mixture was stirred for one hour at 0° to 5° C. and was poured into 100 ml of an aqueous 0.2N sodium thiosulfate solution. The decanted aqueous phase was extracted with methylene chloride and the organic phase was washed with aqueous 0.5M sodium bicarbonate solution, dried and evaporated to dryness. The residue was dissolved in 20 ml of methylene chloride and 20 ml of diisopropyl oxide were added thereto. Crystallization was induced and the mixture stood for a while and was vacuum filtered. The crystals were dried to obtain 1.4 g of N-oxide of 11β-[4-(N,N-dimethylamino)-phenyl]-17α-(prop-1-ynyl)-Δ⁴,⁹-estradiene-17β-ol-3-one melting at 210° C. and having a specific rotation of $[\alpha]_D^{20} = +73.5° \pm 2°$ (c = 1% in chloroform).

EXAMPLE 36

11β-[4-(N,N-dimethylamino)-phenyl]-Δ⁴,⁹-estradiene-17β-ol-3-one 106 mg of sodium borohydride were added to a solution of 1 g of the product of Step B of Example 22 in 20 ml of tetrahydrofuran containing 10% water and the mixture was stirred for one hour and poured into 200 ml of water. The mixture was extracted with methylene chloride and the organic phase was washed with aqueous saturated sodium chloride solution, dried and evaporated to dryness to obtain 1.3 g of 11β-[4-(N,N-dimethylamino)-phenyl]-Δ$^{4,9}$-estradiene-5α,17β-diol-3-one. 0.63 g of the latter were added to a mixture of 12 ml of methanol and 2.4 ml of 2N hydrochloric acid and the mixture was stirred at room temperature for 90 minutes and was poured into aqueous sodium bicarbonate. The mixture was extracted with ether and the organic phase was washed with aqueous saturated sodium chloride solution, dried and evaporated to dryness. The residue was chromatographed over silica gel and was eluted with a 6-4 petroleum ether-ethyl acetate mixture. The residue was triturated with petroleum ether and vacuum filtered to obtain 0.38 g of 11β-[4-(N,N-dimethylamino)-phenyl]-Δ$^{4,9}$-estradiene-17β-ol-3-one melting at 130° C. and having a specific rotation of $[\alpha]_D^{20} = +277° \pm 5°$ (c=0.5% in chloroform).

EXAMPLE 37

11β-[4-(N,N-dimethylamino)-phenyl]-17α-(prop-2-enyl)-Δ$^{4,9}$-estradien-17β-ol-3-one STEP A: 3,3-[1,2-ethanediyl-bisoxy]-11β-[4-(N,N-dimethylamino)-phenyl]-17α-(prop-2-enyl)-Δ$^9$-estrene-5α,17β-diol A solution of 3.5 g of the product of Step B of Example 22 in 35 ml of tetrahydrofuran was added under an inert atmosphere at 20° C. over 15 minutes to 55.5 ml of 0.7M allyl magnesium bromide in ether and the mixture was stirred at 20° C. for one hour and was then poured into an aqueous saturated ammonium chloride solution. The mixture was extracted with ether and the organic phase was washed with aqueous saturated sodium chloride solution, dried and evaporated to dryness. The residue was dissolved in 10 ml of methylene chloride and 15 ml of diisopropyl oxide were added to the solution which was then concentrated and allowed to stand. The mixture was vacuum filtered and the crystals were rinsed with diisopropyl oxide and dried to obtain 2.76 g of 3,3-[1,2-ethanediyl-bisoxy]-11β-[4-(N,N-dimethylamino)-phenyl]-17α-(prop-2-enyl)-Δ$^9$-estrene-5α,17β-diol melting at 198° C.

| Analysis: C$_{31}$H$_{43}$NO$_4$; molecular weight = 493.69 | | |
|---|---|---|
| % C | % H | % N |
| Calculated: 74.42 | 8.78 | 2.83 |
| Found: 74.0 | 8.7 | 2.9 |

STEP B: 11β-[4-(N,N-dimethylamino)-phenyl]-17α-(prop-2-enyl)-Δ$^{4,9}$-estradiene-17β-ol-3-one 4.5 ml of 2N hydrochloric acid were added to a suspension of 2.2 g of the product of Step A in 66 ml of methanol and the mixture was stirred at 20° C. for 30 minutes after which 132 ml of diethyl oxide and then 132 ml of aqueous 0.25M sodium bicarbonate solution were added thereto. The decanted aqueous phase was extracted with diethyl oxide and the organic phase was washed with aqueous saturated sodium chloride solution, dried and evaporated to dryness. The residue was chromatographed over silica gel and was eluted with a 7-3 benzene-ethyl acetate mixture. The product was taken up in a mixture of 15 ml of diisopropyl oxide and 7.5 ml of methylene chloride and the solution was concentrated and allowed to stand. The mixture was vacuum filtered and the crystals were rinsed with diisopropyl oxide and dried to obtain 1.365 g of 11β-[4-(N,N-dimethylamino)-phenyl]-17α-(prop-2-enyl)-Δ$^{4,9}$-estradiene-17β-ol-3-one melting at 182° C. and having a specific roation of $[\alpha]_D^{20} = +206.5° \pm 3°$ (c=1% in chloroform).

EXAMPLE 38

11β-[4-(N,N-dimethylaminomethyl)-phenyl]-17α-(prop-1-ynyl)-Δ$^{4,9}$-estradiene-17β-ol-3-one STEP A: 3,3-[1,2-ethanediyl-bisoxy]-11β-[4-(N,N-dimethylaminomethyl)-phenyl]-17α-(prop-1-ynyl)-Δ$^9$-estrene-5α,17β-diol A solution of 42.8 g of 4-(N,N-dimethylaminomethyl)-bromobenzene in 190 ml of anhydrous tetrahydrofuran was added over 90 minutes under an inert atmosphere at 45° to 50° C. to a mixture of 5.5 g of magnesium in 10 ml of anhydrous tetrahydrofuran and the reaction was induced with dibromoethane addition. The mixture was stirred for one hour to obtain an 0.85M magnesium solution and 127 ml of the said solution were added under an inert atmosphere at 0° to 5° C. over one hour to a mixture of 10 g of 3,3-[1,2-ethanediyl-bisoxy]-5α,10α-epoxy-17α-(prop-1-ynyl)-Δ$^{9(11)}$-estrene-17β-ol, 200 ml of anhydrous tetrahydrofuran and 0.27 g of copper chloride. The mixture was stirred for 15 minutes and was poured into an aqueous saturated ammonium chloride solution. The mixture was extracted with ether and the organic phase was washed with aqueous saturated sodium chloride solution, dried and evaporated to dryness. The residue was chromatographed over silica gel and was eluted with a 9-1 methylene chloride-methanol mixture containing 1 part per 1000 of triethylamine to obtain 10.1 g of product. The latter was dissolved in methylene chloride and a few drops of methanol and then diisopropyl oxide were added thereto. The mixture was concentrated, allowed to stand for 6 hours and was vacuum filtered to obtain 7.37 g of 3,3-[1,2-ethanediyl-bisoxy]-11β-[4-(N,N-dimethylaminomethyl)-phenyl]-17α-(prop-1-ynyl)-Δ$^9$-estrene-5α,17β-diol melting at 186° C. and having a specific rotation of $[\alpha]_D^{20} = -63° \pm 2.5°$ (c=0.5% in chloroform).

STEP B: 11β-[4-(N,N-dimethylaminomethyl)-phenyl]-17α-(prop-1-ynyl)-Δ$^{4,9}$-estradiene-17β-ol-3-one A mixture of 15 ml of 2N hydrochloric acid, 7.37 g of the product of Step A and 147.4 ml of methanol was stirred at 20° C. for one hour and then 300 ml of diethyl oxide and 300 ml of aqueous 0.25M sodium bicarbonate solution were added thereto. The decanted aqueous phase was extracted with diethyl oxide and the organic phase was washed with aqueous saturated sodium chloride solution, dried and evaporated to dryness. The product was dissolved in a mixture of diisopropyl oxide and methylene chloride and the solution was concentrated and allowed to stand. The mixture was vacuum filtered and the crystals were dried to obtain 3.74 g of 11β-[4-(N,N-dimethylaminomethyl)-phenyl]-17α-(prop-1-ynyl)-Δ$^{4,9}$-estradiene-17β-ol-3-one melting at 190° C. and having a specific rotation of $[\alpha]_D^{20} = +84.5° \pm 2°$ (c=0.8% in chloroform).

EXAMPLE 39

11β-(4-pyrrolidinyl-phenyl)-17α-(prop-1-ynyl)-Δ$^{4,9}$-estradiene-17β-ol-3-one

STEP A: 3,3-[1,2-ethanediyl-bisoxy]-11β-(4-pyrrolidinyl-phenyl)-17α-(prop-1-ynyl)-Δ$^9$-estrene-5α,17β-diol A solution of 34 g of 4-pyrrolidinyl-bromobenzene in 140 ml of anhydrous tetrahydrofuran was added over one hour under an inert atmosphere at 45°–50° C. to a mixture of 4 g of magnesium and 10 ml of anhydrous tetrahydrofuran and the reaction was started by addition of dibromoethane to obtain a 1M magnesium solution. 86.4 ml of the said solution were added over 90 minutes at 0° to 5° C. under an inert atmosphere to a mixture of 8 g of 3,3-[1,2-ethanediyl-bisoxy]-5α,10α-epoxy-17α-(prop-1-ynyl)-Δ$^{9(11)}$-estrene-17β-ol in 160 ml of anhydrous tetrahydrofuran and 216 mg of copper chloride and the mixture was stirred for one hour and was poured into an aqueous saturated ammonium chloride solution. The mixture was extracted with diethyl oxide and the organic phase was washed with aqueous saturated ammonium chloride solution, aqueous saturated sodium chloride solution, dried and evaporated to dryness. The residue was chromatographed over silica gel and was eluted with a 95-5 methylene chloride-acetone mixture containing part per 1000 of triethylamine to obtain 8.3 g of 3,3-[1,2-ethanediyl-bisoxy]-11β-(4-pyrrolidinyl-phenyl)-17α-(prop-1-ynyl)-Δ$^9$-estrene-5α,17β-diol which after crystallization from a methylene chloride-isopropyl ether mixture melted at 185° C. and had a specific rotation of $[\alpha]_D^{20}=-67°\pm1.5°$ (c=1% in chloroform).

STEP B: 11β-(4-pyrrolidinyl-phenyl)-17α-(prop-1-ynyl)-Δ$^{4,9}$-estradiene-17β-ol-3-one A mixture of 13 ml of 2N hydrochloric acid, 6.4 g of the product of Step A and 128 ml of methanol was stirred at 20° C. for one hour and then 256 ml of diethyl oxide and 256 ml of aqueous 0.25M sodium bicarbondate solution were added thereto. The decanted aqueous phase was extracted with diethyl oxide and the organic phase was washed with aqueous 0.25M sodium bicarbonate solution, with aqueous saturated sodium chloride solution, dried and evaporated to dryness. The residue was chromatographed over silica gel and was eluted with a 1-1 petroleum ether-ethyl acetate mixture to obtain 5.25 g of 11β-(4-pyrrolidinyl-phenyl)-17α-(prop-1-ynyl)-Δ$^{4,9}$-estradiene-17β-ol-3-one which after crystallization from a methylene chloride-diisopropyl oxide mixture melted at 190° C. and had a specific rotation of $[\alpha]_D^{20}=+120°\pm2.5°$ (c=1.2% in chloroform).

EXAMPLE 40

11β-[4-(N,N-dimethylamino)-phenyl]-17α-ethenyl-Δ$^{4,9}$-estradiene-17β-ol-3-one STEP A: 3,3-[1,2-ethanediyl-bisoxy]-11β-[4-(N,N-dimethylamino)-phenyl]-17α-ethenyl-Δ$^9$-estrene-5α,17β-diol A current of hydrogen was passed for one hour through a mixture of 3 g of the product of Step B of Example 32, 60 ml of anhydrous pyridine and 0.6 g of 5% palladized calcium carbonate at room temperature and the mixture was then vacuum filtered. The filtrate was evaporated to dryness and the residue was taken up in toluene. The solution was evaporated to dryness to obtain 2.94 g of 3,3-[1,2-ethanediyl-bisoxy]-11β-[4-(N,N-dimethylamino)-phenyl]-17α-ethenyl-Δ$^9$-estrene-5α,17β-diol melting at 181° C. which was used as is for the next step. A sample after crystallization from a mixture of methylene chloride-diisopropyl oxide melted at 182° C. and had a specific rotation of $[\alpha]_D^{20}=-6.5°\pm2°$ (c=0.7% in chloroform).

STEP B: 11β-[4-(N,N-dimethylamino)-phenyl]-17α-ethenyl-Δ$^{4,9}$-estradiene-17β-ol-3-one A mixture of 6.2 ml of 2N hydrochloric acid, 2.94 g of the product of Step A and 60 ml of methanol was stirred at 20° C. for one hour and then 120 ml of ether and 120 ml of aqueous 0.25M sodium bicarbonate solution were added thereto. The mixture was stirred for 10 minutes and the decanted aqueous phase was extracted with ether. The organic phase was washed with aqueous 0.25M sodium bicarbonate solution, aqueous saturated sodium chloride solution, dried and evaporated to dryness. The 2.65 g of residue were chromatographed over silica gel and eluted with a 7-3 benzene-ethyl acetate mixture. The product was crystallized from a diisopropyl oxide-methylene chloride mixture to obtain 1.51 g of 11β-[4-(N,N-dimethylamino)-phenyl]-17α-ethenyl-Δ$^{4,9}$-estradiene-17β-ol-3-one melting at 150° C. and having a specific rotation of $[\alpha]_D^{20}=+243°\pm3°$ (c=0.8% in chloroform).

EXAMPLE 41

11β-[4-(N,N-diethylamino)-phenyl]-17α-(prop-1-ynyl)-Δ$^{4,9}$-estradiene-17β-ol-3-one STEP A: 4-(N,N-diethylamino)-bromobenzene 93 g of bromine were added dropwise to a solution of 86 g of N,N-diethylaniline in 400 ml of acetic acid and the mixture was poured into an ice-water mixture. The mixture was extracted with methylene chloride and the organic phase was washed with aqueous sodium bicarbonate solution, dried and evaporated to dryness to obtain 125 g of 4-(N,N-diethylamino)-bromobenzene boiling at 97° C. at 0.6 mm Hg.

STEP B: 3,3-[1,2-ethanediyl-bisoxy]-11β-[4-(N,N-diethylamino)-phenyl]-17α-(prop-1-ynyl)-Δ$^9$-estrene-5α,17β-diol A solution of 34.2 g of 4-(N,N-diethylamino)-bromobenzene in 110 ml of tetrahydrofuran was added at 35° C. under an inert atmosphere to a mixture of 3.9 g of magnesium and 10 ml of tetrahydrofuran to obtain a 1M magnesium solution and 80 ml of the said solution was slowly added with stirring at 0° to 5° C. under an inert atmosphere to a solution of 7.4 g of 3,3-[1,2-ethanediyl-bisoxy]-5α,10α-epoxy-17α-(prop-1-ynyl)-Δ$^{9(11)}$-estrene-17β-ol, 150 ml of anhydrous tetrahydrofuran and 0.25 g of copper chloride. The mixture was stirred at 20° C. for 17 hours and was then poured into an aqueous ammonium chloride solution. The mixture was extracted with ether and the organic phase was washed with aqueous sodium bicarbonate solution, dried and evaporated to dryness. The residue was empasted with petroleum ether and treated with activated carbon in ether. The product was crystallized from isopropyl ether to obtain 4 g of 3,3-[1,2-ethanediyl-bisoxy]-11β-[4-(N,N-diethylamino)-phenyl]-17α-(prop-1-ynyl)-Δ$^9$-estrene-5α,17β-diol with a specific rotation of $[\alpha]_D^{20}=-61°\pm2.5°$ (c=0.7% in CHCl$_3$).

STEP C: 11β-[4-(N,N-diethylamino)-phenyl]-17α-(prop-1-ynyl)-Δ$^{4,9}$-estradiene-17β-ol-3-one A mixture of 8 ml of 2N hydrochloric acid, 3.12 g of the product of Step B and 45 ml of methanol was stirred at 20° C. under an inert atmosphere for 45 minutes and was then poured into water. The mixture was neutralized by addition of 2N sodium hydroxide solution and was extracted with methylene chloride. The organic phase was dried and evaporated to dryness and the residue was chromatographed over silica gel. Elution with a 1-1 benzene-ethyl acetate mixture yielded 1.34 g of 11β-[4-(N,N-diethylamino)-phenyl]-17α-(prop-1-yny)-Δ$^{4,9}$-estradiene-17β-ol-3-one with a specific rotation of $[\alpha]_D^{20}=+144.5°\pm3°$ (c=0.8% in chloroform).

| Analysis: $C_{31}H_{39}NO_2$; molecular weight = 457.63 | | | |
|---|---|---|---|
| | % C | % H | % N |
| Calculated: | 81.36 | 8.59 | 3.06 |
| Found: | 81.7 | 8.8 | 2.09 |

EXAMPLE 42

11$\beta$-[4-(N-methyl-N-3-methylbutylamino)-phenyl]-17$\alpha$-(prop-1-ynyl)-$\Delta^{4,9}$-estradiene-17$\beta$-ol-3-one STEP A: N-methyl-N-(3-methylbutyl)-aniline 121 g of isoamyl bromide were added dropwise to a mixture of 86 g of N-methyl-aniline, 500 ml of anhydrous benzene and 81 g of anhydrous triethylamine and the mixture was refluxed for 100 hours and was filtered. The filtrate was washed with water, dried and evaporated to dryness. The residue was distilled to obtain 90 g of N-methyl-N-(3-methylbutyl)-aniline boiling at 132° C. at 18 mm Hg.

STEP B: N-methyl-N-(3-methylbutyl)-4-bromo-aniline

A solution of 58 g of bromine in 60 ml of acetic acid was added dropwise at about 15° C. over one hour to a mixture of 64 g of the product of Step A in 300 ml of acetic acid and the mixture was stirred at 80° C. for 8 hours and was poured into iced water. The mixture was extracted with methylene chloride and the organic phase was washed with aqueous sodium bicarbonate, with water, dried and evaporated to dryness. The residue was distilled to obtain 70 g of N-methyl-N-(3-methylbutyl)-4-bromo-aniline boiling at 119° C. at 0.5 mm Hg.

STEP C: 3,3-[1,2-ethanediyl-bisoxy]-11$\beta$-[4-(N-methyl-N-3-methylbutylamino)-phenyl]-17$\alpha$-(prop-1-ynyl)-$\Delta^9$-estrene-5$\alpha$,17$\beta$-diol A few ml of a solution of the product of Step B in tetrahydrofuran were added under an inert atmosphere to a mixture of 4.12 g of magnesium and 10 ml of tetrahydrofuran and the reaction was started by addition of 0.2 ml of 1,2-dibromoethane. The rest of the solution of the product of Step B in anhydrous tetrahydrofuran (32.6 g in 90 ml) was added over 40 minutes to the mixture and after the temperature returned to room temperature, the mixture was stirred for one hour to obtain an 0.9M magnesium solution. A mixture of 3.77 g of copper chloride, 8 g of 3,3-[1,2-ethanediyl-bisoxy]-5$\alpha$,10$\alpha$-epoxy-17$\alpha$-(prop-1-ynyl)-$\Delta^{9(11)}$-estrene-17$\beta$-ol and 90 ml anhydrous tetrahydrofuran was stirred under an inert atmosphere at 5° C. for 20 minutes and then 100 ml of the magnesium solution were added thereto. The mixture was poured into aqueous ammonium chloride solution and was extracted with ether containing triethylamine and then with methylene chloride containing triethylamine. The combined organic phases were washed with aqueous saturated sodium chloride solution, dried and evaporated to dryness to obtain 31.2 g of 3,3-[1,2-ethanediyl-bisoxy]-11$\beta$-[4-(N-methyl-N-3-methylbutylamino)-phenyl]-17$\alpha$-(prop-1-ynyl)-$\Delta^9$-estrene-5$\alpha$,17$\beta$-diol which was used as is for the next step. A sample of the product was chromatographed over silica gel and was eluted with a 96.5-4.5-0.5 methylene chloride-acetone-triethylamine mixture to obtain the compound with a specific rotation of $[\alpha]_D^{20}= -59.5°\pm2.5°$ (c=0.7% in chloroform).

STEP D: 11$\beta$-[4-(N-methyl-N-(3-methyl-butyl)-amino)-phenyl]-17$\alpha$-(prop-1-ynyl)-$\Delta^{4,9}$-estradiene-17$\beta$-ol-3-one A mixture of 52 ml of 2N hydrochloric acid, 26 g of the product of Step C and 200 ml of methanol was stirred for one hour and was then poured into aqueous sodium bicarbonate. The mixture was extracted with ether and then methylene chloride and the combined organic phases were washed with aqueous saturated sodium chloride solution, dried and evaporated to dryness. The residue was chromatographed over silica gel and was eluted with an 92-8 toluene-ethyl acetate mixture to obtain 3.23 g of 11$\beta$-[4-(N-methyl-N-(3-methylbutyl)-amino)-phenyl]-17$\alpha$-(prop-1-ynyl)-$\Delta^{4,9}$-estradiene-17$\beta$-ol-3-one with a specific rotation of $[\alpha]_D^{20}= +125°\pm3.5°$ (c=0.6% in chloroform).

| Analysis: $C_{33}H_{43}NO_2$; molecular weight = 485.71 | | | |
|---|---|---|---|
| | % C | % H | % N |
| Calculated: | 81.6 | 8.92 | 2.88 |
| Found: | 81.4 | 9.0 | 2.7 |

EXAMPLE 43

11$\beta$-[4-(N,N-dimethylaminoethylthio)-phenyl]-17$\alpha$-(prop-1-ynyl)-$\Delta^{4,9}$-estradiene-17$\beta$-ol-3-one STEP A: 4-(N,N-dimethylaminoethylthio)-bromobenzene A solution of 23.5 g of chloroethyldimethylamine.HCl in 75 ml of ethanol was added to 160 ml of sodium hydroxide solution formed by dissolving 20 g of sodium hydroxide pastilles in 500 ml of ethanol. A solution of 30 g of 4-bromothiophenol in 100 ml of ethanol was added to 160 ml of the said sodium hydroxide solution and the first solution was added thereto over 2 minutes at 20° C. The mixture was refluxed for 3 hours and was evaporated to dryness. Water was added to the residue and the mixture was extracted with methylene chloride. The organic phase was washed with aqueous 0.1N sodium hydroxide solution, then with water, dried and evaporated to dryness. The residue was distilled to obtain 35.5 g of 4-(N,N-dimethylaminoethylthio)-bromobenzene boiling at 110° C. at 0.1 mm Hg.

STEP B: 3,3-[1,2-ethanediyl-bisoxy]-11$\beta$-[4-(N,N-dimethylaminoethylthio)-phenyl]-17$\alpha$-(prop-1-ynyl)-$\Delta^9$-estrene-5$\alpha$,17$\beta$-diol A solution of 20 g of the product of Step A in 40 ml of anhydrous tetrahydrofuran was added over 45 minutes under an inert atmosphere to a mixture of 2 g of magnesium and 15 ml of tetrahydrofuran while the temperature rose to 56° C. and the reaction was started by addition of 1,2-dibromoethane. The mixture was returned to 20° C. and was stirred at 20° C. for 45 minutes under an inert atmosphere to obtain a 1.05M magnesium solution.

1.730 g of copper chloride were added with stirring at −20° C. under an inert atmosphere to 38 ml of the said magnesium solution and the mixture was stirred for 20 minutes. A solution of 5 g of 3,3-[1,2-ethanediyl-bisoxy]-5$\alpha$,10$\alpha$-epoxy-17$\alpha$-(prop-1-ynyl)-$\Delta^{9(11)}$-estrene-17$\beta$-ol in 50 ml of anhydrous tetrahydrofuran was added to the mixture which was then stirred for 24 hours under an inert atmosphere at 20° C. and was then poured into 600 ml of iced water containing 60 g of ammonium chloride. The decanted aqueous phase was extracted with diethyl oxide containing triethylamine and the combined organic phase was washed with aqueous saturated sodium chloride solution, dried and evaporated to dryness. The residue was chromatographed over silica gel and was eluted with a 95-5 methylene chloride-acetone mixture to obtain 10.3 g of 3,3-[1,2-ethanediyl-bisoxy]-11β-[4-(N,N-dimethylaminoethylthio)-phenyl]-17α-(prop-1-ynyl)-Δ$^9$-estrene-5α,17β-diol.

IR Spectrum: Absorption at 3600 cm$^{-1}$(OH); at 2240 cm$^{-1}$ (C≡C); at 1705 and 1670 cm$^{-1}$ (CO and conjugated CO); at 1615 and 1490 cm$^{-1}$ (aromatic bands).

STEP C: 11β-[4-(N,N-dimethylaminoethylthio)-phenyl]-17α-(prop-1-ynyl)-Δ$^{4,9}$-estradiene-17β-ol-3-one A mixture of 20.6 ml of 2N hydrochloric acid, 10.3 g of the product of Step B and 72 ml of methanol was stirred at 20° C. under an inert atmosphere for 25 minutes and was neutralized by addition of aqueous saturated sodium bicarbonate solution. 200 ml of diethyl oxide were added to the mixture and the decanted aqueous phase was extracted with diethyl oxide. The combined organic phases were washed with aqueous saturated sodium chloride solution, dried and evaporated to dryness and the residue was chromatographed over silica gel. Elution with a 9-1 methylene chloride-methanol mixture yielded 3 g of 11β-[4-(N,N-dimethylaminoethylthio)-phenyl]-17α-(prop-1-ynyl)-Δ$^{4,9}$-estradiene-17β-ol-3-one which after crystallization by empasting with diisopropyl oxide melted at 145° C. and had a specific rotation of [α]$_D^{20}$= +125°±2° (c=1% in chloroform).

EXAMPLE 44

11β-[4-(N,N-dimethylamino)-phenyl]-21-trimethylsilyl-19-nor-17α-Δ$^{4,9}$-pregnadiene-20-yne-17β-ol-3-one STEP A: 3,3-[1,2-ethanediyl-bisoxy]-11β-[4-(N,N-dimethylamino)-phenyl]-21-trimethylsilyl-19-nor-17α-Δ$^9$-pregnene-20-yne-5α,17β-diol A mixture of 13 ml of a 1.6M ethyl magnesium bromide in tetrahydrofuran and 13 ml of anhydrous tetrahydrofuran was stirred for 5 minutes at 0° to 5° C. and 3.4 ml of trimethylsilyl acetylene were added thereto dropwise. The temperature was allowed to rise to 20° C. and the mixture was then stirred for 20 minutes. Then, a solution of 1.12 g of the product of Step B of Example 22 in 10 ml of anhydrous tetrahydrofuran was added dropwise to the mixture and the mixture was stirred at room temperature for 16 hours and was poured into aqueous ammonium chloride solution. The mixture was stirred at room temperature for 10 minutes and was extracted with methylene chloride. The organic phase was washed with aqueous saturated sodium chloride solution, was dried and evaporated to dryness. The residue was chromatographed over silica gel and was eluted with a 6-4 petroleum ether-ethyl acetate mixture to obtain 680 mg of 3,3-[1,2-ethanediyl-bisoxy]-11β-[4-(N,N-dimethylamino)-phenyl]-21-trimethylsilyl-19-nor-17α-Δ$^9$-pregnene-20-yne-5α,17β-diol with a specific rotation of [α]$_D^{20}$= −76.5°±3° (c=0.5% in chloroform).

STEP B: 11β-[4-(N,N-dimethylamino)-phenyl]-21-trimethylsilyl-19-nor-17α-Δ$^{4,9}$-pregnadiene-20-yne-17β-ol-3-one A mixture of 1 ml of 2N hydrochloric acid, 562 mg of the product of Step A and 15 ml of methanol was stirred at room temperature for 40 minutes and was poured into aqueous sodium bicarbonate solution. The mixture was extracted with ether and the organic phase was washed with aqueous saturated sodium chloride solution. was dried and evaporated to dryness. The residue was chromatographed over silica gel and was eluted with a 6-4 petroleum ether-ethyl acetate mixture to obtain 364 mg of 11β-[4-(N,N-dimethylamino)-phenyl]-21-trimethylsilyl-19-nor-17α-Δ$^{4,9}$-pregnadiene-20-yne-17β-ol-3-one with a specific rotation of [α]$_D^{20}$= +97.5°±3° (c=0.35% in CHCl$_3$).

| Analysis: C$_{31}$H$_{41}$NO$_2$Si; molecular weight = 487.76 | | | |
|---|---|---|---|
| | % C | % H | % N |
| Calculated: | 76.33 | 8.47 | 2.87 |
| Found: | 76.4 | 8.7 | 2.8 |

EXAMPLE 45

N-oxide of 11β-[4-(N,N-dimethylaminomethyl)-phenyl]-17α-(prop-1-ynyl)-Δ$^{4,9}$-estradiene-17β-ol-3-one A solution of 0.64 g of m-chloroperbenzoic acid in 12.8 ml of methylene chloride was added over 15 minutes at 0° to 5° C. to a solution of 1.4 g of the product of Example 38 in 28 ml of methylene chloride and the mixture was stirred at 0° to 5° C. for one hour and was then poured into aqueous 0.2N sodium thiosulfate solution. The decanted aqueous phase was extracted with methylene chloride and the organic phase was washed with aqueous sodium bicarbonate solution. dried and evaporated to dryness. The residue was chromatographed over silica gel and was eluted with an 8-2 mixture to obtain 1.28 g of N-oxide of 11β-[4-(N,N-dimethylaminomethyl)-phenyl]-17α-(prop-1-ynyl)-Δ$^{4,9}$-estradiene-17β-ol-3-one. The product was dissolved in a mixture of methylene chloride and diisopropyl oxide and the mixture was vacuum filtered to obtain 1.075 g of the said product melting at 215° C. and having a specific rotation of [α]$_D^{20}$= +74.5°±2.5° (c=0.7% in CHCl$_3$).

EXAMPLE 46

Hemifumarate of 11β-[4-(N,N-dimethylaminomethyl)-phenyl]-17α-(prop-1-ynyl)-Δ$^{4,9}$-estradiene-17β-ol-3-one A mixture of 0.378 g of fumaric acid in 4.54 ml of ethanol was added to a mixture of 1.44 g of the product of Example 38 in 2.88 ml of ethanol and the mixture was stirred at 60° C. for 30 minutes. The mixture returned to 20° C. and was stirred. The mixture was evaporated to dryness and the residue was taken up in ether. The mixture was vacuum filtered and the product was dried to obtain 1.70 g of hemifumarate of 11β-[4-(N,N-dimethylaminomethyl)-phenyl]-17α-(prop-1-ynyl)-Δ$^{4,9}$-estradiene-17β-ol-3-one melting at 160° C. and having a specific rotation of [α]$_D^{20}$= +70.5°±2.5° (c=0.8% in CHCl$_3$).

EXAMPLE 47

11β-[4-(N,N-dipropylamino)-phenyl]-17α-(prop-1-ynyl)-Δ$^{4,9}$-estradiene-17β-ol-3-one STEP A: 3,3-[1,2-ethanediyl-bisoxy]-11β-[4-(N,N-dipropylamino)-phenyl]-17α-(prop-1-ynyl)-Δ$^9$-estrene-5α,17β-diol A solution of 52 g of 4-bromo-N,N-dipropyl-aniline in 110 ml of tetrahydrofuran was added dropwise at 40° C. under an inert atmosphere to a mixture of 5 g of magnesium and 15 ml of anhydrous tetrahydrofuran to obtain a 1.1M magnesium solution. A solution of 5.55 g of 3,3-[1,2-ethanediyl-bisoxy]-5α,10α-epoxy-17α-(prop-1-ynyl)-Δ$^{9(11)}$-estrene-17β-ol and 200 mg of cuprous chloride was stirred at 0° to 5° C. and then 50 ml of the magnesium solution were added thereto over 15 minutes. The mixture was stirred at 20° C. for one hour and was then poured into aqueous saturated ammonium chloride solution. The mixture was extracted with ether and the organic phase was dried and evaporated to dryness. The residue was chromatographed over silica gel and was eluted with a 7-3 toluene-ethyl acetate mixture to obtain 6.3 g of 3,3-[1,2-ethanediyl-bisoxy]-11β-[4-(N,N-dipropylamino)-17α-(prop-1-ynyl)-Δ$^9$-estrene-5α,17β-diol with a specific rotation of $[α]_D^{20} = -56° ± 2°$ (c=0.8% in CHCl$_3$).

| Analysis: C$_{35}$H$_{49}$NO$_4$; molecular weight = 547.75 | | | |
|---|---|---|---|
| | % C | % H | % N |
| Calculated: | 76.74 | 9.02 | 2.56 |
| Found: | 76.6 | 9.2 | 2.5 |

STEP B: 11β-[4-(N,N-dipropylamino)-phenyl]-17α-(prop-1-ynyl)-Δ$^{4,9}$-estradiene-17β-ol-3-one A mixture of 10 ml of 2N hydrochloric acid, 5,83 g of the product of Step A and 80 ml of methanol was stirred at 20° C. for 50 minutes and was then neutralized by addition of N sodium hydroxide solution. The mixture was evaporated to dryness under reduced pressure and the residue was taken up in methylene chloride. The organic phase was washed with water, dried and evaporated to dryness and the residue was chromatographed over silica gel. Elution with a 3-1 toluene-ethyl acetate mixture yielded 3.81 g of 11β-[4-(N,N-dipropylamino)-phenyl/-17α-(prop-1-ynyl)-Δ$^{4,9}$-estradiene-17β-ol-3-one.

IR Spectrum: Absorption at 3600 cm$^{-1}$ (OH); at 1654 cm$^{-1}$ (C=O); at 1610-1595-1558 and 1517 cm$^{-1}$ (Δ$^{4,9}$ and aromatic bands); at 2240 cm$^{-1}$ (C≡C).

The following products were prepared by the process of the invention using the appropriate starting materials:

(A) 11β-[4-(N-ethyl-N-methylamino)-phenyl]-17α-(prop-1-ynyl)-Δ$^{4,9}$-estradiene-17β-ol-3-one melting at 174° C. and having a specific rotation of $[α]_D^{20} = +149° ± 2.5°$ (c=1% in CHCl$_3$).

(B) 11β-[N-methyl-2,3-dihydro-1H-indol-5-yl]-17α-(prop-1-ynyl)-Δ$^{4,9}$-estradiene-17β-ol-3-one melting at 176° C. and having a specific rotation of $[α]_D^{20} = +133° ± 3°$ (c=0.8% in CHCl$_3$).

(C) 3-hydroxyimino-11β-[4-(N,N-dimethylamino)-phenyl]-17α-(prop-1-ynyl)-Δ$^{4,9}$-estradiene-17β-ol (Z isomer) melting at 260° C. and having a specific rotation of $[α]_D^{20} = +141° ± 3.5°$ (c=0.8% in CHCl$_3$) and the corresponding E isomer melting at 220° C. and having a specific rotation of $[α]_D^{20} = +164° ± 3.5°$ (c=0.8% in CHCl$_3$).

(D) N-oxide of 11β-[4-pyrrolidyl-phenyl]-17α-(prop-1-ynyl)-Δ$^{4,9}$-estradiene-17β-ol-3-one melting at 220° C. and having a specific rotation of $[α]_D^{20} = +88° ± 2.5°$ (c=0.75% in CHCl$_3$)

(E) 11β-[4-(N-methyl-N-isopropylamino)-phenyl]-17α (prop-1-ynyl)-Δ$^{4,9}$-estradiene-17β-ol-3-one with a specific rotation of $[α]_D^{20} = +140° ± 3.5°$ (c=0.5% in CHCl$_3$).

(F) N-oxide of 11β-[4-(N,N-dimethylaminoethoxy)-phenyl]-17α-(prop-1-ynyl)-Δ$^{4,9}$-estradiene-17β-ol-3-one with a specific rotation of $[α]_D^{20} = +60.5°$ (c=1.2% in CHCl$_3$).

(G) N-oxide of 11β-[(N-methyl)-2,3-dihydro-1H-indol-5-yl]-17α-(prop-1-ynyl)-Δ$^{4,9}$-estradiene-17β-ol-3-one with a specific rotation of $[α]_D^{20} = -103° ± 2.5°$ (c=0.8% in CHCl$_3$).

(H) 11β-[4-(N-methyl-N-trimethylsilylmethylamino)-phenyl]-17α-(prop-1-ynyl)-Δ$^{4,9}$-estradiene-17β-ol-3-one.

(I) 11β-[4-(N-methyl-N-dimethylaminoethylamino)-phenyl]-17α-(prop-1-ynyl)-Δ$^{4,9}$-estradiene-17β-ol-3-one.

(J) 11β-[4-(N-methyl-piperazin-1-yl)-phenyl]-17α-(prop-1-ynyl)-Δ$^{4,9}$-estradiene-17β-ol-3-one.

(K) 11β-[4-(N,N-dimethylamino)-phenyl]-17-hydroxyimino-Δ$^{4,9}$-estradiene-3-one with a specific rotation of $[α]_D^{20} = +207.5° ± 3.5°$ (c=1% in CHCl$_3$).

(L) 3(E)-hydroxyimino-11β-[4-(N,N-dimethylamino)-phenyl]-17-hydroxyimino-Δ$^{4,9}$-estradiene-3-one with a specific rotation of $[α]_D^{20} = +195° ± 3°$ (c=1% in CHCl$_3$) and its corresponding 3(Z) isomer with a specific rotation of $[α]_D^{20} = +163° ± 2.5°$ (c=0.6% in CHCl$_3$).

EXAMPLE 48

γ-lactone of 11β-(4-dimethylamino-phenyl)-19-nor-17α-Δ$^{4,9}$-pregnadiene-17β-ol-3-one-21-carboxylic acid STEP A: γ-lactone of 3,3-ethylenedioxy-11β-(4-dimethylamino-phenyl)-19-nor-17α-Δ$^{9(10)}$-pregnene-5α,17β-diol-21-carboxylic acid 60 ml of a solution of 15% butyllithium in hexane cooled to −70° C. were diluted with 60 ml of tetrahydrofuran and a solution of 9.2 ml of allyl N,N,N',N'-tetramethyl-phosphoramidate in 30 ml of anhydrous tetrahydrofuran was added thereto at −60° C. The mixture was held at −15° to −10° C. for 45 minutes and then a solution of 9.95 g of 3,3-ethylenedioxy-11β-(4-N,N-dimethylamino-phenyl)-Δ$^9$-estrene-5α-ol-17-one (described in Step B of Example 22 in 20 ml of anhydrous tetrahydrofuran was added thereto. The mixture was rinsed with 5 ml of anhydrous tetrahydrofuran and 20 ml of tetrahydrofuran were added with stirring. The temperature returned to room temperature over one hour and the mixture was poured into an aqueous ammonium chloride solution. The mixture was extracted with ethyl acetate and the organic phase was washed with water, dried and evaporated to dryness under reduced pressure to obtain 12.95 g of residue which contained starting material. The residue was chromatographed over silica gel and was eluted with a 3-7 cyclohexane-ethyl acetate mixture to separately obtain 5 g of starting material, 0.27 g of a mixture and 3.9 g of γ-lactone of 3,3-ethylenedioxy-11β-(4-dimethylamino-phenyl)-19-nor-17α-Δ$^{9(10)}$-pregnene-5α,17β-diol-21-carboxylic acid. 5.5 g of the latter were dissolved in methylene chloride and the solution was filtered. The filtrate was diluted with isopropyl ether and the solution was concentrated by evaporation of methylene chloride to obtain a suspension of crystals in isopropyl ether from which 4.87 g of the product melting at 198° C. were recovered.

| Analysis: C$_{31}$H$_{41}$O$_5$N; molecular weight = 507.67 | | | |
|---|---|---|---|
| | % C | % H | % N |
| Calculated: | 73.34 | 8.14 | 2.76 |
| Found: | 73.1 | 8.3 | 2.8 |

STEP B: γ-lactone of 11β-(4-dimethylamino-phenyl)-19-nor-17α-Δ$^{4,9}$-pregnadiene-17β-ol-3-one-21-carboxylic acid A solution of 4.7 g of the product of Step A in 40 ml of methanol and 10 ml of 2N hydrochloric acid stood for one hour at room temperature and was then diluted with water and was extracted with methylene chloride. The organic phase was washed with water, dried and evaporated to dryness under reduced pressure. The 4.5 g of residue were chromatographed over silica gel and eluted with a 4-6 cyclohexane-ethyl acetate mixture to obtain 3.85 g of non-crystalline γ-lactone of 11β-(4-dimethylamino-phenyl)-19-nor-17α-Δ$^{4,9}$-pregnadiene-17β-ol-3-one-21-carboxylic acid with a specific rotation of $[\alpha]_D^{20} = +172°$ (c=1% in chloroform).

| Analysis: $C_{29}H_{35}NO_3$; molecular weight = 445.61 | | | |
|---|---|---|---|
| | % C | % H | % N |
| Calculated: | 78.17 | 7.91 | 3.14 |
| Found: | 78.5 | 8.1 | 3.0 |

EXAMPLE 49

γ-lactone of 11β-(4-dimethylamino-phenyl)-19-nor-17α-Δ$^{1,3,5(10)}$-pregnatriene-3,17β-diol-21-carboxylic acid 1.5 g of palladium hydroxide on magnesium were added to a solution of 1 g of the product of Example 48 in 300 ml of methanol and the mixture was stirred at reflux for one hour and was then cooled and filtered. The filtrate was evaporated to dryness to obtain 1 g of a colored product. The latter was chromatographed over silica gel and eluted with a 1-1 cyclohexane-ethyl acetate mixture and the 980 mg of product were crystallized from ether. The suspension was vacuum filtered to obtain 715 mg of γ-lactone of 11β-(4-dimethylamino-phenyl)-19-nor-17α-Δ$^{1,3,5(10)}$-pregnatriene-3,17β-diol-21-carboxylic acid which melted at 311° C. after crystallization from ethyl acetate.

| Analysis: $C_{29}H_{35}NO_3$; molecular weight = 445.6 | | | |
|---|---|---|---|
| | % C | % H | % N |
| Calculated: | 78.15 | 7.91 | 3.14 |
| Found: | 78.4 | 8.0 | 3.0 |

EXAMPLE 50

γ-lactone of 3-methoxy-11β-(4-dimethylamino-phenyl)-19-nor-17α-Δ$^{1,3,5(10)}$-pregnatriene-17β-ol-21-carboxylic acid A solution of diazomethane [prepared by Can. J. Res., Vol. 28 (1950), 683] in methylene chloride was added to a solution of 280 mg of the product of Example 49 in 3 ml of methylene chloride and the diazomethane was added again. After 20 hours, acetic acid was added to destroy excess diazomethane and the mixture was made alkaline by addition of aqueous sodium bicarbonate. The decanted organic phase was washed with water, dried and evaporated to dryness under reduced pressure to obtain 295 mg of a mixture containing starting material. The latter was chromatographed over silica gel and eluted with a 7-3 and then 1-1 cyclohexane-ethyl acetate mixture to obtain 120 mg of γ-lactone of 3-methoxy-11β-(4-dimethylamino-phenyl)-19-nor-17α-Δ$^{1,3,5(10)}$-pregnatriene-17β-ol-21-carboxylic acid and then 140 mg of starting material. The former product was dissolved in methylene chloride and the solution was filtered. The filtrate was evaporated to dryness and the product was crystallized from ether, vacuum filtered and washed with ether to obtain 66 mg of desired product melting at 210° C.

| Analysis: $C_{30}H_{35}NO_3$; molecular weight = 459.63 | | | |
|---|---|---|---|
| | % C | % H | % N |
| Calculated: | 78.39 | 8.11 | 3.04 |
| Found: | 78.2 | 8.4 | 3.0 |

EXAMPLE 51

γ-lactone of 11β-(4-dimethylamino-phenyl)-19-nor-17α-Δ$^{5(10)}$-pregnene-17β-ol-3-one-21-carboxylic acid 1 ml of a 1.3M lithium tert.-butanolate in tetrahydrofuran and 1 ml of water were added to a solution of 690 mg of the γ-lactone of 11β-(4-dimethylamino-phenyl)-19-nor-α-Δ$^{4,9(10)}$-pregnadiene-17β-ol-3-one-21-carboxylic acid in 10 ml of absolute ethanol and the mixture was refluxed under nitrogen for 30 minutes. The mixture was evaporated to dryness under reduced pressure and the residue was taken up in benzene. The solution was distilled to dryness and the lithium salt was dissolved in a mixture of 9 ml of tetrahydrofuran and 1 ml of tert.-butanol. The said solution was added to 30 ml of ammonia cooled to −70° C. and the solution was rinsed with 3 ml of anhydrous tetrahydrofuran. 24 mg of lithium were added to the solution while maintaining an internal temperature of −50° to −60° C. The ammonia was distilled and the mixture was acidified with hydrochloric acid. The resulting solution stood at room temperature for 30 minutes and was made alkaline by addition of a sodium bicarbonate solution. The mixture was extracted with methylene chloride and the organic phase was washed with water, dried and evaporated to dryness to obtain 680 mg of residue. The latter was chromatographed over silica gel and eluted with a 7 to 3 and then 1 to 1 mixture of cyclohexane-ethyl acetate to obtain 505 mg of non-crystalline γ-lactone of 11β-(4-dimethylamino-phenyl)-19-nor-17α-Δ$^{5(10)}$-pregnene-17β-ol-3-one-21-carboxylic acid.

NMR Spectra (CDCl$_3$): Peaks at 0.53 (13-methyl); at 2.9 (methyls of dimethylamino); at 3.51 (11-hydrogen)

| Analysis: $C_{29}H_{37}NO_3$ | | | |
|---|---|---|---|
| | % C | % H | % N |
| Calculated: | 77.81 | 8.33 | 3.13 |
| Found: | 77.5 | 8.6 | 3.0 |

EXAMPLE 52

Tablets were prepared containing 50 mg of the product of Example 19 and sufficient excipient of talc, starch and magnesium stearate for a final tablet weight of 120 mg.

EXAMPLE 53

Tablets were prepared containing 50 mg of the product of Example 5 and sufficient excipient of talc, starch and magnesium stearate for a final weight of 120 mg.

PHARMACOLOGICAL STUDY

I. Activity of products on hormonal receptors

A. Mineralcorticoidal receptor of kidneys of the rat

Male Sprague-Dawley EOPS rats weighing 140 to 160 g surrenalectomized 4 to 8 days previously were killed and their kidneys were perfused in situ with 50 ml of a buffer (10 mM of Tris 0.25M of Saccharose and sufficient hydrochloric acid for a pH of 7.4). The kidneys were then removed, decapsulated and homogenized at 0° C. with a polytetrafluoroethylene-glass Potter (1 g of tissue per 3 ml of buffer). The homogenate was centrifuged for 10 minutes at 800 g at 9° C.

After elimination of the fixation of tritiated aldosterone with glucocorticoid receptor, 21-methyl-$\Delta^{1,4,6}$-pregnatriene-20-yne-11$\beta$,17$\beta$-diol-3-one fixed only with the glucocorticoid receptor was added to the supernatant at a final concentration of $10^{-6}$M. The supernatant was ultracentrifuged at 105,000 g for 60 minutes and 0° C. and aliquoits of the resulting surnageant were incubated at 0° C. with a constant concentration (T) of tritiated aldosterone in the presence of increasing concentrations (0–2500$\times 10^{-9}$M) of cold aldosterone or the cold test product. After a time (t) of incubation, the concentration of tied tritiated aldosterone (B) was measured by the technique of adsoprtion on carbon dextran.

B. Androgen receptor of prostate of rats

Male Sprague-Dawley EPOS rats weighing of 160 to 200 g were castrated and 24 hours later, the animals were killed. The prostates were removed, weighed and homogenized at 0° C. with a polytetrafluoroethylene-glass Potter with a buffered TS solution (Tris, 10 mM, 0.25M Saccharose, HCl-pH of 7.4) using 1 g of tissue per 5 ml of TS. The homogenate was then ultracentrifuged at 105,000 g for 60 minutes at 0° C. and aliquoits of the resulting supernatant were incubated at 0° C. for 2 hours with a constant concentration (T) of product P or 17$\alpha$-methyl-$\Delta^{4,9,11}$-estratriene-17$\beta$-ol-3-one in the presence of increasing concentration (0–1,000$\times 10^{-9}$M) of either cold P, cold testosterone or the test compound. The concentration of tied tritiated (B) was measured for each incubate by the technique of adsorption on carbon-dextran.

C. Progestogen receptor of the uterus of rabbits

Immature rabbits weighing about 1 kg received a cutaneous application of 25 μg of estradiol and the animals were killed 5 days later. The uterus was removed, weighed and homogenized at 0° C. with a polytetrafluoroethylene-glass Potter, in a buffered TS solution [Tris 10. mM, 0.25M of saccharose, HCl-pH of 7.4] with 1 g of tissue per 50 ml of TS. The homogenate was ultracentrifuged at 105,000 g for 90 minutes at 0° C. and aliquoits of the resulting supernatant were incubated at 0° C. for a time (t) with a constant concentration (T) of tritiated product R or 17,21-dimethyl-19-nor-$\Delta^{4,9}$-pregnadiene-3,20-dione in the presence of increasing concentrations (0 to 2500$\times 10^{-9}$M) of either cold R, cold progesterone or cold test compound. The concentration of tied tritiated R (B) was then measured for each incubate by the technique of adsoprtion on carbon-dextran.

D. Gluocorticoid receptor of thymus of rats

Male Sprague-Dawley EPOS rats weighing 160 to 200 g were surrenalectomized and the animals were killed 4 to 8 days later. The thymus were removed and homogenized at 0° C. in a buffered TS solution of 10 mM, Tris, 0.25M of Saccharose, 2 mM of dithiothreitol HCl for a pH of 7.4 using a polytetrafluoroethylene-glass Potter at a rate of 1 g of tissue per 10 ml of TS. The homogenate was ultracentrifuged at 105.000 g for 90 minutes at 0° C. and aliquoits of the resulting surnageant were incubated at 0° C. for a time (t) with a constant concentration (T) of tritiated dexamethasone in the presence of an increasing concentration (0 to 2500$\times 10^{-9}$M) of either cold dexamethasone or cold test product. The concentration of tied tritiated dexamethasone (B) was measured for each incubate by the adsorption on carbon-dextran technique.

E. Estrogen receptor of uterus of mice

Immature female mice 18 to 21 days old were killed and the uterus were removed and homogenized at 0° C. with a polytetrafluoroethylene-glass Potter in a buffered TS solution consisting of 10 mM, Tris, 0125M Saccharose, HCl for a pH of 7.4 at a rate of 1 g of tissue per 25 ml of TS. The homogenate was then ultracentrigued at 105,000 g for 90 minutes at 0° C. and aliquoits of the resulting tritiated were incubated at 0° C. for a time (t) with a constant concentration (T) of tritiated estradiol in the presence of increasing concentrations (0 to 1000$\times 10^{-9}$M) of either cold estradiol or cold test compound. The concentration of tied tritiated estradiol (B) was measured for each incubate by the technique of adsorption on carbon-dextran.

The calculation of the relative affinity of concentration (ARL) was identical for all of the above receptor tests. One traced the following two curves: the percentage of tied tritiated hormone B/T as a function of the logarithm of the cold hormone concentration and B/T as a function of the logarithm of the concentration of the cold test product. One determined the line of the equation.

$$I_{50} = \frac{\frac{B}{T}\max. - \frac{B}{T}\min.}{2}$$

B/T max. is the percentage of tied tritiated hormone for an incubation of the hormone at concentration T B/T min. is the percentage of tied tritiated hormone for an incubation of the tritiated hormone at a concentration (T) in the presence of a large excess of cold hormone (2500$\times 10^{-9}$M).

The intersection of the $I_{50}$ line and the curves permits one to determine the concentrations of the cold hormone of the reference (CH) and the cold test compound (CX) which inhibit by 50% the tieing of tritiated hormone with the receptor. The relative affinity of tieing (ARL) of the test product was determined by the equation:

$$ARL = 100 \cdot \frac{CH}{CX}$$

The results are reported in the following Table.

| Product of Example | Mineralo corticoid 1 H | Mineralo corticoid 24 H | Androgen ½H | Androgen 24 H | Progestogen 2 H | Progestogen 24 H | Glucocorticoid 4 H | Glucocorticoid 24 H | Estrogen 2 H | Estrogen 5 H (25° C.) |
|---|---|---|---|---|---|---|---|---|---|---|
| 1 | <0.1 | <0.1 | — | — | 4 | 4 | 97 | 38 | <0.1 | <0.1 |
| 2 (17 OH) | 0.2 | <0.1 | * | * | 39 | 130 | 153 | 222 | 5 | <0.1 |
| 2 (17 OAc) | <0.1 | <0.1 | <0.1 | <0.1 | 5 | 52 | 58 | 100 | <0.1 | 0.1 |
| 5 (2α) | <0.1 | <0.1 | 0.5 | 0.4 | 40 | 39 | 214 | 255 | <0.1 | <0.1 |
| 5 (2β) | <0.1 | <0.1 | 0.7 | 0.5 | 44 | 44 | 224 | 299 | <0.1 | <0.1 |
| 9 | <0.1 | <0.1 | <0.1 | <0.1 | <0.1 | <0.1 | 14 | 7 | <0.1 | <0.1 |
| 10 | 1.5 | <0.1 | — | — | 27 | 62 | 83 | 115 | <0.1 | <0.1 |
| 13 | — | — | 5 | 6 | — | — | 3.9 | — | 78 | 239 |
| 14 | — | — | 10.6 | 0.5 | — | — | 0.4 | — | 4.1 | 1.4 |
| 15 | — | — | 1.3 | 0.2 | — | — | 2 | — | 0.1 | 0.1 |

*The product presented an affinity for the receptor.

| Product of example | Mineralo corticoid 2 H | Mineralo corticoid 4 H | Mineralo corticoid 24 H | Androgen 2 H | Androgen 4 H | Androgen 24 H | Progestogen 2 H | Progestogen 4 H | Progestogen 24 H | Glucocorticoid 2 H | Glucocorticoid 4 H | Glucocorticoid 24 H | Estrogen 2 H | Estrogen 4 H | Estrogen 24 H |
|---|---|---|---|---|---|---|---|---|---|---|---|---|---|---|---|
| 19 | — | — | 0 | — | — | 20 | 74 | — | 640 | — | 270 | 265 | 0 | — | — |
| 32 | — | — | 0 | — | — | 68 | 81 | — | 351 | — | 279 | 235 | 0 | — | — |
| 29 | — | — | — | — | — | 0 | 41 | — | 250 | — | 46 | 94 | 0 | — | — |
| 23 | — | — | 0 | — | — | 14.7 | 81 | — | 268 | — | 212 | 167 | 0 | — | — |
| 25 | — | — | 0 | — | — | 32 | 78 | — | 467 | — | 254 | 292 | 0 | — | — |
| 26 | — | — | 0 | — | — | 9.8 | 6.3 | — | 8.3 | — | 9 | 14 | 0 | — | — |
| 31 | — | — | 1.7 | — | — | 29 | 129 | — | 166 | — | 283 | 259 | 0 | — | — |
| 27 | — | — | 0 | — | — | 2.8 | 0.6 | — | 0.4 | — | 5.3 | 6.2 | 0 | — | — |
| 21 | — | — | 0.8 | — | — | 7.3 | 10 | — | 4.3 | — | 171 | 118 | 0 | — | — |
| 35 | — | — | — | — | — | 2.2 | 1.1 | — | 2.5 | — | 7.8 | 5 | 0 | — | — |
| 37 | — | — | 0.3 | — | — | 8 | 175 | — | 843 | — | 178 | 221 | 0 | — | — |
| 44 | — | — | 0 | — | — | 4.6 | 15.2 | — | 38 | — | 79 | 104 | 0 | — | — |

CONCLUSION

The tested compounds and especially those of Examples 2, 5,19,25,31,32 and 37 present a very remarkable affinity for glucocorticoid and progestogen receptors as well as a slightly moderate affinity for androgen receptors. These results lead to the conclusion that the products do not have any mineralcorticoid and estrogen receptors and present an agonist or antagonistic activity to glucocorticoids, progestogens and androgens. Moreover, the products of Examples 13 and 14 present an agonist or antagonistic activity to estrogens.

II. Anti-inflammatory Activity

The anti-inflammatory activity of the compound of Example 4 was determined by the classical granuloma test by a modification of the Meier et al test [Experientia, Vol. 6 (1950), p. 469] in which normal female Wistar rats weighing 100 to 110 g received an implantation of 2 pellets of cotton weighing 10 mg each under the thorax skin. The subcutaneous treatment which began immediately after the implantation for 2 days was 2 injections per day. 16 hours after the last injection, the animals were killed and the pellets together with the granuloma tissue formed were weighed in the fresh state and after 16 hours at 60° C. The weight of the granuloma was obtained by subtracting the initial weight of the cotton. The thymus was also removed and weighed to determine the thymolytic activity of the test product.

At a subcutaneous dose of 50 mg/kg, the product of Example 19 did not show any glucocorticoidal anti-inflammatory activity or thymolytic activity.

III. Antiglucocorticoidal Activity

The test used was that of Dausse et al [Molecular Pharmacology, Vol. 13 (1977), p. 948-955] entitled "The relationship between glucocorticoid structure and effects upon thymocytes" for mice thymocytes. The thymocytes of surrenalectomized rats were incubated at 37° C. for 3 hours in a nutritive medium containing $5 \times 10^{-8}$M of dexamethasone in the presence or absence of the test compound at different concentrations. Tritiated uridine was added and incubation was continued for one hour. The incubates were cooled and treated with a 5% trifluoroacetic acid solution and the mixture was filtered with Whatman GF/A paper. The filter was washed 3 times with a 5% trifluoroacetic acid solution and retained radioactivity on the filter was determined. Glucocorticoids and especially dexamethasone provoked a lessening of incorporation of tritiated uridine and the tested compounds, especially those of Examples 1,2,5,10,19,21,23,25,26,29,31,35 and 37 opposed this effect as can be seen from the following Table.

| Product of Example | $5 \times 10^{-8}$ of Dexamethasone — test product in concentration of | % inhibition of effect of Dexamethasone |
|---|---|---|
| 1 | $10^{-8}$M | 8 |
|   | $10^{-7}$M | 18 |
|   | $10^{-6}$M | * |
| 2 (17 OH) | $10^{-8}$M | 41 |
|   | $10^{-7}$M | 91 |
|   | $10^{-6}$M | * |
| 2 (17 OAc) | $10^{-8}$M | 24 |
|   | $10^{-7}$M | 76 |
|   | $10^{-6}$M | * |
| 3 | $10^{-8}$M | 0 |
|   | $10^{-7}$M | 0 |
|   | $10^{-6}$M | 60 |
| 4 | $10^{-8}$M | 0 |
|   | $10^{-7}$M | 0 |
|   | $10^{-6}$M | 51 |
| 5 (2α) | $10^{-8}$M | 19 |

-continued

| Product of Example | $5 \times 10^{-8}$ of Dexamethasone + test product in concentration of | % inhibition of effect of Dexamethasone |
|---|---|---|
|  | $10^{-7}M$ | 57 |
|  | $10^{-6}M$ | 100 |
| 5 (2β) | $10^{-8}M$ | 10 |
|  | $10^{-7}M$ | 57 |
|  | $10^{-6}M$ | * |
| 7 | $10^{-8}M$ | 0 |
|  | $10^{-7}M$ | 27 |
|  | $10^{-6}M$ | * |
| 9 | $10^{-8}M$ | 3 |
|  | $10^{-7}M$ | 1 |
|  | $10^{-6}M$ | 2 |
| 10 | $10^{-8}M$ | 0 |
|  | $10^{-7}M$ | 23 |
|  | $10^{-6}M$ | * |
| 6 | $10^{-8}M$ | 0 |
|  | $10^{-7}M$ | 0 |
|  | $10^{-6}M$ | 68 |
| 6 (17α propényle) | $10^{-8}M$ | 0 |
|  | $10^{-7}M$ | 0 |
|  | $10^{-6}M$ | 56 |

*A dose of $10^{-6}M$ inhibited the effect of dexamethasone totally

| Product of Example | $5 \cdot 10^{-8}$ Dexamethasone + Product tested | % of inhibition of effect of Dexamethasone |
|---|---|---|
| 19 | $10^{-8}M$ | 30 |
|  | $10^{-7}M$ | 70 |
|  | $10^{-6}M$ | 90 |
| 29 | $10^{-8}M$ | 18 |
|  | $10^{-7}M$ | 57 |
|  | $10^{-6}M$ | * |
| 23 | $10^{-8}M$ | 22 |
|  | $10^{-7}M$ | 53 |
|  | $10^{-6}M$ | * |
| 25 | $10^{-8}M$ | 57 |
|  | $10^{-7}M$ | 85 |
|  | $10^{-6}M$ | * |
| 26 | $10^{-8}M$ | 14 |
|  | $10^{-7}M$ | 34 |
|  | $10^{-6}M$ | 75 |
| 31 | $10^{-8}M$ | 28 |
|  | $10^{-7}M$ | 60 |
|  | $10^{-6}M$ | 99 |
| 21 | $10^{-8}M$ | 5 |
|  | $10^{-7}M$ | 15 |
|  | $10^{-6}M$ | 83 |
| 35 | $10^{-8}M$ | 4 |
|  | $10^{-7}M$ | 21 |
|  | $10^{-6}M$ | 50 |
| 37 | $10^{-8}M$ | 16 |
|  | $10^{-7}M$ | 69 |
|  | $10^{-6}M$ | * |

*A dose of $10^{-6}M$ inhibited totally the effect of dexamethasone

CONCLUSION

The products of the invention used alone do not provoke any effect of the glucocorticoid type at doses provoking an anti agonist effect and the tested products present a very remarkable antiglucocorticoid activity and are devoid of any glucocorticoid activity.

IV. Progestomimetic and Anti-progestomimetic Activity a) Groups of immature female rabbits weighing about 1 kg had administered to them subcutaneously from day 1 to day 5, 5 μg of estradiol. The product tested was afterward administered orally from day 8 to day 11 in a volume of 0.5 cm³ of water containing 0.5% of carboxymethyl cellulose and 0.2% of Tween. On day 12, the rabbits were sacrificed, their uteruses were retained and fixed in Bouin's solution and histologically studied.

The changes in the uterine endometrium were noted according to the method of McPhail. Only superior results or those equal to two units of McPhail were considered significant.

The following results were obtained.

| TREATMENT | DOSAGE mg/kg | CHANGE IN THE ENDOMETRIUM IN McPHAIL UNITS |
|---|---|---|
| Progesterone (subcutaneously) | 0.2 | 3.2 |
| Product of Example 19 (by mouth) | 0.3 | 0 |
|  | 1.0 | 0 |
| (RU 38486 or RU 486) | 3.0 | 0 |
|  | 10.0 | 0 |
|  | 50 | 0 |
| Progesterone (subcutaneously) | 0.2 | 3.0 |
| Progesterone 0.2 mg (subcutaneously) — the compound of example 19 (by mouth) | 0.3 | 2.8 |
|  | 1 | 2.1 |
|  | 3 | 1.4 |
|  | 10 | 0.6 |
|  | 20 | 0 |

*Technique described by D. A. Macginty, L. P. Anderson, and N. B. McCullough Endocrin. 1939, 24, 829

Groups of three immature female rabbits weighing about 1 kg were topically treated on the dorsal skin with 25 μg of estradiol in 10 μl of ethanol on day 1. On day 4 the product to be tested dissolved in 0.1 ml of sesame oil containing 5% benzyl alcohol was introduced into a part of the uterus isolated between two ligatures. On the sixth day the animals were sacrificed, their uteruses retained and fixed in Bouin's solution for histological examination. Changes in the uterine endometrium were noted after the method of McPhail.

The following results were obtained.

| TREATMENT | DOSE μg/RABBIT | CHANGE IN THE ENDOMETRIUM |
|---|---|---|
| Product of Example 19 | 30 | 0 |
|  | 500 | 0 |
| Progesterone | 10 | 2.7 |
| Progesterone 10 μg — Product of Example 19 | 1 | 1.6 |
|  | 3 | 1.3 |
|  | 10 | 1.0 |
|  | 30 | 0.6 |
|  | 90 | 0.6 |

Conclusion:

This product tested is devoid of progestomimetic activity while on the contrary it possesses a remarkable antiprogestomimetic activity.

V. ANTI-IMPLANTATION AND ABORTIVE ACTIVITIES IN FEMALE RATS

The first day of gestation is determined by the presence of sperm in the vagina. The product of example 19 is administered by mouth 3 consecutive days at the rate of 5 ml per kilogram as a suspension of 0.5% of carboxymethyl cellulose in water containing 0.2% Tween.

The animals were sacrificed between the 5th and 8th day after the last treatment and the uterus was examined.

The following results were obtained:

| DAYS OF TREATMENT | DOSE mg/kg/day | RESULTS |
|---|---|---|
| 1, 2, 3 | 10 | Non-implantation |
| 1, 2, 3 | 2 | No action |
| 4, 5, 6 | 10 | Non-implantation |

-continued

| DAYS OF TREATMENT | DOSE mg/kg/day | RESULTS |
|---|---|---|
| 4, 5, 6 | 2 | Non-implantation |
| 7, 8, 9 | 10 | Abortion |
| 7, 8, 9 | 2 | Abortion |
| 10, 11, 12 | 10 | Abortion |
| 10, 11, 12 | 2 | Abortion |
| 13, 14, 15 | 10 | Abortion |
| 13, 14, 15 | 2 | Abortion in 50% of the animals |

Conclusion:

This product tested showed anti-implantation activity and abortive activity in the rat at all times of the period of gestation.

Various modifications of the products and methods of the invention may be made without departing from the spirit or scope thereof and it is to be understood that the invention is intended to be limited only as defined in the appended claims.

What we claim is:

1. A compound selected from the group consisting of 19-nor-steriods of the formula

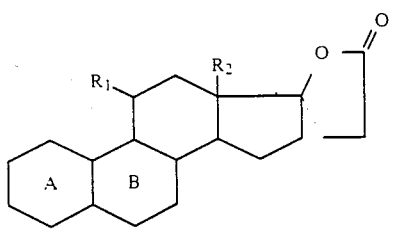

wherein $R_1$ is an organic group of 1 to 18 carbon atoms optionally containing at least one atom selected from the group consisting of oxygen, sulfur, nitrogen, phosphorus and silicon with the atom immediately adjacent the 11-carbon atom being carbon, $R_2$ is a hydrocarbon of 1 to 8 carbon atoms, the A and B rings are

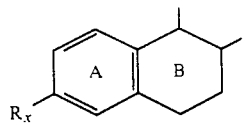

$R_x$ is selected from the group consisting of hydrogen and $OR_e$, $R_e$ is selected from the group consisting of hydrogen, substituted and unsubstituted alkyl of 1 to 6 carbon atoms and acyl, and their non-toxic, pharmacetuically acceptable acid addition salts.

2. A compound of claim 1 wherein $R_1$ is aryl or aralkyl carrying an amino of the formula

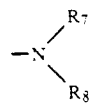

wherein $R_7$ and $R_8$ are alkyl of 1 to 8 carbon atoms or primary, secondary or tertiary alkyl of 1 to 8 carbon atoms containing at least one heteroatom of the group consisting of —O—, —S— or —N— with at least one being nitrogen or substituted with a heterocycle containing at least one nitrogen atom.

3. A compound of claim 1 wherein $R_1$ is selected from the group consisting of 2-pyridyl, 3-pyridyl, 4-pyridyl,

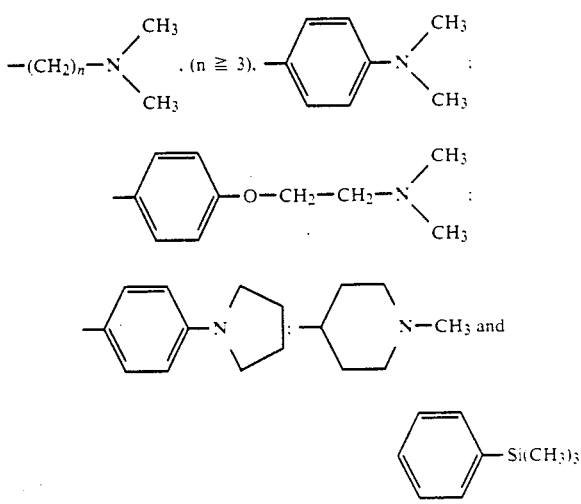

4. A compound of claim 1 wherein $R_1$ is

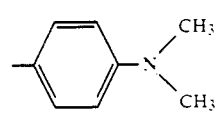

5. A compound of claim 1 wherein $R_2$ is methyl.

6. A compound of claim 1 wherein the A and B rings are selected from the group consisting of

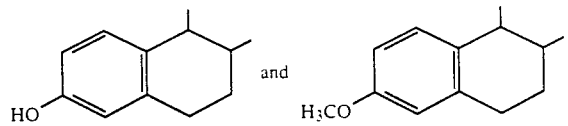

7. An antiprogestomimetic composition comprising an antiprogestomimetically effective amount of at least one compound of claim 1 and an inert carrier.

8. A method of inducing menses in warm-blooded animals comprising administering to warm-blooded animals when progresterone plays a physiologically essential role, an antiprogestomimetically effective amount of at least one compound of claim 1.

9. A method of claim 8 comprising administering to women an antiprogestomimetically effective amount of at least one compound of claim 1 during the luteal phase.

10. A method of claim 9 wherein the compound is administered at the end of luteal phase.

11. A method of claim 8 of interrupting pregnancy comprising administering to warm-blooded animals an antiprogestomimetically effective amount of at least one compound of claim 1.

12. A method of claim 8 wherein the compound is administered orally or locally.

13. A method of claim 9 wherein the compound is administered orally or locally.

14. A method of claim 8 wherein the compound is administered during 1 to 5 days.

* * * * *

UNITED STATES PATENT AND TRADEMARK OFFICE
CERTIFICATE OF CORRECTION

PATENT NO. : 5,043,332
DATED : Aug/ 27, 1991
INVENTOR(S) : Jean-Georges Teutsch; Vesperto Torelli; Roger Deraedt; Daniel Philibert and Germain Costerousse It is certified that error appears in the above-identified patent and that said Letters Patent is hereby corrected as shown below:

Col. Line
161  30

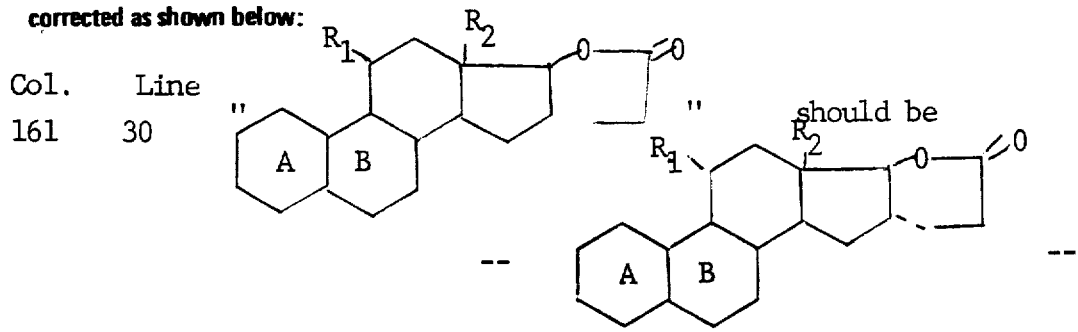

161  53  "substituted and unsubstituted" should be --substituted or unsubstituted--

162  5  "(n ≧3)" should be --(n ≧3)--

Signed and Sealed this

Sixteenth Day of March, 1993

*Attest:*

STEPHEN G. KUNIN

*Attesting Officer*    Acting Commissioner of Patents and Trademarks